US007560564B2

(12) United States Patent
Annis et al.

(10) Patent No.: US 7,560,564 B2
(45) Date of Patent: Jul. 14, 2009

(54) HETEROCYCLIC DIAMIDE INVERTEBRATE PEST CONTROL AGENTS

(75) Inventors: Gary David Annis, Landenberg, PA (US); Bruce Lawrence Finkelstein, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 306 days.

(21) Appl. No.: 11/158,200

(22) Filed: Jun. 21, 2005

(65) Prior Publication Data

US 2006/0205748 A1 Sep. 14, 2006

Related U.S. Application Data

(63) Continuation of application No. 10/469,263, filed as application No. PCT/US02/06582 on Feb. 28, 2002, now abandoned.

(60) Provisional application No. 60/273,474, filed on Mar. 5, 2001.

(51) Int. Cl.
*C07D 401/00* (2006.01)
*A61K 31/50* (2006.01)
*A61K 31/44* (2006.01)

(52) U.S. Cl. .................... 546/256; 546/275.4; 544/333; 514/252.03; 514/340

(58) Field of Classification Search ....................... None
See application file for complete search history.

(56) References Cited

U.S. PATENT DOCUMENTS

| | | | |
|---|---|---|---|
| 4,565,875 | A | 1/1986 | Cavender |
| 5,378,678 | A | 1/1995 | Tice |
| 5,538,939 | A | 7/1996 | Muenster et al. |
| 6,310,070 | B1 | 10/2001 | Yokoyama et al. |
| 6,337,417 | B1 | 1/2002 | Takematsu et al. |
| 6,716,881 | B2 | 4/2004 | Elbe et al. |
| 6,747,047 | B2 | 6/2004 | Lahm et al. |
| 6,835,743 | B2 | 12/2004 | Kimura |
| 2004/0110777 | A1 | 6/2004 | Annis et al. |
| 2004/0138450 | A1 | 7/2004 | Clark |
| 2004/0192731 | A1 | 9/2004 | Finkelstein et al. |
| 2004/0198984 | A1 | 10/2004 | Lahm et al. |
| 2004/0209923 | A1 | 10/2004 | Berger et al. |
| 2005/0075372 | A1 | 4/2005 | Lahm et al. |

FOREIGN PATENT DOCUMENTS

| | | |
|---|---|---|
| EP | 0 289 879 | 11/1988 |
| EP | 0347146 | 9/1993 |
| GB | 2090249 | 7/1982 |
| JP | 05 230016 A | 9/1993 |
| JP | 98-007509 | 1/1998 |
| JP | 2000-169461 | 6/2000 |
| NL | 06507580 | 12/1965 |
| NL | A 9202078 | 6/1994 |
| WO | WO93/007149 | 4/1993 |
| WO | WO94/05661 | 3/1994 |
| WO | WO97/28133 | 8/1997 |
| WO | WO97/047589 | 12/1997 |
| WO | WO 01/70671 | 9/2001 |
| WO | WO 03/016284 | 2/2003 |

OTHER PUBLICATIONS

Parlow, J. Het. Chem. 35, 1493, 1998, p. 1493-1499.*
Facelli et al., caplus an 2001:935593.*
Patent Abstratcts of Japan, vol. 017, No. 680 (C-1143), Dec. 16, 1993 and JP 05 230016A (Takeda Chem Ind Ltd), Sep. 7, 1993 Abstract p. 14-p. 46.
Ann Parkin et al., "Acyclic Analogues of Purine and Imidazole Nucleosides", J. Heterocyclic Chem., 19, 33 (1982), pp. 33-40.
Kristina Kasek et al., "Darstellung und Reaktionsverhalten Von 5-Substituerten 1-Phenyl-Imidazo[4,5-D][1,3]Oxazin-7(1h)-One", Z. Chem., 26. JG. (1986), p. 136.
PCT Search Report for International Application No. PCT/US02/06582 (From International Phase of US Application No. 11/158200).
Chem. Abstr. (1992), excerption No. 117:171296q, Chen, Ruyu, Synthesis and biological activity of 1-alkyl(oraryl)-5-substituted amino-4-(N-alkylcarbomoyl)pyrazol, Gaodent Xuexiao Huaxue Xuebao (1992), vol. 13, No. 1, pp. 52-55.

(Continued)

*Primary Examiner*—Golam M M Shameem
*Assistant Examiner*—Sun Jae Y Loewe

(57) ABSTRACT

This invention provides compounds of Formula (I), N-oxides and suitable salts thereof, wherein A and B are independently O or S; each J is independently a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$; K is, together with the two contiguous linking carbon atoms, a 5- or 6-membered heteroaromatic ring optionally substituted with 1 to 3 $R^4$; and $R^1$ $R^2$, $R^3$, $R^4$, $R^5$ and n are as defined in the disclosure. Also disclosed are methods for controlling an invertebrate pest comprising contacting the invertebrate pest or its environment with a biologically effective amount of a compound of Formula (I), an N-oxide thereof or a suitable salt of the compound (e.g., as a composition described herein). This invention also pertains to a composition for controlling an invertebrate pest comprising a biologically effective amount of a compound of Formula (I), an N-oxide thereof or a suitable salt of the compound and at least one additional component selected from the group consisting of surfactants, solid diluents and liquid diluents.

(I)

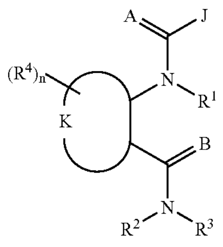

17 Claims, No Drawings

OTHER PUBLICATIONS

Chem. Abstr. (1991), excerption No. 115:135994r, Chen, Ruyu, A Study on the selective reduction of aromatic amides with lithium tetrahydroaulminate, Chinese Chemical Letters (1991), vol. 2, No. 4, pp. 269-272.

Irwin, W.J., Pyrido[3,2-d]pyrimidin-4(3H)-ones, Journal of The Chemical Society (1965), (Aug.), pp. 4240-4246.

Chem. Abstr. (1984), excerption No. 101:110944, (PL122,846).

Chem. Abstr. (1984), excerption No. 101:110944, (PL123,452).

Bielstein Database - Compound with Bielstein Registry No. 8790929.

Bielstein Database - Compound with Bielstein Registry No. 3627609.

Bielstein Database - Compound with Bielstein Registry No. 3552715.

Bielstein Database - Compound with Bielstein Registry No. 665199.

Bielstein Database - Compound with Bielstein Registry No. 665200.

Bielstein Database - Compound with Bielstein Registry No. 666149.

* cited by examiner

HETEROCYCLIC DIAMIDE INVERTEBRATE PEST CONTROL AGENTS

BACKGROUND OF THE INVENTION

This invention relates to certain heterocyclic diamides, their N-oxides, suitable salts and compositions, and a method of their use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

NL 9202078 discloses N-acyl anthranilic acid derivatives of Formula i as insecticides i

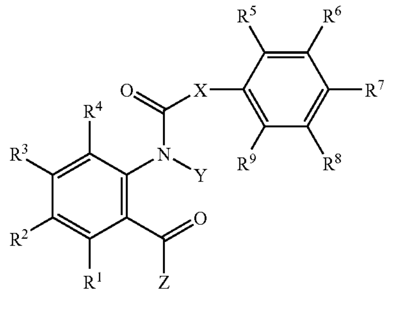

wherein inter alia, X is a direct bond; Y is H or $C_1$-$C_6$ alkyl; Z is $NH_2$, $NH(C_1$-$C_3$ alkyl) or $N(C_1$-$C_3$ alkyl$)_2$; and $R^1$ through $R^9$ are independently H, halogen, $C_1$-$C_6$ alkyl, phenyl, hydroxy, $C_1$-$C_6$ alkoxy or $C_1$-$C_7$ acyloxy.

WO01/070671 discloses N-acyl anthranilic acid derivatives of Formula i as arthropodicides i

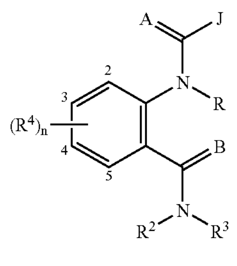

wherein, inter alia, A and B are independently O or S; J is an optionally substituted phenyl ring, 5- or 6-membered heteroaromatic ring, naphthyl ring system or an aromatic 8-, 9- or 10-membered fused heterobicyclic ring system; $R^1$ and $R^3$ are independently H or optionally substituted $C_1$-$C_6$ alkyl; $R^2$ is H or $C_1$-$C_6$ alkyl; each $R^4$ is independently H, $C_1$-$C_6$ alkyl, $C_1$-$C_6$ haloalkyl, halogen or CN; and n is 1 to 4.

SUMMARY OF THE INVENTION

This invention pertains to compounds of Formula I, and N-oxides or suitable salts thereof (I)

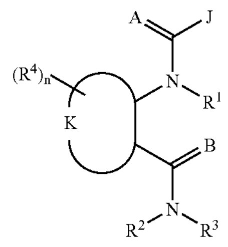

wherein

- A and B are independently O or S;
- each J is independently a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$;
- K is, together with the two contiguous linking carbon atoms, a 5- or 6-membered heteroaromatic ring optionally substituted with 1 to 3 $R^4$;
- n is 1 to 3;
- $R^1$ is H; or $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or
- $R^1$ is $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or C(=A)J;
- $R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_4$ alkoxy, $C_1$-$C_4$ alkylamino, $C_2$-$C_8$ dialkylamino, $C_3$-$C_6$ cycloalkylamino, $C_2$-$C_6$ alkoxycarbonyl or $C_2$-$C_6$ alkylcarbonyl;
- $R^3$ is H; G; or $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of G, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, and a phenyl, phenoxy or 5- or 6-membered heteroaromatic ring, each ring optionally substituted with one to three substituents independently selected from $R^6$; or
- $R^2$ and $R^3$ can be taken together with the nitrogen to which they are attached to form a ring containing 2 to 6 atoms of carbon and optionally one additional atom of nitrogen, sulfur or oxygen, and said ring may be optionally substituted with one to four substituents selected from $R^{12}$; and
- G is a 5- or 6-membered nonaromatic carbocyclic or heterocyclic ring, optionally including one or two ring members selected from the group consisting of C(=O), SO and $S(O)_2$, and optionally substituted with one to four substituents selected from $R^{12}$;
- each $R^4$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_1$-$C_4$ alkoxyalkyl, $C_1$-$C_4$ hydroxyalkyl, $C(O)R^{10}$, $CO_2R^{10}$, $C(O)NR^{10}R^{11}$, $NR^{10}R^{11}$, $N(R^{11})CO_2R^{10}$; or each $R^4$ is independently a phenyl, benzyl, phenoxy or 5- or 6-membered heteroaromatic ring, each ring optionally substituted with one to three substituents independently selected from $R^6$;

each $R^5$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $CONH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring or ring system optionally substituted with one to three substituents independently selected from $R^6$; or $(R^5)_2$ when attached to adjacent carbon atoms can be taken together as $—OCF_2O—$, $—CF_2CF_2O—$, or $—OCF_2CF_2O—$; and each $R^6$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

each $R^{10}$ is independently H, $C_1$-$C_4$ alkyl or $C_1$-$C_4$ haloalkyl;

each $R^{11}$ is independently H or $C_1$-$C_4$ alkyl; and each $R^{12}$ is independently $C_1$-$C_2$ alkyl, halogen, CN, $NO_2$ or $C_1$-$C_2$ alkoxy.

This invention also pertains to a method for controlling an invertebrate pest comprising contacting the invertebrate pest or its environment with a biologically effective amount of a compound of Formula I, an N-oxide thereof or a suitable salt of the compound (e.g., as a composition described herein). This invention also relates to such a method wherein the invertebrate pest or its environment is contacted with a biologically effective amount of a compound of Formula I or a composition comprising a compound of Formula I, an N-oxide thereof or a suitable salt of the compound and a biologically effective amount of at least one additional compound or agent for controlling invertebrate pests.

This invention also pertains to a composition for controlling an invertebrate pest comprising a biologically effective amount of a compound of Formula I, an N-oxide thereof or a suitable salt of the compound and at least one additional component selected from the group consisting of surfactants, solid diluents and liquid diluents. This invention also pertains to a composition comprising a biologically effective amount of a compound of Formula I, an N-oxide thereof or a suitable salt of the compound and an effective amount of at least one additional biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl isomers. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl.

"Aromatic" indicates that each of the ring atoms is essentially in the same plane and has a p-orbital perpendicular to the ring plane, and in which $(4n+2)$ $\pi$ electrons, when n is 0 or a positive integer, are associated with the ring to comply with Hückel's rule. The term "aromatic ring system" denotes fully unsaturated carbocycles and heterocycles in which at least one ring of a polycyclic ring system is aromatic. The term "aromatic carbocyclic ring or ring system" includes fully aromatic carbocycles and carbocycles in which at least one ring of a polycyclic ring system is aromatic (e.g. phenyl and naphthyl). The term "nonaromatic carbocyclic ring or ring system" denotes fully saturated carbocycles as well as partially or fully unsaturated carbocycles where the Hückel rule is not satisfied by any of the rings in the ring system. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C{=}CHCH_2$ and $CF_3CH_2CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC({=}O)$, $CH_3CH_2OC({=}O)$, $CH_3CH_2CH_2OC({=}O)$, $(CH_3)_2CHOC({=}O)$ and the different butoxy- or pentoxycarbonyl isomers. Examples of "alkylaminocarbonyl" include $CH_3NHC({=}O)$, $CH_3CH_2NHC({=}O)$, $CH_3CH_2CH_2NHC({=}O)$, $(CH_3)_2CHNHC({=}O)$ and the different butylamino- or pentylaminocarbonyl isomers. Examples of "dialkylaminocarbonyl" include $(CH_3)_2NC({=}O)$, $(CH_3CH_2)_2NC({=}O)$, $CH_3CH_2(CH_3)NC({=}O)$, $CH_3CH_2CH_2(CH_3)NC({=}O)$ and $(CH_3)_2CHN(CH3)C({=}O)$.

The total number of carbon atoms in a substituent group is indicated by the "$C_i$-$C_j$" prefix where i and j are numbers from 1 to 6. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted with one to three substituents" and the like indicates that one to three of the available positions on the group may be substituted. When a group contains a substituent which can be hydrogen, for example $R^1$ or $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

As noted above, J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$. The term "optionally substituted" in connection with these J groups refers to groups which are unsubstituted or have at least one non-hydrogen substituent that does not extinguish the biological activity possessed by the unsubstituted analog. An example of phenyl optionally substituted with 1 to 4 $R^5$ is the ring illustrated as U-1 in Exhibit 1, wherein $R^v$ is $R^5$ and r is an integer from 1 to 4. An example of a naphthyl group optionally substituted with 1 to 4 $R^5$ is illustrated as U-85 in Exhibit 1, wherein $R^v$ is $R^5$ and r is an integer from 1 to 4. Examples of 5- or 6-membered heteroaromatic rings optionally substituted with 1 to 4 $R^5$ include the rings U-2 through U-53 illustrated in Exhibit 1 wherein $R^v$ is $R^5$ and r is an integer from 1 to 4. Note that J-1 through J-13 below also denote 5- or 6-membered heteroaromatic rings. Note that U-2 through U-20 are examples of J-1, U-21 through U-35 and U-40 are examples of J-2, U-36 through U-39 are examples of J-3, U-41 through U-48 are examples of J-4 and U-49 through U-53 are examples of J-5. Note that J-6 is a subset of U-11, J-7 or J-10 are a subset of U-26, J-8 is a subset of U-42, J-9 is a subset of U-45, J-11 is a subset of U-4 and J-12 or J-13 are a subset of U-24. Also note that in J-6 through J-13 that $R^7$ and $R^9$ are subsets of $R^5$. Examples of aromatic 8-, 9- or 10-membered fused heterobicyclic ring systems optionally substituted with 1 to 4 $R^5$ include U-54 through U-84 illustrated in Exhibit 1 wherein $R^v$ is $R^5$ and r is an integer from 1 to 4.

Although $R^v$ groups are shown in the structures U-1 through U-85, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between $(R^v)_r$ and the U group is illustrated as floating, $(R^v)_r$ can be attached to any available carbon atom of the U group. Note that when the attachment point on the U group is illustrated as floating, the U group can be attached to the remainder of Formula I through any available carbon of the U group by replacement of a hydrogen atom.

Exhibit 1

U-1
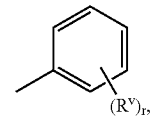

U-2
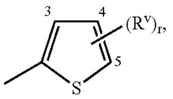

U-3
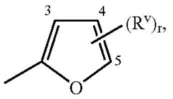

U-4
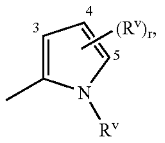

U-5
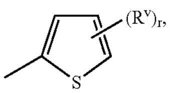

U-6
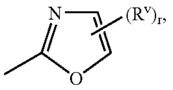

U-7
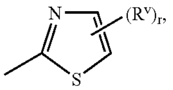

U-8
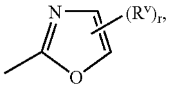

-continued

U-9
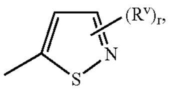

U-10
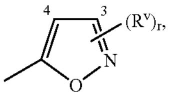

U-11
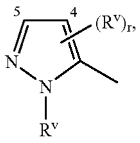

U-12
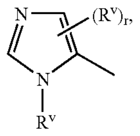

U-13
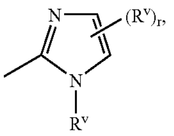

U-14
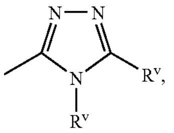

U-15
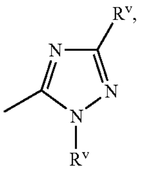

U-16
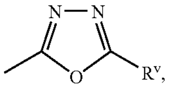

U-17
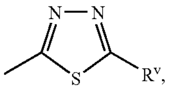

U-18
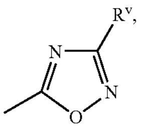

U-19
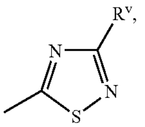

U-20
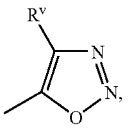

-continued
U-21
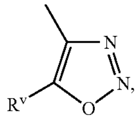
U-22
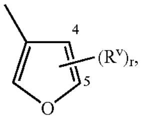
U-23
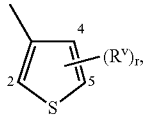
U-24
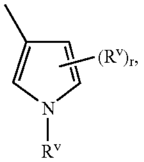
U-25
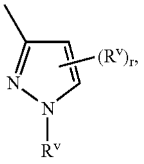
U-26
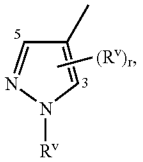
U-27
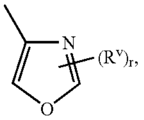
U-28
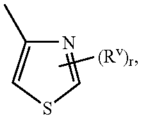
U-29
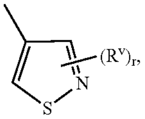
U-30
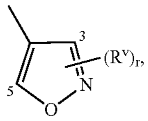
U-31
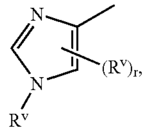
-continued
U-32
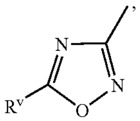
U-33
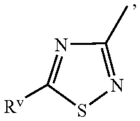
U-34
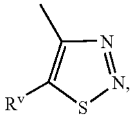
U-35
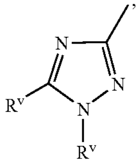
U-36
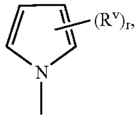
U-37
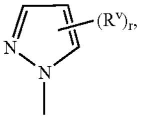
U-38
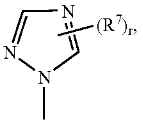
U-39
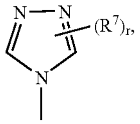
U-40
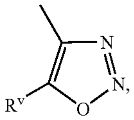
U-41
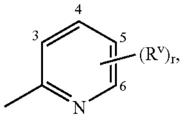
U-42
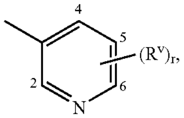
U-43
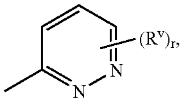

-continued
U-44
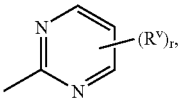
U-45
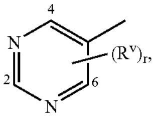
U-46
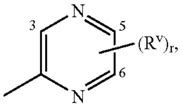
U-47
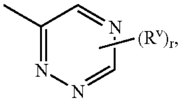
U-48
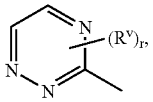
U-49
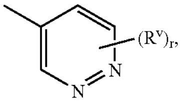
U-50
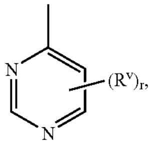
U-51
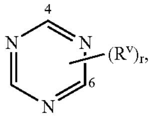
U-52
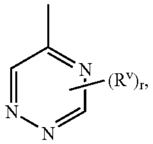
U-53
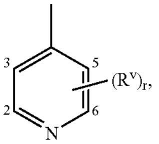
U-54
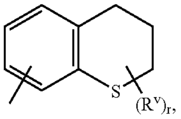
U-55
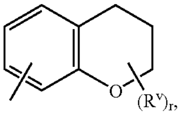
-continued
U-56
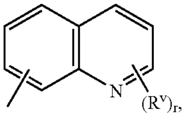
U-57
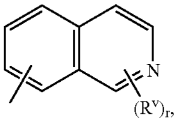
U-58
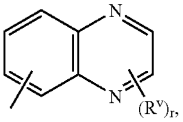
U-59
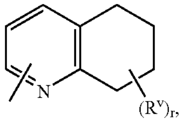
U-60
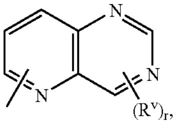
U-61
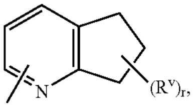
U-62
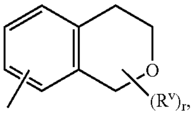
U-63
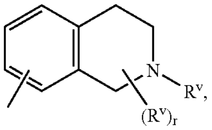
U-64
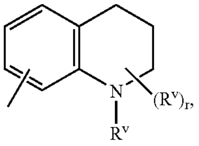
U-65
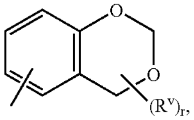
U-66
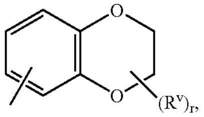
U-67
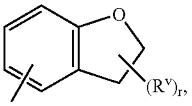

-continued

U-68

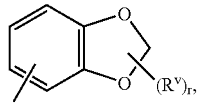

U-69

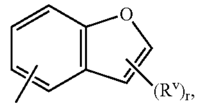

U-70

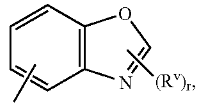

U-71

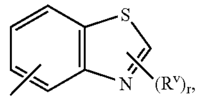

U-72

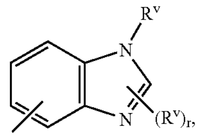

U-73

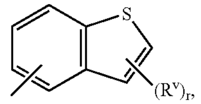

U-74

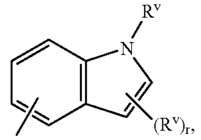

U-75

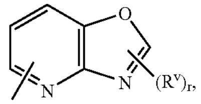

U-76

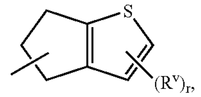

U-77

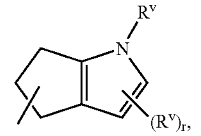

U-78

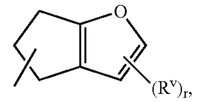

U-79

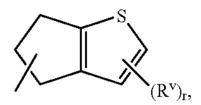

-continued

U-80

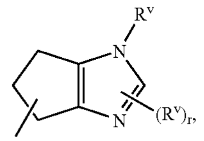

U-81

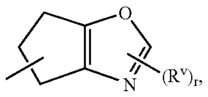

U-82

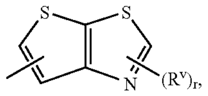

U-83

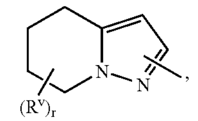

U-84

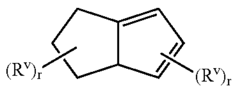

or

U-85

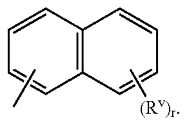

As noted above, K is, together with the two contiguous linking carbon atoms, a 5- or 6-membered heteroaromatic ring optionally substituted with 1 to 3 $R^4$. Examples of said K rings wherein said rings are optionally substituted with 1 to 3 $R^4$ include the ring systems illustrated as K-1 to K-37 in Exhibit 2, wherein n is an integer from 1 to 3 and $R^4$ is as defined above. The term "optionally substituted" in connection with these K groups refers to K groups which are unsubstituted or have at least one non-hydrogen substituent that does not extinguish the biological activity possessed by the unsubstituted analog. As with the carbon atoms in the ring, the nitrogen atoms that require substitution to fill their valence are substituted with hydrogen or with $R^4$. Although $(R^4)_n$ groups are shown in the structures K-1 to K-37, it is noted that $R^4$ does not need to be present since it is an optional substituent. Note that some K groups can only be substituted with less than 3 $R^4$ groups (e.g. K-7 through K-10, K-15, K-16, K-20, K-21, K-23, K-24, K-26 and K-27 can only be substituted with one $R^4$). In the exemplified K groups, the upper right bond is attached through the available linking carbon atom to the nitrogen atom of the $NR^1(=A)J$ portion of Formula I and the lower right bond is attached through the available linking carbon atom to the carbon atom of the $C(=B)NR^2R^3$ portion of Formula I. The wavy line indicates that the K ring is attached to the remainder of Formula I as illustrated below.

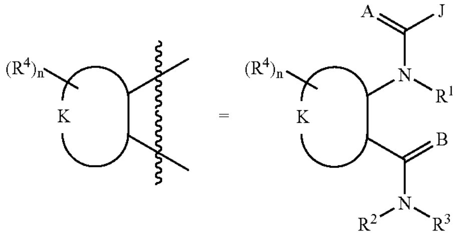

I

Exhibit 2
K-1
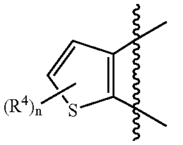
,
K-2
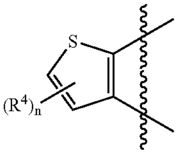
,
K-3
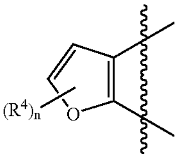
,
K-4
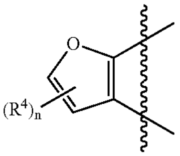
,
K-5
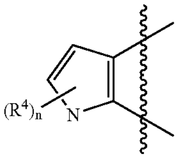
,
K-6
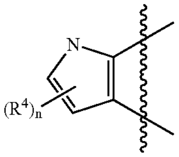
,
K-7
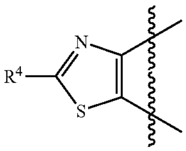
,
K-8
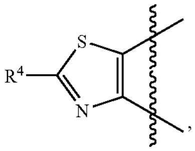
,
K-9
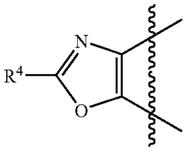
,
-continued
K-10
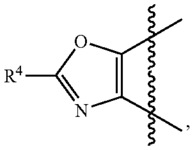
,
K-11
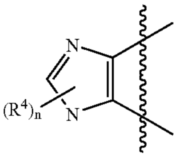
,
K-12
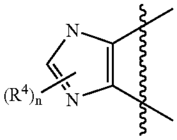
,
K-13
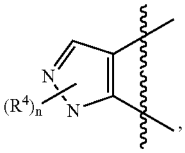
,
K-14
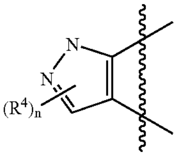
,
K-15
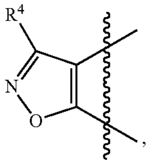
,
K-16
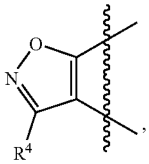
,
K-17
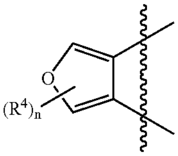
,
K-18
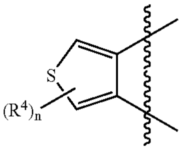
, -continued
K-19
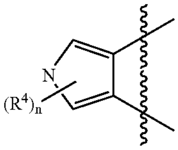,
K-20
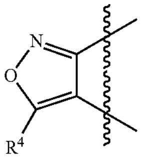,
K-21
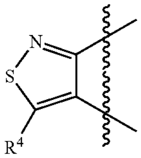,
K-22
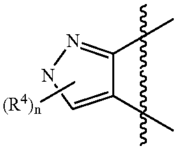,
K-23
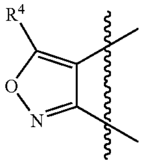,
K-24
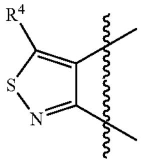,
K-25
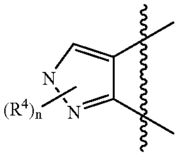,
K-26
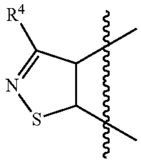,
K-27
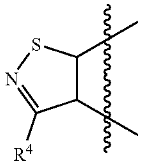,
-continued
K-28
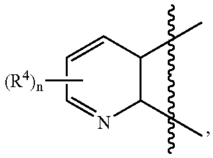,
K-29
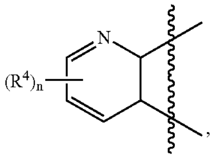,
K-30
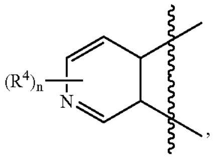,
K-31
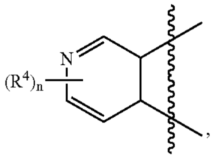,
K-32
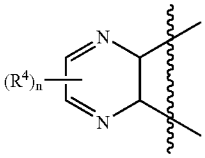,
K-33
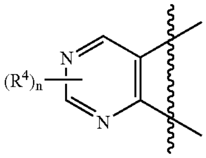,
K-34
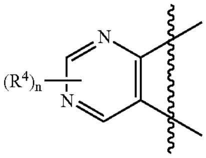,
K-35
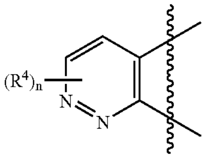,
K-36
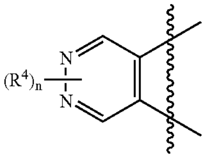
and -continued

K-37

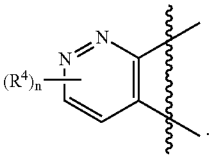

Preferred K rings include optionally substituted thiophene, isoxazole, isothiazole, pyrazole, pyridine and pyrimidine rings. More preferred K rings include K-1, K-14, K-15, K-18, K-23, K-28, K-29, K-30, K-31 and K-33. Most preferred are K-28, K-31 and K-33.

As noted above, $R^3$ can be (among others) $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of a phenyl ring, or 5- or 6-membered heteroaromatic ring, each ring optionally substituted with one to three substituents independently selected from $R^6$. Examples of such rings incorporated into said $R^3$ groups include the rings illustrated as U-1 through U-53 and U-86 illustrated in Exhibit 1, except that such rings are optionally substituted with 1 to 3 substituents independently selected from $R^6$ rather than $(R^v)_r$ and are attached to an $R^3$ group selected from the list immediately above.

As noted above, $R^3$ can be (among others) G, or $C_1$-$C_6$ alkyl, $C_2$-$C_6$ alkenyl, $C_2$-$C_6$ alkynyl, $C_3$-$C_6$ cycloalkyl, each optionally substituted with G; wherein G is a 5- or 6-membered nonaromatic carbocyclic or heterocyclic ring, optionally including one or two ring members selected from the group consisting of C(═O), SO or $S(O)_2$ and optionally substituted with 1 to 4 substituents selected from $R^{12}$. The term "optionally substituted" in connection with these G groups refers to groups which are unsubstituted or have at least one non-hydrogen substituent that does not extinguish the biological activity possessed by the unsubstituted analog. Note that when the attachment point on the G group is illustrated as floating, the G group can be attached to the remainder of Formula I through any available carbon of the G group by replacement of a hydrogen atom. The optional substituents can be attached to any available carbon by replacing a hydrogen atom. Examples of 5- or 6-membered nonaromatic carbocyclic rings as G include the rings illustrated as G-1 through G-8 of Exhibit 3. Examples of 5- or 6-membered nonaromatic heterocyclic rings as G include the rings illustrated as G-9 through G-48 of Exhibit 3. Note that when G comprises a ring selected from G-31 through G-34, G-37 and G-38, $Q^1$ is selected from O, S or N. Note that when G is G-11, G13, G-14, G16, G-23, G-24, G-30 through G-34, G-37 and G-38 and $Q^1$ is N, the nitrogen atom can complete its valence by substitution with either H or $C_1$-$C_2$ alkyl.

Exhibit 3

G-1

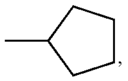

G-2

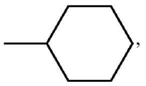

-continued

G-3

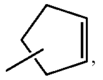

G-4

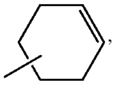

G-5

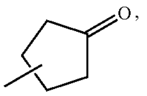

G-6

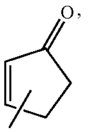

G-7

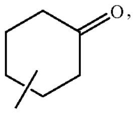

G-8

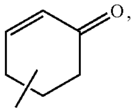

G-9

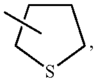

G-10

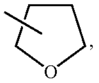

G-11

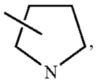

G-12

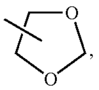

G-13

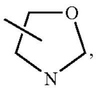

G-14

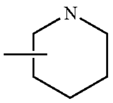

G-15

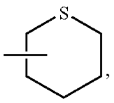

G-16

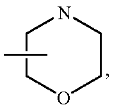

-continued

G-17

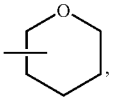

G-18

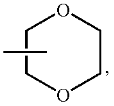

G-19

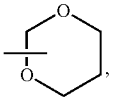

G-20

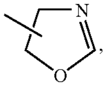

G-21

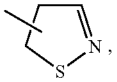

G-22

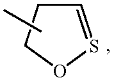

G-23

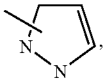

G-24

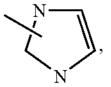

G-25

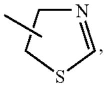

G-26

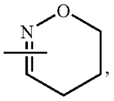

G-27

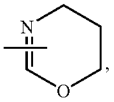

G-28

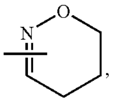

G-29

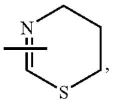

G-30

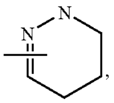

-continued

G-31

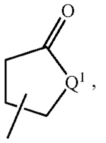

G-32

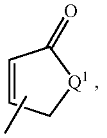

G-33

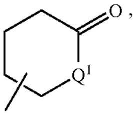

G-34

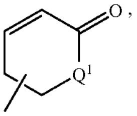

G-35

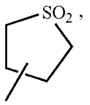

G-36

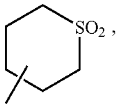

G-37

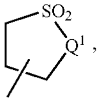

G-38

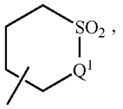

As noted above, each $R^4$ can be independently (among others) a phenyl, benzyl, phenoxy or 5- or 6-membered heteroaromatic ring, each ring optionally substituted with one to three substituents independently selected from $R^6$. Examples of such $R^4$ groups include the rings or ring systems illustrated as U-1 through U-53, U-86 and U-87 illustrated in Exhibit 1, except that such rings are optionally substituted with 1 to 3 substituents independently selected from $R^6$ rather than $(R^v)_r$.

As noted above, each $R^5$ can be independently (among others) a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from $R^6$. Examples of such $R^5$ groups include the rings or ring systems illustrated as U-1 through U-88 illustrated in Exhibit 1, except that such rings are optionally substituted with 1 to 3 substituents independently selected from $R^6$ rather than $(R^v)_r$.

Preferred compounds for reasons of better activity and/or ease of synthesis are:

Preferred 1. Compounds of Formula I above, and N-oxides and suitable salts thereof, wherein A and B are both O and J is a phenyl ring optionally substituted with 1 to 4 $R^5$.

Preferred 2. Compounds of Preferred 1 wherein each $R^4$ is independently $C_1$-$C_4$ alkyl, $C_1$-$C_4$ haloalkyl, halogen, CN, $NO_2$ or $C_1$-$C_4$ alkoxy, and one $R^4$ group is attached to the K ring at the atom adjacent to either the $NR^1C(=A)J$ moiety or the $C(=B)NR^2R^3$ moiety; and each $R^5$ is independently H, halogen, $C_1$-$C_4$ alkyl, $C_1$-$C_2$ alkoxy, $C_1$-$C_4$ haloalkyl, CN, $NO_2$, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or each $R^5$ is independently a phenyl or a 5- or 6-membered heteroaromatic ring, each ring optionally substituted with one to three substituents independently selected from $R^6$; or $(R^5)_2$ when attached to adjacent carbon atoms can be taken together as $—OCF_2O—$, $—CF_2CF_2O—$ or $—OCF_2CF_2O—$.

Preferred 3. Compounds of Preferred 2 wherein $R^1$ is H;

$R^2$ is H or $CH_3$;

$R^3$ is $C_1$-$C_4$ alkyl optionally substituted with one or more substituents independently selected from halogen, CN, $OCH_3$ or $S(O)_pCH_3$;

each $R^4$ is independently $CH_3$, $CF_3$, CN or halogen, and one $R^4$ group is attached to the K ring at the atom adjacent to the $NR^1C(=A)J$ moiety;

each $R^5$ is independently H, halogen, methyl, $CF_3$, $OCF_3$, $OCHF_2$, $S(O)_pCF_3$, $S(O)_pCHF_2$, $OCH_2CF_3$, $OCF_2CHF_2$, $S(O)_pCH_2CF_3$ or $S(O)_pCF_2CHF_2$; or a phenyl, pyrazole, imidazole, triazole, pyridine or pyrimidine ring, each ring optionally substituted with one to three substituents independently selected from $C_1$-$C_4$ alkyl, $C_1$-$C_4$ haloalkyl, halogen or CN; and p is 0, 1 or 2.

Preferred 4. Compounds of Preferred 3 wherein $R^3$ is $C_1$-$C_4$ alkyl.

Preferred 5. Compounds of Formula I wherein

A and B are both O;

J is a 5- or 6-membered heteroaromatic ring selected from the group consisting of J-1, J-2, J-3, J-4 and J-5

J-1

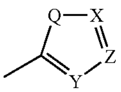

J-2

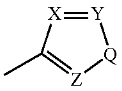

J-3

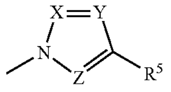

J-4

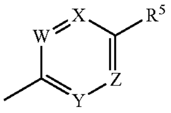

-continued

J-5

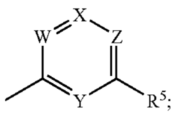

Q is O, S or $NR^5$; and

W, X, Y and Z are independently N or $CR^5$, provided that in J-4 and J-5 at least one of W, X, Y or Z is N.

Preferred 6. Compounds of Preferred 5 wherein each $R^4$ is independently $C_1$-$C_4$ alkyl, $C_1$-$C_4$ haloalkyl, halogen, CN, $NO_2$ or $C_1$-$C_4$ alkoxy, and one $R^4$ group is attached to the K ring at the atom adjacent to either the $NR^1C(=A)J$ moiety or the $C(=B)NR^2R^3$ moiety; and each $R^5$ is independently H, $C_1$-$C_4$ alkyl, $C_1$-$C_4$ haloalkyl, halogen, CN, $NO_2$, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or a phenyl or a 5- or 6-membered heteroaromatic ring, each ring optionally substituted with $R^6$.

Preferred 7. Compounds of Preferred 6 wherein

J is selected from the group consisting of J-6, J-7, J-8, J-9, J-10, J-11, J-12 and J-13

J-6

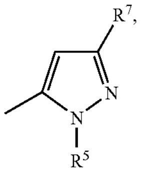

J-7

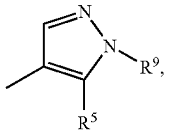

J-8

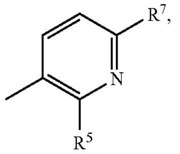

J-9

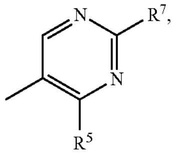

J-10

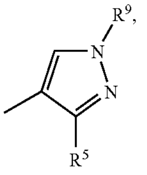

-continued

J-11

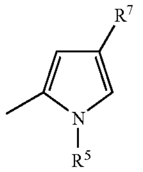

J-12

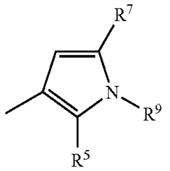

and

J-13

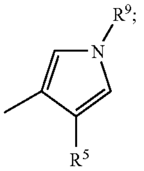

$R^5$ is H, $C_1$-$C_4$ alkyl, $C_1$-$C_4$ haloalkyl, or

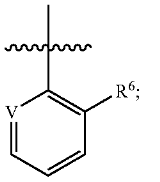

V is N, CH, CF, CCl, CBr or CI;

each $R^6$ and $R^7$ is independently H, $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ haloalkoxy or $C_1$-$C_4$ haloalkylthio; and $R^9$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl; provided $R^7$ and $R^9$ are not both H.

Preferred 8. Compounds of Preferred 7 wherein V is N.

Preferred 9. Compounds of Preferred 7 wherein V is CH, CF, CCl or CBr.

Preferred 10. Compounds of Preferred 8 or Preferred 9 wherein $R^1$ is H;

$R^2$ is H or $CH_3$;

$R^3$ is $C_1$-$C_4$ alkyl optionally substituted with one or more substituents independently selected from halogen, CN, $OCH_3$ or $S(O)_pCH_3$;

each $R^4$ is independently $CH_3$, $CF_3$, CN or halogen, and one $R^4$ group is attached to the K ring at the atom adjacent to the $NR^1C(=A)J$ moiety;

$R^6$ is $C_1$-$C_4$ alkyl, $C_1$-$C_4$ haloalkyl, halogen or CN;

$R^7$ is H, $CH_3$, $CF_3$, $OCH_2CF_3$, $OCHF_2$ or halogen; and p is 0, 1 or 2.

Preferred 11. Compounds of Preferred 10 wherein $R^3$ is $C_1$-$C_4$ alkyl; one $R^4$ group is independently $CH_3$, Cl, Br or I and is attached to the K ring at the atom adjacent to the $NR^1C(=A)J$ moiety; and a second optional $R^4$ is H, F, Cl, Br, I or $CF_3$.

Preferred 12. Compounds of Preferred 11 wherein J is J-6; $R^6$ is Cl or Br; and $R^7$ is halogen, $OCH_2CF_3$ or $CF_3$.

Preferred 13. Compounds of Preferred 12 wherein V is N; $R^3$ is methyl, ethyl, isopropyl or tertiary butyl; and $R^7$ is Br, Cl, $OCH_2CF_3$ or $CF_3$.

Preferred 14. Compounds of Preferred 11 wherein J is J-7; $R^6$ is Cl or Br; and $R^9$ is $CF_3$, $CHF_2$, $CH_2CF_3$ or $CF_2CHF_2$.

Preferred 15. Compounds of Preferred 11 wherein J is J-8; $R^6$ is Cl or Br; and $R^7$ is halogen, $OCH_2CF_3$ or $CF_3$.

Preferred 16. Compounds of Preferred 11 wherein J is J-9; $R^6$ is Cl or Br; and $R^7$ is $OCH_2CF_3$ or $CF_3$.

Preferred 17. Compounds of Preferred 11 wherein J is J-10; $R^6$ is Cl or Br; and $R^9$ is $CF_3$, $CHF_2$, $CH_2CF_3$ or $CF_2CHF_2$.

Preferred 18. Compounds of Preferred 11 wherein J is J-11; $R^6$ is Cl or Br; and $R^7$ is halogen, $OCH_2CF_3$, or $CF_3$.

Preferred 19. Compounds of Preferred 11 wherein J is J-12; $R^6$ is Cl or Br; $R^7$ is H, halogen or $CF_3$, and $R^9$ is H, $CF_3$, $CHF_2$, $CH_2CF_3$, or $CF_2CHF_2$.

Preferred 20. Compounds of Preferred 11 wherein J is J-13; $R^6$ is Cl or Br; and $R^9$ is H, $CF_3$, $CHF_2$, $CH_2CF_3$ or $CF_2CHF_2$.

Most preferred is the compound of Formula I selected from the group consisting of:

4-[[[1-(2-Chlorophenyl)-3-(trifluoromethyl)-1H-pyrazol-5-yl]carbonyl]amino]-5-methyl-N-(1-methylethyl)-3-pyridincarboxamide, 4-Methyl-N-(1-methylethyl)-3-[[2-methyl-4-(trifluoromethyl)benzoyl]amino]-2-thiophencarboxamide, 1-Methyl-N-(1-methylethyl)-5-[[4-(trifluoromethyl)benzoyl]amino]-1H-pyrazole-4-carboxamide;

4-[[[3-Bromo-1-(3-chloro-2-pyridinyl)-1H-pyrazol-5-yl]carbonyl]amino]-5-chloro-N-methyl-3-pyridinecarboxamide;

3-[[[3-Bromo-1-(3-chloro-2-pyridinyl)-1H-pyrazol-5-yl]carbonyl]amino]-2,6-dichloro-N-methyl-4-pyridinecarboxamide;

2,6-dichloro-3-[[[1-(3-chloro-2-pyridinyl)-3-(trifluoromethyl)-1H-pyrazol-5-yl]carbonyl]amino]-N-(1-methylethyl)-4-pyridinecarboxamide;

3-[[[3-Bromo-1-(3-chloro-2-pyridinyl)-1H-pyrazol-5-yl]carbonyl]amino]-6-chloro-N,4-dimethyl-2-pyridinecarboxamide;

3-[[[3-Bromo-1-(3-chloro-2-pyridinyl)-1H-pyrazol-5-yl]carbonyl]amino]-4,6-dichloro-N-methyl-2-pyridinecarboxamide;

5-[[[3-Chloro-1-(3-chloro-2-pyridinyl)-1H-pyrazol-5-yl]carbonyl]amino]-N,6-dimethyl-4-pyrimidinecarboxamide; and 5-[[[3-Bromo-1-(3-chloro-2-pyridinyl)-1H-pyrazol-5-yl]carbonyl]amino]-N,N,2,6-tetramethyl-4-pyridinecarboxamide.

This invention also pertains to a composition for controlling an invertebrate pest comprising a biologically effective amount of a compound of Formula I, an N-oxide thereof or a suitable salt thereof and at least one additional component selected from the group consisting of surfactants, solid diluents and liquid diluents. This invention also pertains to a composition comprising a biologically effective amount of a compound of Formula I, an N-oxide thereof or a suitable salt thereof and an effective amount of at least one additional biologically active compound or agent. The preferred compositions of the present invention are those which comprise the above preferred compounds.

This invention also pertains to a method for controlling an invertebrate pest comprising contacting the invertebrate pest or its environment with a biologically effective amount of a compound of Formula I, an N-oxide thereof or a suitable salt thereof (e.g., as a composition described herein). This invention also relates to such a method wherein the invertebrate pest or its environment is contacted with a biologically effective amount of a compound of Formula I or a composition comprising a compound of Formula I, an N-oxide thereof or a suitable salt thereof and a biologically effective amount of at least one additional compound or agent for controlling invertebrate pests. The preferred methods of use are those involving the above preferred compounds.

Of note are compounds of Formula 1 (a subset of Formula I) and N-oxides or suitable salts thereof

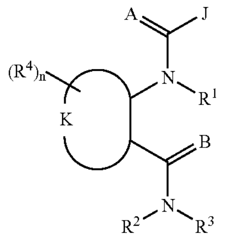
1 wherein

A and B are independently O or S;

each J is independently a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$;

K is, together with the two contiguous linking carbon atoms, a 5- or 6-membered heteroaromatic ring optionally substituted with 1 to 3 $R^4$;

n is 1 to 3;

$R^1$ is H; or $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^1$ is $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or C(=A)J;

$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_4$ alkoxy $C_1$-$C_4$ alkylamino, $C_2$-$C_8$ dialkylamino, $C_3$-$C_6$ cycloalkylamino, $C_2$-$C_6$ alkoxycarbonyl or $C_2$-$C_6$ alkylcarbonyl;

$R^3$ is H; G; $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of halogen, G, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, and a phenyl, phenoxy or 5- or 6-membered heteroaromatic ring, each ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl and $C_3$-$C_6$ trialkylsilyl; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl or $C_2$-$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with 1 to 4 substituents selected from the group consisting of $C_1$-$C_2$ alkyl, halogen, CN, $NO_2$ and $C_1$-$C_2$ alkoxy;

G is a 5- or 6-membered nonaromatic carbocyclic or heterocyclic ring, optionally including one or two ring members selected from the group consisting of C(=O), SO or $S(O)_2$ and optionally substituted with 1 to 4 substituents selected from the group consisting of $C_1$-$C_2$ alkyl, halogen, CN, $NO_2$ and $C_1$-$C_2$ alkoxy;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino or $C_3$-$C_6$ trialkylsilyl; or each $R^4$ is independently phenyl, benzyl or phenoxy, each optionally substituted with $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

each $R^5$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $CONH_2$ $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $(R^5)_2$ when attached to adjacent carbon atoms can be taken together as $—OCF_2O—$, $—CF_2CF_2O—$, or $—OCF_2CF_2O—$.

Also of note are selected compounds for reasons of cost, ease of synthesis and/or biological efficacy:

Selection A. Compounds of Formula 1 wherein K is, together with the two linking atoms, a thiophene, pyrazole, isoxazole, pyridine or pyrimidine, optionally substituted with 1 to 3 $R^4$.

Selection B. Compounds of Selection A wherein J is independently a phenyl ring or a 5- or 6-membered heteroaromatic ring wherein each ring is optionally substituted with 1 to 2 $R^5$.

Selection C. Compounds of Selection A wherein

J is a phenyl ring or a 5- or 6-membered heteroaromatic ring selected from the group consisting of J-1, J-2, J-3, J-4 and J-5

J-1

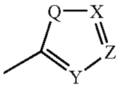

J-2

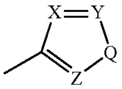

J-3

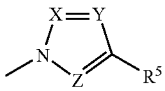

J-4

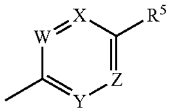

J-5

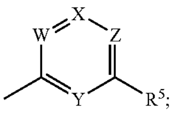

Q is O, S or $NR^5$; and

W, X, Y and Z are independently N or $CR^5$, provided that in J-4 and J-5 at least one of W, X, Y or Z is N.

Selection D. Compounds of Selection B or Selection C wherein

A and B are both O;

n is 1 to 2;

$R^1$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl;

$R^2$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl;

$R^3$ is $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from the group consisting of halogen, CN, $C_1$-$C_2$ alkoxy, $C_1$-$C_2$ alkylthio, $C_1$-$C_2$ alkylsulfinyl and $C_1$-$C_2$ alkylsulfonyl;

one of the $R^4$ groups is attached to the heteroaromatic ring at one of the two positions ortho to the two linking atoms, and said $R^4$ is $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl;

each $R^5$ is independently H, $C_1$-$C_4$ alkyl, $C_1$-$C_4$ haloalkyl, halogen, CN, $NO_2$, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; or a phenyl or a 5- or 6-membered heteroaromatic ring, each ring optionally substituted with $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $(R^5)_2$ when attached to adjacent carbon atoms can be taken together as $—OCF_2O—$, $—CF_2CF_2O—$ or $—OCF_2CF_2O—$.

Selection E. Compounds of Selection D wherein

J is selected from the group consisting of phenyl, pyridine, pyrimidine, pyrazole, imidazole, triazole, thiophene, thiazole and oxazole, furan, isothiazole and isoxazole, each optionally substituted with 1 to 2 $R^5$.

Selection F. Compounds of Selection E wherein

J is selected from the group consisting of phenyl, pyridine, pyrimidine, pyrazole, thiophene and thiazole, each optionally substituted with 1 to 2 $R^5$;

$R^1$ and $R^2$ are both H;

$R^3$ is $C_1$-$C_4$ alkyl optionally substituted with halogen, CN, $OCH_3$, $S(O)_pCH_3$;

each $R^4$ is independently $CH_3$, $CF_3$, $OCF_3$, $OCHF_2$, $S(O)_pCF_3$, $S(O)_pCHF_2$, CN or halogen;

each $R^5$ is independently H, halogen, $CH_3$, $CF_3$, $OCHF_2$, $S(O)_pCF_3$, $S(O)_pCHF_2$, $OCH_2CF_3$, $OCF_2CHF_2$, $S(O)_pCH_2CF_3$, $S(O)_pCF_2CHF_2$; or phenyl, pyrazole, imidazole, triazole, pyridine or pyrimidine, each ring optionally substituted with $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, halogen or CN; and p is 0, 1 or 2.

Selection G. Compounds of Selection F wherein $R^3$ is $C_1$-$C_4$ alkyl.

Selection H. Compounds of Selection G wherein J is a phenyl optionally substituted with 1 to 2 $R^5$.

Selection I. Compounds of Selection H wherein one $R^5$ is a phenyl optionally substituted with $C_1$-$C_4$ alkyl, $C_1$-$C_4$ haloalkyl, halogen or CN.

Selection J. Compounds of Selection H wherein one $R^5$ is a pyrazole, imidazole, triazole, pyridine or pyrimidine, each ring optionally substituted with $C_1$-$C_4$ alkyl, $C_1$-$C_4$ haloalkyl, halogen or CN.

Selection K. Compounds of Selection I wherein J is a pyridine optionally substituted with 1 to 2 $R^5$.

Selection L. Compounds of Selection K wherein one $R^5$ is a phenyl optionally substituted with $C_1$-$C_4$ alkyl, $C_1$-$C_4$ haloalkyl, halogen or CN.

Selection M. Compounds of Selection K wherein one $R^5$ is a pyrazole, imidazole, triazole, pyridine or pyrimidine, each ring optionally substituted with $C_1$-$C_4$ alkyl, $C_1$-$C_4$ haloalkyl, halogen or CN.

Selection N. Compounds of Selection I wherein J is a pyrimidine optionally substituted with 1 to 2 $R^5$.

Selection O. Compounds of Selection N wherein one $R^5$ is a phenyl optionally substituted with $C_1$-$C_4$ alkyl, $C_1$-$C_4$ haloalkyl, halogen or CN.

Selection P. Compounds of Selection N wherein one $R^5$ is a pyrazole, imidazole, triazole, pyridine or pyrimidine, each ring optionally substituted with $C_1$-$C_4$ alkyl, $C_1$-$C_4$ haloalkyl, halogen or CN.

Selection Q. Compounds of Selection I wherein J is a pyrazole optionally substituted with 1 to 2 $R^5$.

Selection R. Compounds of Selection Q wherein one $R^5$ is a phenyl optionally substituted with $C_1$-$C_4$ alkyl, $C_1$-$C_4$ haloalkyl, halogen or CN.

Selection S. Compounds of Selection Q wherein one $R^5$ is a pyrazole, imidazole, triazole, pyridine or pyrimidine, each ring optionally substituted with $C_1$-$C_4$ alkyl, $C_1$-$C_4$ haloalkyl, halogen or CN.

Selection T. Compounds of Selection S wherein one $R^5$ is a pyridine optionally substituted with $C_1$-$C_4$ alkyl, $C_1$-$C_4$ haloalkyl, halogen or CN.

Most select is the compound of Formula 1 selected from the group consisting of:

4-[[[1-(2-Chlorophenyl)-3-(trifluoromethyl)-1H-pyrazol-5-yl]carbonyl]amino]-5-methyl-N-(1-methylethyl)-3-pyridincarboxamide, 4-Methyl-N-(1-methylethyl)-3-[[2-methyl-4-(trifluoromethyl)benzoyl]amino]-2-thiophencarboxamide, and 1-Methyl-N-(1-methylethyl)-5-[[4-(trifluoromethyl)benzoyl]amino]-1H-pyrazole-4-carboxamide.

The compounds of Formula I can be prepared by one or more of the following methods and variations as described in Schemes 1-19. The definitions of A, B, J, K, $R^1$, $R^2$, $R^3$, $R^4$, $R^5$ and n in the compounds of Formulae I and 2-41 below are as defined above in the Summary of the Invention. Compounds of Formulae Ia-c, 2a-b and 4a-g are various subsets of the compounds of Formula I, 2 and 4, respectively. Of note are compounds of Formulae I, 2, 5, 6, 6a, 13, 14, 15, 40 and 41 wherein K is selected from the group consisting of optionally substituted thiophene, isoxazole, isothiazole, pyrazole, pyridine and pyrimidine rings. Also of note are compounds of Formulae I, 2, 5, 6, 6a, 13, 14, 15, 40 and 41 wherein K is K-1, K-14, K-15, K-18, K-23, K-28, K-29, K-30, K-31 and K-33. Of particular note are compounds of Formulae I, 2, 5, 6, 6a, 13, 14, 15, 40 and 41 wherein K is K-28, K-31 and K-33.

Compounds of Formula I can be prepared by procedures outlined in Schemes 1-19. A typical procedure is detailed in Scheme 1 and involves coupling of an ortho amino carboxylic acid amide of Formula 2 with an acid chloride of Formula 3 in the presence of an acid scavenger to provide the compound of Formula Ia. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. In a subsequent step, amides of Formula Ia can be converted to thioamides of Formula Ib using a variety of standard thio transfer reagents including phosphorus pentasulfide and Lawesson's reagent.

Scheme 1

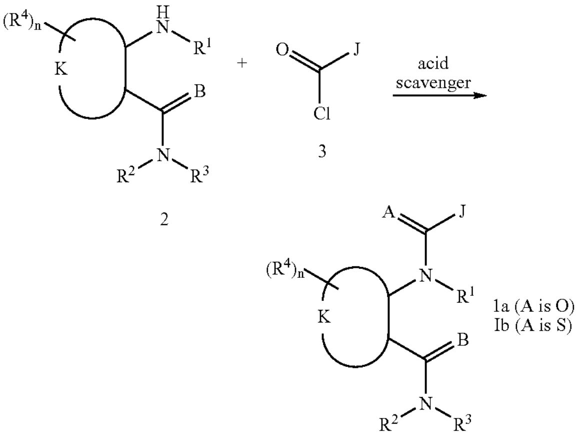

An alternate procedure for the preparation of compounds of Formula Ia involves coupling of an amide of Formula 2 with an acid of Formula 4 in the presence of a dehydrating agent such as dicyclohexylcarbodiimide (DCC). Polymer supported reagents are useful here, such as polymer-bound cyclohexylcarbodiimide. Synthetic procedures of Schemes 1 and 2 are only representative examples of useful methods for the preparation of Formula I compounds as the synthetic literature is extensive for this type of reaction.

Scheme 2

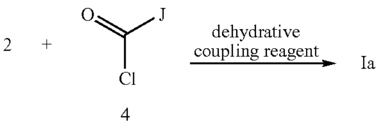

One skilled in the art will also realize that acid chlorides of Formula 3 may be prepared from acids of Formula 4 by numerous well-known methods.

An alternate procedure for the preparation of compounds of Formula Ia involves coupling of an ortho amino carboxylic acid ester of Formula 5 with an acid chloride of Formula 3 by a method similar to that described in Scheme 1, followed by transformation of the ester group into an amide functionality. This transformation can be achieved by an amination with an amine of Formula 7. A Lewis acid such as trimethylaluminum as shown in Scheme 3 may catalyze this reaction.

Scheme 3

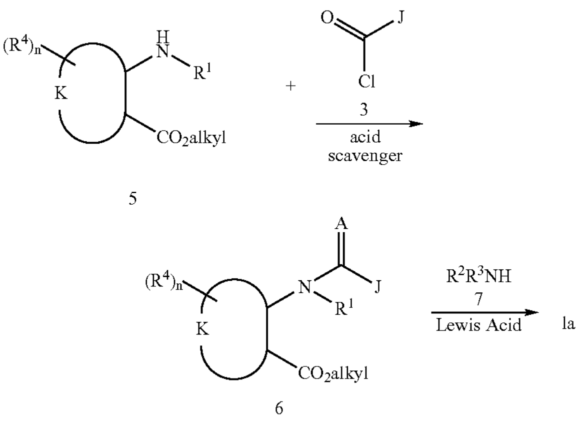

Alternatively the ester 6 can be transformed to an amide (6a) as shown in Scheme 4 by saponification with a base such as aqueous sodium hydroxide followed by dehydrative coupling with an amine of Formula 7 by a procedure similar to that described in Scheme 2.

Scheme 4

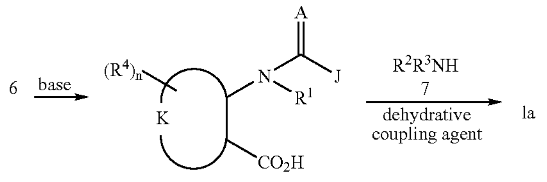

6a

Benzoic acids of Formula 4 (J is optionally substituted phenyl) are generally well known in the art as are procedures for their preparation. One particularly useful subset of benzoic acids of this invention are 2-methyl-4-perfluoroalkyl benzoic acids of Formula 4a ($R^5$(a) equals e.g. $CF_3$, $C_2F_5$, $C_3F_7$). The synthesis for these compounds is outlined in Schemes 5-9. Benzoic acids of Formula 4a may be prepared from the benzonitriles of Formula 8 by hydrolysis. The conditions used may involve the use of a base such as an alkaline metal hydroxide or alkoxide (e.g. potassium or sodium hydroxide) in a solvent such as water, ethanol or ethylene glycol (e.g. *J. Chem. Soc.* 1948, 1025). Alternatively, the hydrolysis may be carried out using an acid such as sulfuric acid or phosphoric acid in a suitable solvent such as water (e.g. *Org. Synth.* 1955, Coll. vol. 3, 557). The choice of the conditions is contingent on the stability of $R^5$ to the reaction conditions and elevated temperatures are usually employed to achieve this transformation.

Scheme 5

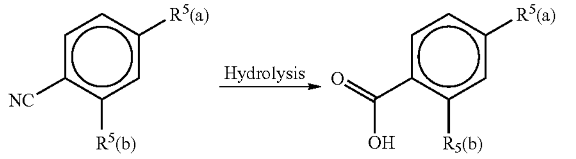

8

4a $R^5$(b) is Me

Nitriles of Formula 8 may be prepared from anilines of Formula 9 by the classical sequence involving diazotization and treatment of the intermediate diazonium salt with a copper cyanide salt (e.g. *J. Amer. Chem. Soc.* 1902, 24, 1035).

Scheme 6

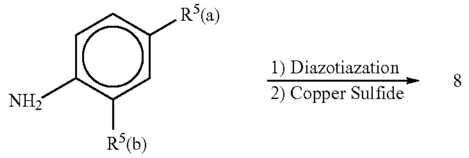

9 $R^5$(b) is Me

Anilines of Formula 9 may be prepared from compounds of Formula 10. This transformation may be achieved by a well-known procedure that employs Raney Nickel (*Org. Synth.* Coll. Vol. VI, 581). Alternatively, the same transformation may be effected by the use of a suitable catalyst such as palladium in the presence of hydrogen. The reaction is usually conducted at pressures of $10^4$ to $10^7$ kPa in a suitable organic solvent such as, but not limited to, toluene. Elevated temperatures of 80-110° C. are usually required to achieve the transformation. As one skilled in the art will realize, numerous chemical modifications of the thioether moiety are possible, and may be employed when necessary to facilitate this transformation.

Scheme 7

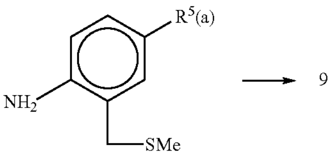

10

Compounds of Formula 10 may be prepared from iminosulfuranes of Formula 11. The transformation may be achieved in a protic solvent such as methanol or water, in a non-protic solvent such as dichloromethane or toluene in the presence of a suitable base such as triethylamine (e.g. Org. Synth. Coll. Vol. VI, 581) or sodium methoxide, or in a combination of a protic solvent, a protic solvent and a base. The temperature at which the reaction is conducted is usually in the range 40-110° C. As one skilled in the art will realize, suitable salts of compounds of Formula 11 such as, but not limited to a hydrochloride, a sulfate or a bisulfate may also be employed, provided that the appropriate amount of base is first used to generate the free base 11. This may be done as a separate step or as an integral part of the step involving the transformation of compounds of Formula 11 to compounds of Formula 10.

Scheme 8

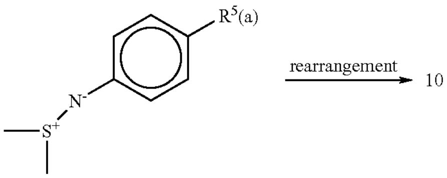

11
or salt

Compounds of Formula 11 may be prepared from anilines of Formula 12 by reaction with dimethyl sulfide and a suitable chlorinating agent such as, but not limited to N-chlorosuccinimide (e.g. Org. Synth. Coll. Vol. VI, 581), chlorine or N-chlorobenzotriazole. Alternatively, anilines of Formula 12 may be treated with dimethyl sulfoxide which has been "activated" by treatment with an agent such as acetic anhydride, trifluoroacetic, anhydride, trifluoromethanesulfonic anhydride, cyclohexylcarbodiimide, sulfur trioxide, or phosphorus pentoxide. The reaction is conducted in a suitable organic solvent such as dichloromethane or dimethyl sulfoxide. The reaction is conducted at a temperature of −70° C. to 25° C. and is dependent on the solvent and reagent used.

Scheme 9

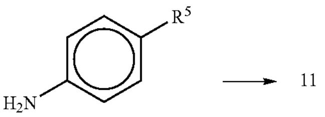

12

Intermediate ortho amino carboxylic acid amides of Formula 2a and 2b may also be prepared from isatoic anhydrides of Formula 13 and 14 (Scheme 10). Typical procedures involve combination of equimolar amounts of the amine 7 with the isatoic anhydride in polar aprotic solvents such as pyridine and dimethylformamide at temperatures ranging from room temperature to 100° C. $R^1$ substituents such as alkyl and substituted alkyl may be introduced by the base catalyzed alkylation of isatoic anhydride 13 with known alkylating reagents $R^1$-Lg (wherein Lg is a leaving group such as halogen, alkyl or aryl suphonates or alkyl sulfates) to provide the alkyl substituted intermediates 14. Isatoic anhydrides of Formula 13 may be made by methods described in Coppola, *Synthesis* 1980, 505 and Fabis et al *Tetrahedron,* 1998, 10789.

-continued

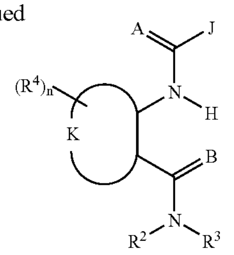

Ic (A is O, B is O, $R^1$ is H)

Scheme 10

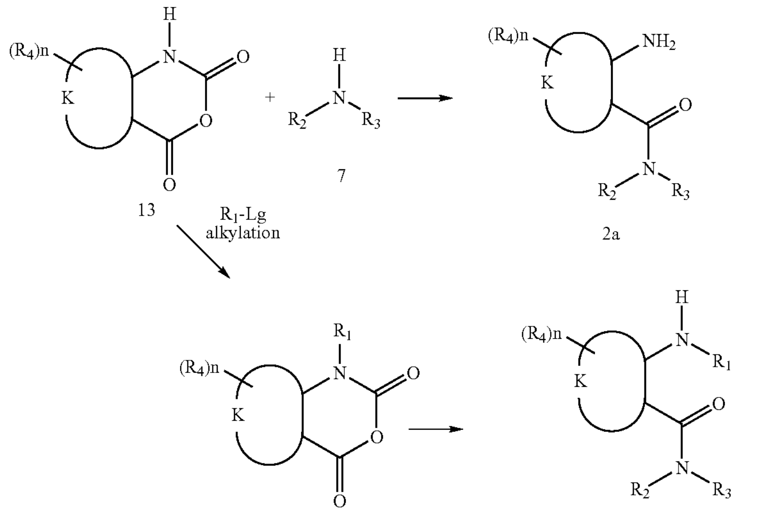

13 7 2a 14 2b ($R_1$ is other than H)

An alternate procedure for the preparation of specific compounds of Formula I (wherein A is O, B is O and $R^1$ is H) involves reaction of an amine 7 with a heterocyclic fused oxazinone of Formula 15. Typical procedures involve combination of the amine with the oxazinone in solvents such as tetrahydrofuran or pyridine at temperatures ranging from room temperature to the reflux temperature of the solvent. Oxazinones are well documented in the chemical literature and are available via known methods that involve the coupling of either an ortho amino carboxylic acid with an acid chloride. For references to the synthesis and chemistry of heterocyclic fused oxazinones see Jakobsen et al, *Biorganic and Medicinal Chemistry,* 2000, 8, 2803-2812 and references cited therein.

Scheme 11

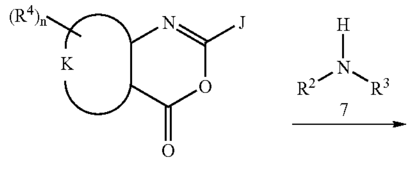

15 7

Heterocyclic acids of Formula 4, wherein J is an optionally substituted heterocycle, can be prepared by procedures outlined in Schemes 12-17. Both general and specific references to a wide variety of heterocyclic acids including thiophenes, furans, pyridines, pyrimidines, triazoles, imidazoles, pyrazoles, thiazoles, oxazoles, isothiazoles, thiadiazoles, oxadiazoles, triazines, pyrazines, pyridazines, and isoxazoles can be found in the following compendia: *Rodd's Chemistry of Chemistry of Carbon Compounds*, Vol. IVa to IVl., S. Coffey editor, Elsevier Scientific Publishing, New York, 1973; *Comprehensive Heterocyclic Chemistry*, Vol. 1-7, A. R. Katritzky and C. W. Rees editors, Pergamon Press, New York, 1984; *Comprehensive Heterocyclic Chemistry II*, Vol. 1-9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. Particularly useful heterocyclic acids of this invention include pyridine acids, pyrimidine acids and pyrazole acids. Procedures for the synthesis of representative examples of each are detailed in Schemes 12-17. A variety of heterocyclic acids and general methods for their synthesis may be found in World Patent Application WO 98/57397.

The synthesis of representative pyridine acids (4b) is depicted in Scheme 12. This procedure involves the known synthesis of pyridines from β-ketoesters and 4-aminobutenones (19). Substituent groups $R^5$(a) and $R^5$(b) include e.g. alkyl and haloalkyl.

Scheme 12

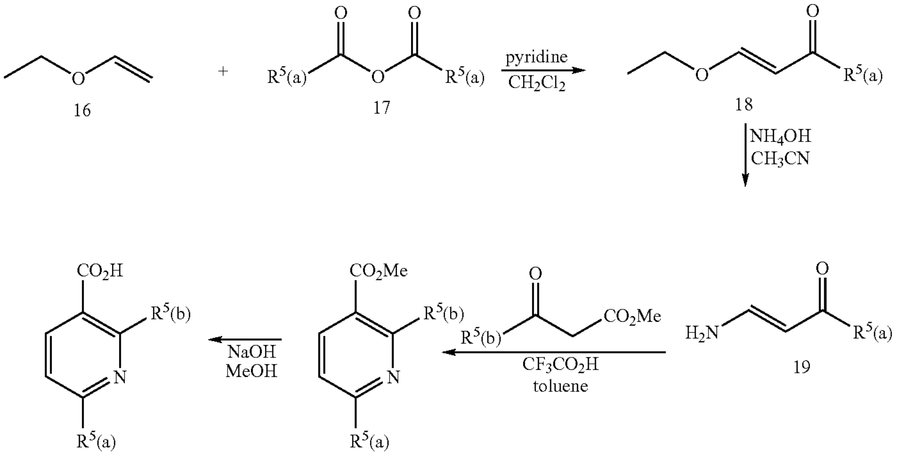

16 17 18 19 20 4a

The synthesis of representative pyrimidine acids (4c) is depicted in Scheme 13. This procedure involves the known synthesis of pyrimidines from vinylidene-β-ketoesters (22) and amidines. Substituent groups $R^5$(a) and $R^5$(b) include e.g. alkyl and haloalkyl.

Scheme 13

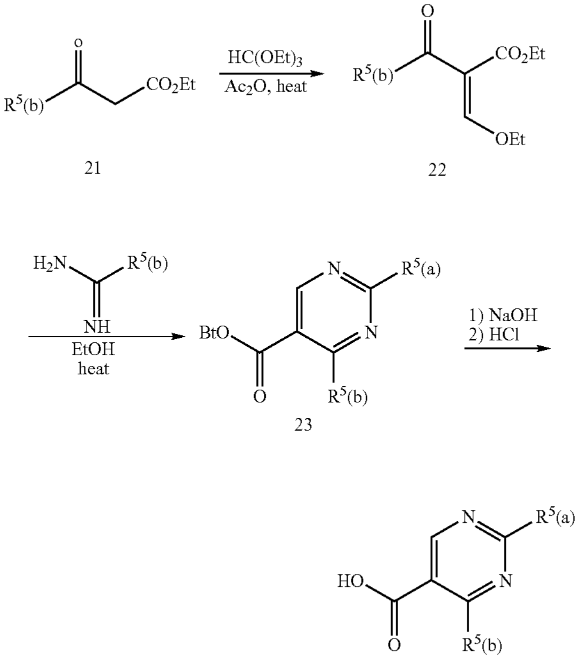

21 22 23 4c

The synthesis of representative pyrazole acids (4d-4g) is depicted in Schemes 14-17. Pyrazoles 4d are described in Scheme 14. The synthesis of Scheme 14 involves as the key step introduction of the $R^5$(b) substituent via alkylation of the pyrazole. The alkylating agent $R^5$(b)-Lg (wherein Lg is a leaving group such as Cl, Br, I, sulfonates such as p-toluenesulfonate or methanesulfonate or sulfates such as —$SO_2OR^7$(b)) includes $R^7$(b) groups such as $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_2$-$C_6$ alkylcarbonyl, $C_2$-$C_6$ alkoxycarbonyl, $C_3$-$C_8$ dialkylaminocarbonyl, $C_3$-$C_6$ trialkylsilyl; or phenyl, benzyl, benzoyl, 5- or 6-membered heteroaromatic ring or an aromatic 8-, 9- or 10-membered fused heterobicyclic ring system, each ring or ring system optionally substituted. Oxidation of the methyl group affords the pyrazole carboxylic acid. Some of the more preferred $R^5$(a) groups include haloalkyl.

Scheme 14

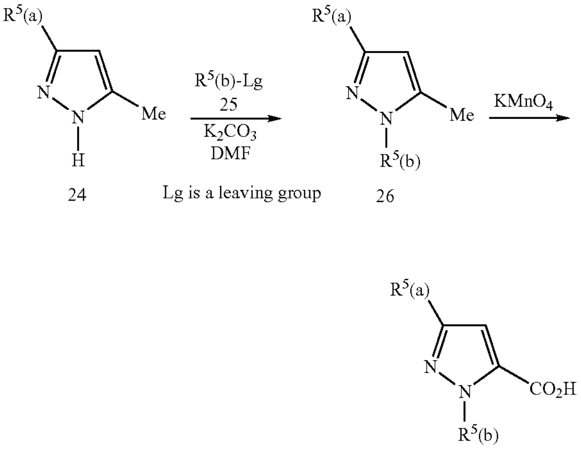

24 26 4d

Pyrazoles 4e are described in Scheme 15. These pyrazole acids may be prepared via metallation and carboxylation of pyrazoles of formula 28 as the key step. The $R^5$(b) group is introduced in a manner similar to that of Scheme 14, i.e. via alkylation with a $R^5$(b) alkylating agent. Representative $R^5$(a) groups include e.g. cyano, and haloalkyl.

Scheme 15

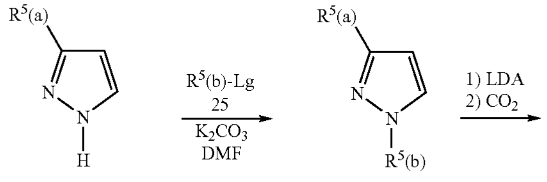

27 Lg is a leaving group 28

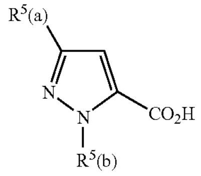

4e

Pyrazoles 4f are described in Scheme 16. These can be prepared via reaction of an optionally substituted phenyl hydrazine 29 with a pyruvate 30 to yield pyrazole esters 31. Hydrolysis of the ester affords the pyrazole acids 4f. This procedure is particularly useful for the preparation of compounds where $R^5$(b) is optionally substituted phenyl and $R^5$(a) is haloalkyl.

Scheme 16

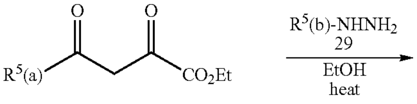

30

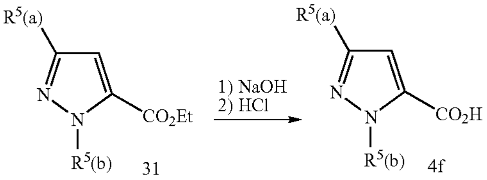

31 4f

Pyrazoles acids of Formula 4g are described in Scheme 17. These can be prepared via 3+2 cycloaddition of an appropriately substituted nitrilimine (32) with either substituted propiolates (33) or acrylates (36). Cycloaddition with acrylates requires additional oxidation of the intermediate pyrazoline to the pyrazole. Hydrolysis of the ester affords the pyrazole acids 4g. Preferred iminohalides for this reaction include the trifluoromethyl iminochloride (38) and the iminodibromide (39). Compounds such as 38 are known (*J. Heterocycl. Chem.* 1985, 22(2), 565-8). Compounds such as 39 are available by known methods (*Tetrahedron Letters* 1999, 40, 2605). These procedures are particularly useful for the preparation of compounds where $R^5$(b) is optionally substituted phenyl and $R^5$(a) is haloalkyl or bromo.

Scheme 17

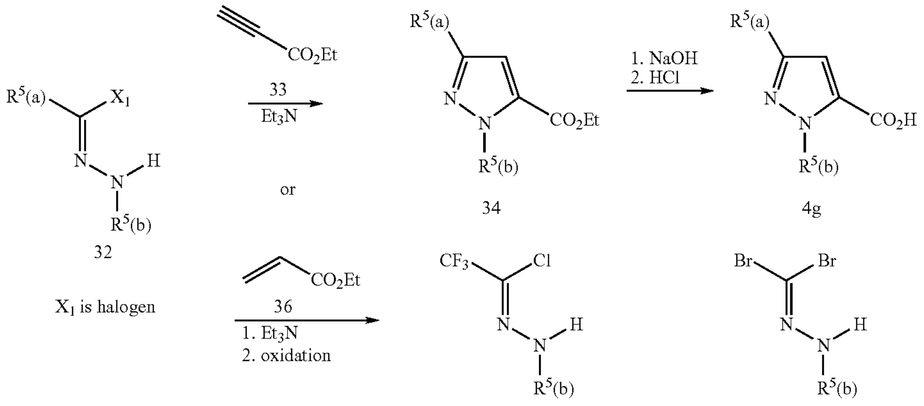

32

X1 is halogen or

34

4g

38

39

Ortho-amino carboxylic acid esters of Formula 5 wherein $R^1$ is H can be prepared from monoesters of ortho dicarboxylic acids of Formula 40 via rearrangement of the corresponding acyl azide and hydrolysis of the resulting isocyanate (or alternatively by trapping of the isocyanate with an alcohol and cleaving of the resulting carbamate) as shown in Scheme 18.

Scheme 18

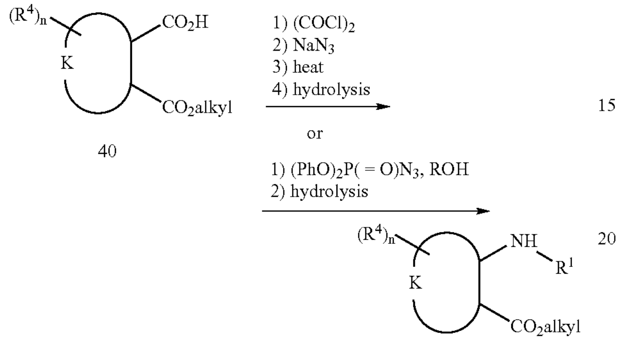

40

5 ($R^1$ is H)

Alternatively ortho-amino carboxylic acid esters of Formula 5 can be prepared from ortho carboxamide carboxylic esters of Formula 41 by Hoffman rearrangement with reagents such as sodium hydroxide and bromine as shown in Scheme 19.

Scheme 19

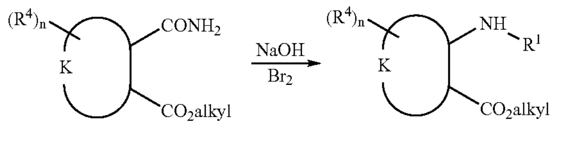

41

5 ($R^1$ is H)

Compounds of Formulae 40 and41 are known in the art or can be readily prepared from compounds known in the art. (For example, see *Tetrahedron,* 1997, 53, 14497; *J. Chem. Soc., Perkin Trans.* 1, 1996, 10, 1035; WO92/08724 and EP 418667).

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1H$ NMR spectra are reported in ppm downfield from tetramethylsilane; s is singlet, d is doublet, t is triplet, q is quartet, m is multiplet, dd is doublet of doublets, dt is doublet of triplets, brs is broad singlet.

EXAMPLE 1

Preparation of 5-methyl-N-(1-methylethyl)-4-[[4-trifluoromethoxy)benzoyl]amino]-3-pyridinecarboxamide Step A: Preparation of ethyl 4-azido-5-methyl-3-pyridinecarboxylate A slurry of 14.1 g (78 mmol) of ethyl 1,4-dihydro-5-methyl-4oxo-3-pyridinecarboxylate (prepared according to Horvath, G.; Dvortsak, P. *J. Heterocycl. Chem.* 1980, 359) in 30 mL of phosphorous oxychloride was refluxed for 1 hour. After cooling, the volatiles were removed with a rotary evaporator. The residue was poured into cold saturated aqueous sodium bicarbonate. Dichloromethane was added and the mixture was filtered through celite. The layers were separated. The organic layer was dried (sodium sulfate) and the solvent was removed with a rotary evaporator. The residue was dissolved in 150 mL of dimethylformamide. 15.2 g (234 mmol) of sodium azide was added. The mixture was heated at 95° C. for 1 hour. After cooling, the solvent was removed with a rotary evaporator. The residue was partitioned between ethyl acetate and water. The organic layer was dried (sodium sulfate) and the solvent was removed with a rotary evaporator. The residue was passed through a plug of silica gel with 25% ethyl acetate in hexanes as eluant to afford 11.9 g of the title compound as a cream colored solid.

$^1H$ NMR ($CDCl_3$) δ 1.41 (t, 3H), 2.12 (s, 3H), 4.36 (q, 2H), 8.12 (s, 1H), 8.83 (s, 1H).

Step B: Preparation of ethyl 4-amino-5-methyl-3-pyridinecarboxylate 0.50 g of material prepared in Step A was dissolved in 15 mL of ethanol. 0.15 g of 10% palladium on carbon was added. The reaction mixture was placed under one atmosphere of hydrogen for 2 hours. The catalyst was removed by filtration. The solvent was removed with a rotary evaporator to afford 0.43 g of the title compound as a white solid.

$^1H$ NMR ($CDCl_3$) δ 1.42 (t, 3H), 2.30 (s, 3H), 4.45 (q, 2H), 8.47 (s, 1H), 8.87 (s, 1H).

Step C: Preparation of ethyl 5-methyl-4-[[4-trifluoromethoxy)benzoyl]amino]-3-pyridinecarboxylate 1.0 g (5.6 mmol) of material prepared in Step B was dissolved in 30 mL of dichloromethane. 0.77 mL (5.6 mmol) of triethylamine, a catalytic amount of 4-dimethylaminopyridine and 0.88 mL (5.6 mmol) of 4-(trifluoromethoxy)benzoyl chloride were added. The mixture was stirred overnight. The reaction mixture was washed with water. The organic layer was dried (sodium sulfate) and the solvent was removed with a rotary evaporator. The residue was purified by medium-pressure liquid chromatography (MPLC) with a gradient of 15-100% ethyl acetate in hexanes as eluant. The bisacylation product eluted first, then 0.42 g of the title compound as white solid. Starting material (0.52 g) was also recovered.

$^1$H NMR ($CDCl_3$) δ 1.41 (t, 3H), 2.32 (s, 3H), 4.39 (q, 2H), 7.37 (d, 2H), 8.08 (d, 2H), 8.63 (brs, 1H), 9.04 (brs, 1H), 10.78 (brs, 1H).

Step D: Preparation of 5-methyl-N-(1-methylethyl)-4-[[4-trifluoromethoxy)benzoyl]amino]-3-pyridinecarboxamide To a solution of 0.049 mL (0.57 mmol) of isopropylamine in 20 mL of dichloroethane at 0° C. was added 0.64 mL (1.3 mmol) of a 2M solution of trimethylaluminum in toluene dropwise. A solution of 0.21 g (0.57 mmol) of the material prepared in Step C in 5 mL of dichloroethane was added dropwise. Four days later an additional 0.049 mL of isopropylamine and 0.64 mL of trimethylaluminum were added. The reaction was refluxed for 6 h. After cooling 20 mL of 1 N HCl was added. The layers were separated. The aqueous layer was made basic with a saturated sodium bicarbonate solution. Dichloromethane was added and the mixture was filtered through celite. The dichloromethane was separated, combined with the dichloroethane layer from above and dried (sodium sulfate). The solvent was removed with a rotary evaporator. The residue was purified by MPLC with a gradient of 25-50% ethyl acetate in hexanes as eluant to afford 0.047 g of the title compound, a compound of the invention, as a white solid; m.p. 202-204° C.

$^1$H NMR ($CDCl_3$) δ 1.27 (d, 6H), 2.33 (s, 3H), 4.23 (m, 1H), 6.46 (br, 1H), 7.35 (d, 2H), 8.07 (d, 2H), 8.56 (brs, 1H), 8.69 (brs, 1H), 11.15 (brs, 1H).

EXAMPLE 2

Preparation of 1-methyl-N-(1-methylethyl)-5-[[4-trifluoromethoxy)benzoyl]amino]-1H-pyrazole-4-carboxamide Step A: Preparation of 5-amino-1-methyl-N-(1-methylethyl)-1H-pyrazole-4-carboxamide 1.0 g (8.0 mmol) of 2-cyano-N-(1-methylethyl)acetamide (prepared according to the procedure of Cheikh et al *J. Org. Chem.,* 1991, 56, 970) was combined with 3.1 mL of triethylorthoformate, 5 mL of acetic anhydride and 0.01 g of anhydrous zinc chloride. The mixture was refluxed for 1 hour. A distillation head was placed on the flask and the reaction was heated at 120° C. for 8 hours. After standing for two days the mixture was heated again for 12 hours at 120° C. for 12 hours. The volatiles were removed with a rotary evaporator. Ethanol was added and the volatiles were again removed with a rotary evaporator. This material was dissolved in 15 mL of ethanol. 0.34 mL (6.4 mmol) of methyl hydrazine was added. The reaction mixture was refluxed for 5 hours and then allowed to stand at room temperature overnight. The solvent was removed with a rotary evaporator. The residue was purified by MPLC (ethyl acetate as eluant) to afford 0.14 g of the title compound as a solid.

$^1$H NMR ($CDCl_3$) δ 1.23 (d, 6H), 3.61 (s, 3H), 4.21 (m, 1H), 5.17 (br, 2H), 5.34 (br, 1H), 7.38 (s, 1H).

Step B: Preparation of 1-methyl-N-(1-methylethyl)-5-[[4-trifluoromethoxy)benzoyl]amino]-1H-pyrazole-4-carboxamide 0.14 g (0.77 mmol) of the material from Step A was dissolved in 20 mL of tetrahydrofuran and 0.12 mL (0.85 mmol) of triethylamine and 0.12 mL (0.77 mmol) of 4-(trifluoromethoxy)benzoyl chloride were added. Three days later 0.12 mL (0.85 mmol) of triethylamine and 0.12 mL (0.77 mmol) of 4-(trifluoromethoxy)benzoyl chloride were added. The reaction mixture was refluxed for two days. After cooling the reaction mixture was partitioned between ethyl acetate and water. The organic layer was dried (sodium sulfate) and the solvent was removed with a rotary evaporator. The residue was purified by MPLC with 50% ethyl acetate in hexanes as eluant to afford 0.18 g of the tidle compound, a compound of the invention, as a white solid; m.p. 68-75° C.

$^1$H NMR ($CDCl_3$) δ 1.22 (d, 6H), 3.91 (s, 3H), 4.14 (m, 1H), 5.92 (brd, 1H), 7.32 (d, 2H), 7.62 (s, 1H), 8.08 (d, 2H), 10.78 (brs, 1H).

EXAMPLE 3

Preparation of 4-methyl-N-(1-methylethyl)-3-[[4-trifluoromethyl)benzoyl]amino]-2-thiophenecarboxamide Step A: Preparation of 7-methyl-2H-thieno[3,2-d][1,3]oxazine-2,4(1H)-dione Phosgene in toluene (4.4 g, 20%, 8.88 mmol) was added to the sodium salt of 3-amino-4-methyl-thiophene-2-carbocyclic acid (1 g, 5.58 mmol) in water (17 mL) at 0 C. The mixture was allowed to warm to room temperature and was stirred for 1 hour. The mixture was filtered. After drying in vacuum the product was obtained as a solid 0.49 g (47%).

IR (Nujol®) 1785, 1696, 1580, 1513, 1236, 988, 918, 848, 826 cm-1.

$^1$H NMR (DMSO-$d_6$) δ 2.20 (s, 3H), 7.88 (s, 1H).

Step B: Preparation of 7-methyl-2-[4-(trifluoromethyl)phenyl]-4H-thieno[3,2-d][1,3]oxazin-4-one 4-(Dimethylamino)pyridine (0.66 g, 5.41 mmol) was added to the product from Step A in dioxane (10 mL). 4-(Trifluoromethyl)benzoyl chloride (1.13 g, 5.42 mmol) was added to the mixture and the mixture was boiled for approximately 3 hours. The mixture was allowed to cool to room temperature and was poured into hydrochloric acid (100 mL, 1 N). The mixture was extracted with ethyl acetate (3×50 mL) and the combined extracts were dried and evaporated. Chromatography on silicon gel (eluted with ethyl acetate/hexanes) gave the product as a white solid 1.56 g, (91.7%).

IR (Nujol®) 2923, 1763, 1600, 1572, 1410, 1312, 1234, 1170, 1125, 1068, 1013, 978, 934, 851, 813 cm-1.

$^1$H NMR ($CDCl_3$) δ 2.47 (s, 3H), 7.60 (s, 1H), 7.77 (d, 2H), 8.45(d, 2H).

Step C: Preparation of 4-methyl-N-(1-methylethyl)-3-[[4-trifluoromethyl)benzoyl]amino]-2-thiophenecarboxamide A mixture of the product from Step B (0.2 g, 0.043 mmol) and isopropylamine (0.2 g, 3.39 mmol) in THF (5 mL) was stirred for 6 hours. The solvent was removed under reduced pressure to give the product, a compound of the invention, as a solid 0.21 g, (91%).

IR (Nujol®) 3294, 1664, 1625, 1573, 1524, 1409, 1327, 1207, 1167 1126, 1068, 1018, 954, 885, 857 cm-1.

$^1$H NMR ($CDCl_3$) δ 1.22 (d, 6H), 2.30 (s, 3H), 4.22-4.11 (m, 1H), 5.58 (d, 1H), 7.03 (s, 1H), 7.75 (d, 2H), 8.13 (d, 2H), 10.63 (5,1H).

EXAMPLE 4

Preparation of 5-[[[3-Chloro-1-(3-chloro-2-pyridinyl)-1H-pyrazol-5-yl]carbonyl]amino]-N,6-dimethyl-4-pyrimidinecarboxamide Step A: Preparation of 1-(1,1-dimethylethyl 4-ethyl-2-acetyl-3-amino-2-butenedioate To a mixture of 17.15 g (108 mmol) of t-butyl acetoacetate and 12.8 mL (130 mmol) of ethyl cyanoformate in 25 mL of dichloromethane was added 1.64 g of zinc acetylacetonate hydrate. After stirring overnight the volatiles were removed with a rotary evaporator. The residue was dissolved in ethyl acetate and filtered through celite. The solvent was removed with a rotary evaporator to afford 29.9 g of the title compound as a white solid as an E/Z isomer mixture.

$^1$H NMR ($CDCl_3$) δ 1.33 (t, 3H), 1.52 (s, 9H), 2.35 (s, 3H) [minor isomer 2.40 (s, 3H)], 4.33 (m, 2H).

Step B: Preparation of 5-(1,1-dimethylethyl) hydrogen 6-methyl-4,5-pyrimidinedicarboxylate To a solution of 11.6 g (45 mmol) of the material from Step A in 55 mL of ethanol was added 10.9 g (135 mmol) of formamidine hydrochloride. The reaction mixture was cooled in an ice bath and 17 mL (135 mmol) of 1,1,3,3-tetramethylguanidine was added dropwise. After the mixture was stirred overnight the solvent was removed with a rotary evaporator. The residue was partitioned between ethyl acetate and water. The aqueous layer was cooled in an ice bath, acidified with concentrated HCl and extracted three times with ethyl acetate. The organic layer was dried (sodium sulfate) and the solvent was removed with a rotary evaporator to afford 9.12 g of the title compound as a yellow solid.

$^1$H NMR ($CDCl_3$) δ 1.65 (s, 9H), 2.68 (s, 3H), 9.19 (s, 1H).

Step C: Preparation of 5-(1,1-dimethylethyl) 4-methyl 6-methyl-4,5-pyrimidinedicarboxylate To a solution of 9.12 g (38 mmol) of the material from Step B in 100 mL of N,N-dimethyl formamide (DMF) was added 3.1 mL (50 mmol) of iodomethane and 3.7 g (50 mmol) of lithium carbonate. The reaction mixture was heated at 60° C. for 3 hours. After cooling the reaction mixture was partitioned between dichloromethane and water. The organic layer was dried (sodium sulfate) and the solvent was removed with a rotary evaporator and then a vacuum pump. The residue was purified by MPLC with a gradient of 20-30% ethyl acetate in hexanes as eluant to afford 7.58 g of the title compound as an off-white solid.

$^1$H NMR ($CDCl_3$) δ 1.63 (s, 9H), 2.67 (s, 3H), 4.01 (s, 3H), 9.19 (s, 1H).

Step D: Preparation of methyl 5-[[(1,1-dimethylethoxy)carbonyl]amino]-6-methyl-4-pyrimidinecarboxamide 7.55 g of the material from Step C was dissolved in 40 mL of dichloromethane. 20 mL of trifluoroacetic acid was added. After two days the reaction mixture was refluxed for 6 hours. After an additional day the volatiles were removed with a rotary evaporator. Toluene was added and the solvent was removed with a rotary evaporator. This material (9.2 g) was dissolved in 100 mL of t-butanol. 9.2 mL (66 mmol) of triethylamine and 14 mL (66 mmol) of diphenylphosphoryl azide were added. The reaction was refluxed 3 hours. After cooling, the solvent was removed with a rotary evaporator. The residue was partitioned between ethyl acetate and water. The organic layer was dried (sodium sulfate) and the solvent was removed with a rotary evaporator. The residue was purified by MPLC with a gradient of 40-100% ethyl acetate in hexanes as eluant to afford 5.81 g of the title compound as a yellow solid.

$^1$H NMR ($CDCl_3$) δ 1.52 (s, 9H), 2.60 (s, 3H), 4.03 (s, 3H), 8.07 (br, 1H),8.98 (s, 1H).

Step E: Preparation of methyl 5-amino-6-methyl-4-pyrimidinecarboxylate 5.8 g of the material from Step D was dissolved in 25 mL of trifluoroacetic acid. After stirring for 90 minutes the solvent was removed with a rotary evaporator. Saturated aqueous sodium bicarbonate was added. The aqueous layer was extracted five times with dichloromethane. The organic layer was dried (sodium sulfate) and the solvent was removed with a rotary evaporator to afford 3.78 g of the title compound with a small amount of an impurity.

$^1$H NMR ($CDCl_3$) δ 2.50 (s, 3H), 4.00 (s, 3H), 5.76 (br, 2H),8.56 (s, 1H).

Step F: Preparation of 5-amino-6-methyl-4-pyrimidinecarboxylic acid monosodium salt 2.0 g (12 mmol) of the material from Step E was dissolved in 24 mL of methanol. 12 mL of 1N solution of sodium hydroxide was added. After 1 hour the solvent was removed with a rotary evaporator. The residue was dried in a vacuum oven overnight to afford 2.39 g of the title compound as a tan solid.

$^1$H NMR ($D_2O$) δ 2.45 (s, 3H), 8.37 (s, 1H).

Step G: Preparation of 3-chloro-N,N-dimethyl-1H-pyrazole-1-sulfonamide

To a solution of N-dimethylsulfamoylpyrazole (188.0 g, 1.07 mol) in dry tetrahydrofuran (1500 mL) at −78° C. was added dropwise a solution of 2.5 M n-butyl-lithium (472 mL, 1.18 mol) in hexane while maintaining the temperature below −65° C. Upon completion of the addition the reaction mixture was maintained at −78° C. for an additional 45 minutes, after which time a solution of hexachloroethane (279 g, 1.18 mol) in tetrahydrofuran (120 mL) was added dropwise. The reaction mixture was maintained for an hour at −78° C., warmed to −20° C. and then quenched with water (1 L). The reaction mixture was extracted with methylene chloride (4×500 mL); the organic extracts were dried over magnesium sulfate and concentrated. The crude product was further purified by chromatography on silica gel using methylene chloride as eluent to afford the title product compound as a yellow oil (160 g).

$^1$H NMR ($CDCl_3$) δ 3.07 (d, 6H), 6.33 (s, 1H), 7.61 (s, 1H).

Step H: Preparation of 3-chloropyrazole

To trifluoroacetic acid (290 mL) was added dropwise the chloropyrazole product (160 g) from Step G, and the reaction mixture was stirred at room temperature for 1.5 hours and then concentrated at reduced pressure. The residue was taken up in hexane, insoluble solids were filtered off, and the hexane was concentrated to afford the crude product as an oil. The crude product was further purified by chromatography on silica gel using ether/hexane (40:60) as eluent to afford the title product as a yellow oil (64.44 g).

$^1$H NMR ($CDCl_3$) δ 6.39 (s, 1H), 7.66 (s, 1H), 9.6 (br s, 1H).

Step I: Preparation of 3-chloro-2-(3-chloro-1H-pyrazol-1-yl)pyridine

To a mixture of 2,3-dichloropyridine (92.60 g, 0.629 mol) and 3-chloropyrazole (64.44 g, 0.629 mol) in N,N-dimethylformamide (400 mL) was added potassium carbonate (147.78 g, 1.06 mol), and the reaction mixture was then heated to 100° C. for 36 hours. The reaction mixture was cooled to room temperature and slowly poured into ice water. The precipitated solids were filtered and washed with water. The solid filter cake was taken up in ethyl acetate, dried over magnesium sulfate and concentrated. The crude solid was chromatographed on silica gel using 20% ethyl acetate/hexane as eluent to afford the title product as a white solid (39.75 g).

$^1$H NMR ($CDCl_3$) δ 6.43 (s, 1H), 7.26 (m, 1H), 7.90 (d, 1H), 8.09 (s, 1H), 8.41 (d, 11H).

Step J: Preparation of 3-chloro-1-(3-chloro-2-pyridinyl)-1H-pyrazole-5-carboxylic acid To a solution of the pyrazole product from Step I (39.75 g, 186 mmol) in dry tetrahydrofuran (400 mL) at −78° C. was added dropwise a solution of 2.0 M lithium diisopropylamide (93 mL, 186 mmol) in tetrahydrofuran. Carbon dioxide was bubbled through the amber solution for 14 minutes, after which time the solution became pale brownish-yellow. The reaction was made basic with 1N aqueous sodium hydroxide solution and extracted with ether (2×500 mL). The aqueous extracts were acidified with 6N hydrochloric acid and extracted with ethyl acetate (3×500 mL). The ethyl acetate extracts were dried over magnesium sulfate and concentrated to afford the title product as an off-white white solid (42.96 g). (Product from another run following similar procedure melted at 198-199° C.)

$^1$H NMR (DMSO-$d_6$) δ 6.99 (s, 1H), 7.45 (m, 1H), 7.93 (d, 1H), 8.51 (d, 1H).

Step K: Preparation of 2-[3-chloro-1-(3-chloro-2-pyridinyl)-1H-pyridinyl)-1H-pyrazol-5-yl]-8-methyl-4H-pyrimido[5,4-d][1,3]oxazin-4-one To a solution of 0.26 mL (3.3 mmol) of methanesulfonyl chloride in 18 mL of acetonitrile at 0° C. was added 0.77 g (3.0 mmol) of 3-chloro-1-(3-chloro-2-pyridinyl)-1H-pyrazol-5-carboxylic acid from Step J. 0.42 mL (3.0 mmol) of triethylamine in 9 mL of acetonitrile was added dropwise. After 20 minutes at 0° C., 0.525 g (3.0 mmol) of material from Step F was added. After 15 minutes 0.42 mL (3.0 mmol) of triethylamine was added dropwise. After 2 hours 0.26 mL (3.3 mmol) of methanesulfonyl chloride was added. After stirring overnight. The reaction mixture was poured into water. Filtration afforded 0.27 g of the title compound.

$^1$H NMR ($CDCl_3$) δ 2.20 (s, 3H), 7.23 (s, 1H), 7.54(dd, 1H), 8.01 (dd, 1H), 8.57(dd, 1H), 9.20 (s, 1H).

Step L: Preparation of 5-[[[3-Chloro-1-(3-chloro-2-pyridinyl)-1H-pyrazol-5-yl]carbonyl]amino]-N,6-dimethyl-4-pyrimidinecarboxamide 2 mL of a 2M solution of methylamine in tetrahydrofuran was added to 0.090 g of material from Step K. After stirring overnight the solvent was removed with a rotary evaporator to afford 0.071 g of the title compound, a compound of the invention, as a tan solid; m.p. 205-207° C.

$^1$H NMR ($CDCl_3$) δ 2.48 (s, 3H), 3.04 (d, 3H), 7.06 (s, 1H), 7.41(dd, 1H), 7.89 (dd, 1H), 8.30 (br, 1H), 8.48 (dd, 1H), 8.85 (s, 1H), 11.57 (br, 1H).

EXAMPLE 5

Preparation of 2,6-dichloro-3-[[[1-(3-chloro-2-pyridinyl)-3-(trifluoromethyl)-1H-pyrazol-5-yl ]carbonyl]amino]-N-(1-methylethyl)-4-pyridinecarboxamide Step A: Preparation of ethyl 3-amino-4-pyridinecarboxylate To a solution of 1 g (7.25 mmol) of 3-amino-4-pyridinecarboxylic acid in 5 mL of ethyl alcohol was added 2 mL of sulfuric acid. The mixture was warmed under reflux for 2 h. It was cooled and basified with conc. $NH_4OH$ solution to pH=8. The resulting solution was extracted with ethyl acetate and the organic layer was washed with brine and water, dried ($MgSO_4$) and concentrated in vacuo to give 1.04 g of the title compound as a white solid (87%).

$^1$H NMR ($CDCl_3$) δ 8.19 (s 1H), 7.93 (d 1H, J is 5.1 Hz), 7.60 (d, 1H, J is 5.1 Hz), 5.67 (br s, 2H), 4.36 (q, 2H), 1.40 (t, 3H).

Step B: Preparation of ethyl 3-amino-2,6-dichloro-4-pyridinecarboxylate

To a solution of 1.04 g (6.27 mmol) of ethyl 3-amino-4-pyridinecarboxylate in 5 mL of DMF was added 1.67 g of N-chlorosuccinimide (12.5 mmol) in a single portion at room temperature. The mixture was then stirred at the same temperature for 24 hours. The resulting mixture was concentrated in vacuo and purified by silica gel column to give 1.40 g of the title compound as a white solid (95%).

$^1$H NMR ($CDCl_3$) δ 7.67 (s 1H), 6.18 (br s, 2H), 4.39 (q, 2H), 1.42 (t, 3H).

Step C: Preparation of 3-amino-2,6-dichloro-4-pyridinecarboxylic monopotassium salt To a solution of 1.30 g (5.54 mmol) of ethyl 3-amino-2,6-dichloro-4-pyridinecarboxylate in a mixture of 5 mL of water and 20 mL of ethyl alcohol was added 622 mg (11.1 mmol) of potassium hydroxide at room temperature and the reaction mixture was warmed at 90° C. for 1 hour. The mixture was then concentrated in vacuo and evaporated with benzene three times to give 1.63 g of the title compound as a white solid. The crude product was used in the next reaction without any further purification (98%).

$^1$H NMR (DMSOd-$_6$) δ 7.31 (s, 1H), 7.14 (br s, 2H).

Step D: Preparation of 6,8-dichloro-2H-pyrido[3,4-d][1,3]oxazine-2,4(1H)-dione

To a solution of 1.64 g (5.54 mmol) of the material from Step C in 20 mL of dioxane was added 2.2 g (11.1 mmol) of diphosgene at 0° C. The mixture was allowed to warm to room temperature and stirred for 24 hours. The mixture was then concentrated in vacuo to give 1.70 g of the title compound as a white solid (quantitative).

1H NMR (DMSOd-$_6$) δ 7.99 (s, 1H).

Step E: Preparation of 3-chloro-2-[3-(trifluoromethyl)-1H-pyrazol-1-yl]pyridine

To a mixture of 2,3-dichloropyridine (99.0 g, 0.67 mol) and 3-trifluoromethyl pyrazole (83 g, 0.61 mol) in dry N,N-dimethylformamide (300 mL) was added potassium carbonate (166.0 g, 1.2 mol) and the reaction was then heated to 110-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded the desired intermediate as a clear yellow oil (113.4 g).

$^1$H NMR ($CDCl_3$) δ 6.78 (s, 1H), 7.36 (t, 1H), 7.93 (d, 1H), 8.15 (s, 1H), 8.45 (d, 1H).

Step F: Preparation of 1-(3-chloro-2-pyridinyl)-3-(trifluoromethyl)-1H-pyrazole-5-carboxylic acid To a solution of the pyrazole product from Step E (105.0 g, 425 mmol) in dry tetrahydrofuran (700 mL) at −75° C. was added via cannula a −30° C. solution of lithium diisopropylamide (425 mmol) in dry tetrahydrofuran (300 mL). The deep red solution was stirred for 15 minutes, after which time carbon dioxide was bubbled through at −63° C. until the solution became pale yellow and the exothermicity ceased. The reaction was stirred for an additional 20 minutes and then quenched with water (20 mL). The solvent was removed under reduced pressure, and the reaction mixture partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously and additional acid was added to lower the pH to 2.5-3. The orange oil congealed into a granular solid, which was filtered, washed successively with water and 1N hydrochloric acid, and dried under vacuum at 50° C. to afford the title product as an off-white solid (130 g). (Product from another run following similar procedure melted at 175-176° C.)

$^1$H NMR (DMSO-$d_6$) δ 7.61 (s, 1H), 7.76 (dd, 1H), 8.31 (d, 1H), 8.60 (d, 1H).

Step G: Preparation of 2,6-dichloro-3-[[[1-(3-chloro-2-pyridinyl)-3-(trifluoromethyl)-1H-pyrazol-5-yl]carbonyl]amino]-N-(1-methylethyl)-4-pyridinecarboxamide To a solution of 268 mg (0.92 mmol) of 1-(3-chloro-2-pyridinyl)-3-(trifluoromethyl)-1H-pyrazole-5-carboxylic acid (from Step F) in 5 mL of dichloromethane was added 160 μL (1.84 mmol) of oxalyl chloride and two drops of DMF in sequence at room temperature. The mixture was then stirred at the same temperature for 1 hour. The crude mixture was then concentrated in vacuo. The resulting mixture was dissolved with 5 mL of acetonitrile followed by additions of 280 mg (0.92 mmol) of the compound prepared in Step D and 298 μL (3.68 mmol) of pyridine in sequence. The reaction mixture was warmed to 70° C. for 2 hours and allowed to cool to room temperature. A solution of 157 μL (1.84 mmol) of isopropylamine in 1 mL of acetonitrile was added to the mixture and it was warmed to 60° C. for 1 hour. The reaction was allowed to cool to room temperature and quenched with water. The aqueous layer was extracted with ethyl acetate and the organic layer was dried with $MgSO_4$ and concentrated in vacuo. The resulting mixture was purified with a silica gel column to give 250 mg of the title compound, a compound of the invention, as a white solid (52%). m.p. 240-242° C.

$^1$H NMR ($CDCl_3$) δ 9.85 (s, 1H), 8.53 (dd, 1H), 7.90 (dd, 1H), 7.56 (s, 1H), 7.42 (dd, 1H), 7.22 (s, 1H), 6.08 (br d, 1H), 4.13 (m, 1H), 1.14 (d, 6H).

By the procedures described herein together with methods known in the art, the following compounds of Tables 1 to 32 can be prepared. The following abbreviations are used in the Tables: t is tertiary, s is secondary, n is normal, i is iso, c is cyclo, Me is methyl, Et is ethyl, Pr is propyl, i-Pr is isopropyl, t-Bu is tertiary butyl, Ph is phenyl, OMe is methoxy, OEt is ethoxy, SMe is methylthio, SEt is ethylthio, CN is cyano, $NO_2$ is nitro, TMS is trimethylsilyl, S(O)Me is methylsulfinyl, and $S(O)_2Me$ is methylsulfonyl. Structures of K for Tables 15, 16 and 17 can be found in Exhibit 2.

TABLE 1

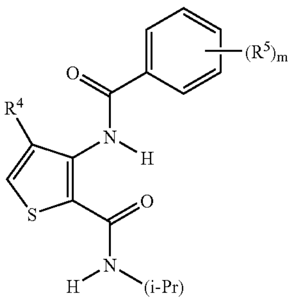

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |

TABLE 1-continued

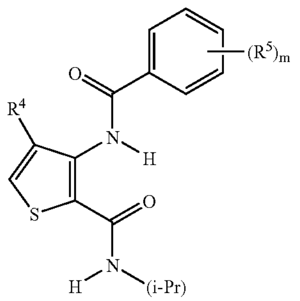

| $R^4$ | $(R^5)_m$ | $R^4$ | $(R^5)_m$ | $R^4$ | $(R^5)_m$ |
|---|---|---|---|---|---|
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |

TABLE 1-continued

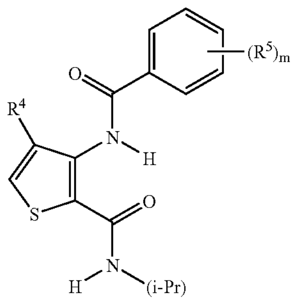

| $R^4$ | $(R^5)_m$ | $R^4$ | $(R^5)_m$ | $R^4$ | $(R^5)_m$ |
|---|---|---|---|---|---|
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 2

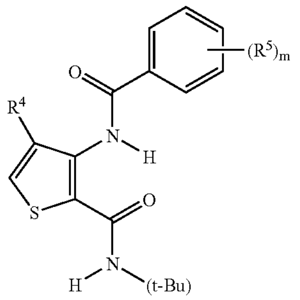

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |

TABLE 2-continued

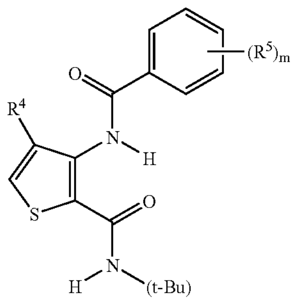

| $R^4$ | $(R^5)_m$ | $R^4$ | $(R^5)_m$ | $R^4$ | $(R^5)_m$ |
|---|---|---|---|---|---|
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |

TABLE 2-continued

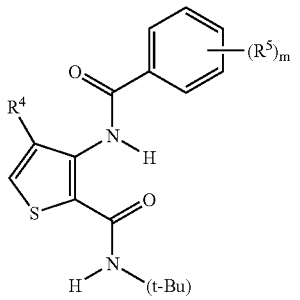

| $R^4$ | $(R^5)_m$ | $R^4$ | $(R^5)_m$ | $R^4$ | $(R^5)_m$ |
|---|---|---|---|---|---|
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 3

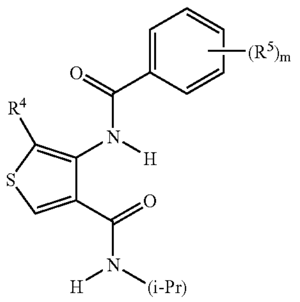

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |

TABLE 3-continued

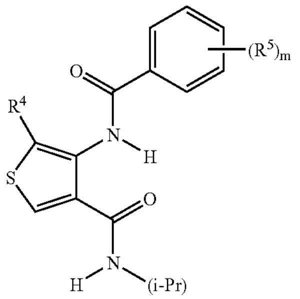

| $R^4$ | $(R^5)_m$ | $R^4$ | $(R^5)_m$ | $R^4$ | $(R^5)_m$ |
|---|---|---|---|---|---|
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 4

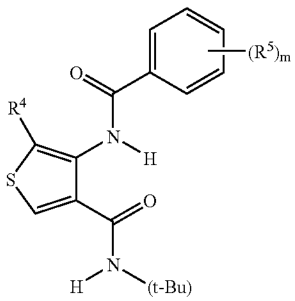

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |

TABLE 4-continued

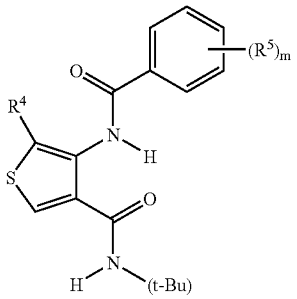

| $R^4$ | $(R^5)_m$ | $R^4$ | $(R^5)_m$ | $R^4$ | $(R^5)_m$ |
|---|---|---|---|---|---|
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 5

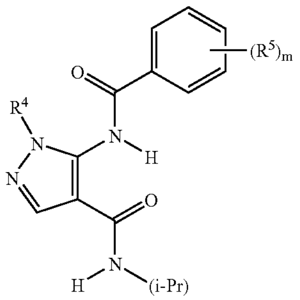

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| $CF_3$ | 2-Me-4-$CF_3$ | $CF_2H$ | 2-Me-4-$CF_3$ | $CH_2CF_3$ | 2-Me-4-$CF_3$ |
| $CF_3$ | 2-Me-4-$OCF_3$ | $CF_2H$ | 2-Me-4-$OCF_3$ | $CH_2CF_3$ | 2-Me-4-$OCF_3$ |
| $CF_3$ | 2-Me-4-$OCF_2H$ | $CF_2H$ | 2-Me-4-$OCF_2H$ | $CH_2CF_3$ | 2-Me-4-$OCF_2H$ |
| $CF_3$ | 2-Me-4-$OCH_2CF_3$ | $CF_2H$ | 2-Me-4-$OCH_2CF_3$ | $CH_2CF_3$ | 2-Me-4-$OCH_2CF_3$ |
| $CF_3$ | 2-Me-4-$SCF_3$ | $CF_2H$ | 2-Me-4-$SCF_3$ | $CH_2CF_3$ | 2-Me-4-$SCF_3$ |
| $CF_3$ | 2-Me-4-$SOCF_3$ | $CF_2H$ | 2-Me-4-$SOCF_3$ | $CH_2CF_3$ | 2-Me-4-$SOCF_3$ |
| $CF_3$ | 2-Me-4-$SO_2CF_3$ | $CF_2H$ | 2-Me-4-$SO_2CF_3$ | $CH_2CF_3$ | 2-Me-4-$SO_2CF_3$ |
| $CF_3$ | 2-Me-4-$SCF_2H$ | $CF_2H$ | 2-Me-4-$SCF_2H$ | $CH_2CF_3$ | 2-Me-4-$SCF_2H$ |
| $CF_3$ | 2-Me-4-$SOCF_2H$ | $CF_2H$ | 2-Me-4-$SOCF_2H$ | $CH_2CF_3$ | 2-Me-4-$SOCF_2H$ |
| $CF_3$ | 2-Me-4-$SO_2CF_2H$ | $CF_2H$ | 2-Me-4-$SO_2CF_2H$ | $CH_2CF_3$ | 2-Me-4-$SO_2CF_2H$ |

TABLE 6

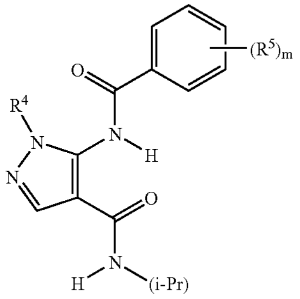

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| $CF_3$ | 2-Me-4-$CF_3$ | $CF_2H$ | 2-Me-4-$CF_3$ | $CH_2CF_3$ | 2-Me-4-$CF_3$ |
| $CF_3$ | 2-Me-4-$OCF_3$ | $CF_2H$ | 2-Me-4-$OCF_3$ | $CH_2CF_3$ | 2-Me-4-$OCF_3$ |
| $CF_3$ | 2-Me-4-$OCF_2H$ | $CF_2H$ | 2-Me-4-$OCF_2H$ | $CH_2CF_3$ | 2-Me-4-$OCF_2H$ |
| $CF_3$ | 2-Me-4-$OCH_2CF_3$ | $CF_2H$ | 2-Me-4-$OCH_2CF_3$ | $CH_2CF_3$ | 2-Me-4-$OCH_2CF_3$ |
| $CF_3$ | 2-Me-4-$SCF_3$ | $CF_2H$ | 2-Me-4-$SCF_3$ | $CH_2CF_3$ | 2-Me-4-$SCF_3$ |
| $CF_3$ | 2-Me-4-$SOCF_3$ | $CF_2H$ | 2-Me-4-$SOCF_3$ | $CH_2CF_3$ | 2-Me-4-$SOCF_3$ |
| $CF_3$ | 2-Me-4-$SO_2CF_3$ | $CF_2H$ | 2-Me-4-$SO_2CF_3$ | $CH_2CF_3$ | 2-Me-4-$SO_2CF_3$ |
| $CF_3$ | 2-Me-4-$SCF_2H$ | $CF_2H$ | 2-Me-4-$SCF_2H$ | $CH_2CF_3$ | 2-Me-4-$SCF_2H$ |

TABLE 6-continued

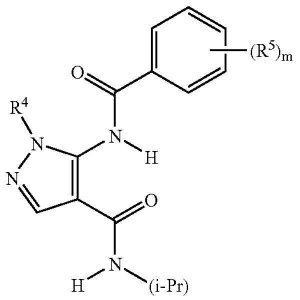

| $R^4$ | $(R^5)_m$ | $R^4$ | $(R^5)_m$ | $R^4$ | $(R^5)_m$ |
|---|---|---|---|---|---|
| $CF_3$ | 2-Me-4-$SOCF_2H$ | $CF_2H$ | 2-Me-4-$SOCF_2H$ | $CH_2CF_3$ | 2-Me-4-$SOCF_2H$ |
| $CF_3$ | 2-Me-4-$SO_2CF_2H$ | $CF_2H$ | 2-Me-4-$SO_2CF_2H$ | $CH_2CF_3$ | 2-Me-4-$SO_2CF_2H$ |

TABLE 7

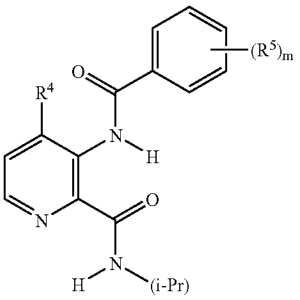

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |

TABLE 7-continued

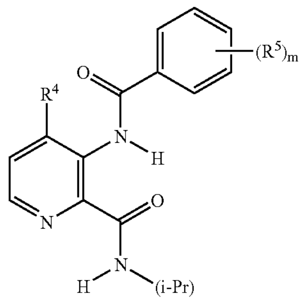

| $R^4$ | $(R^5)_m$ | $R^4$ | $(R^5)_m$ | $R^4$ | $(R^5)_m$ |
|---|---|---|---|---|---|
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |

TABLE 7-continued

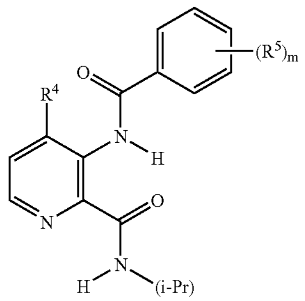

| $R^4$ | $(R^5)_m$ | $R^4$ | $(R^5)_m$ | $R^4$ | $(R^5)_m$ |
|---|---|---|---|---|---|
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 8

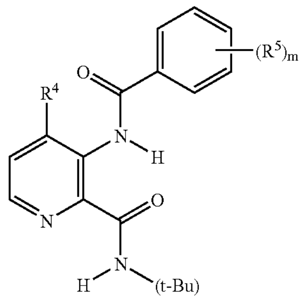

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |

TABLE 8-continued

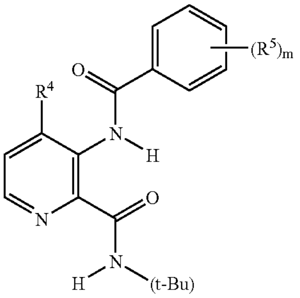

| $R^4$ | $(R^5)_m$ | $R^4$ | $(R^5)_m$ | $R^4$ | $(R^5)_m$ |
|---|---|---|---|---|---|
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |

TABLE 8-continued

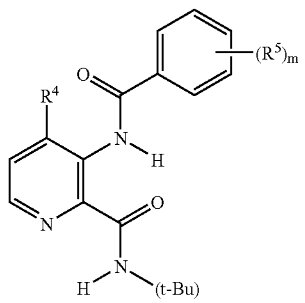

| $R^4$ | $(R^5)_m$ | $R^4$ | $(R^5)_m$ | $R^4$ | $(R^5)_m$ |
|---|---|---|---|---|---|
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 9

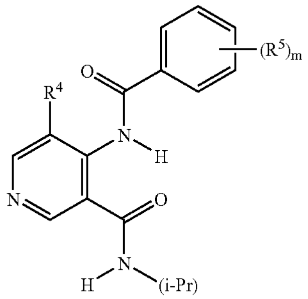

| $R^4$ | $(R^5)_m$ | $R^4$ | $(R^5)_m$ | $R^4$ | $(R^5)_m$ |
|---|---|---|---|---|---|
| Me | 2-$CF_3$ | Me | 3-$CF_3$ | Me | 4-$CF_3$ |
| Me | 2-$OCF_3$ | Me | 3-$OCF_3$ | Me | 4-$OCF_3$ |
| Me | 2-$OCF_2H$ | Me | 3-$OCF_2H$ | Me | 4-$OCF_2H$ |
| Me | 2-$OCF_2CF_2H$ | Me | 3-$OCF_2CF_2H$ | Me | 4-$OCF_2CF_2H$ |

TABLE 9-continued

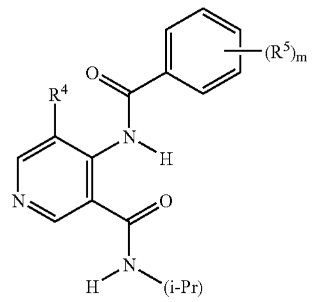

| $R^4$ | $(R^5)_m$ | $R^4$ | $(R^5)_m$ | $R^4$ | $(R^5)_m$ |
|---|---|---|---|---|---|
| Me | 2-$OCH_2CF_3$ | Me | 3-$OCH_2CF_3$ | Me | 4-$OCH_2CF_3$ |
| Me | 2-$SCF_3$ | Me | 3-$SCF_3$ | Me | 4-$SCF_3$ |
| Me | 2-$SOCF_3$ | Me | 3-$SOCF_3$ | Me | 4-$SOCF_3$ |
| Me | 2-$SO_2CF_3$ | Me | 3-$SO_2CF_3$ | Me | 4-$SO_2CF_3$ |
| Me | 2-$SCF_2H$ | Me | 3-$SCF_2H$ | Me | 4-$SCF_2H$ |
| Me | 2-$SOCF_2H$ | Me | 3-$SOCF_2H$ | Me | 4-$SOCF_2H$ |
| Me | 2-$SO_2CF_2H$ | Me | 3-$SO_2CF_2H$ | Me | 4-$SO_2CF_2H$ |
| Cl | 2-$CF_3$ | Cl | 3-$CF_3$ | Cl | 4-$CF_3$ |
| Cl | 2-$OCF_3$ | Cl | 3-$OCF_3$ | Cl | 4-$OCF_3$ |
| Cl | 2-$OCF_2H$ | Cl | 3-$OCF_2H$ | Cl | 4-$OCF_2H$ |
| Cl | 2-$OCF_2CF_2H$ | Cl | 3-$OCF_2CF_2H$ | Cl | 4-$OCF_2CF_2H$ |
| Cl | 2-$OCH_2CF_3$ | Cl | 3-$OCH_2CF_3$ | Cl | 4-$OCH_2CF_3$ |
| Cl | 2-$SCF_3$ | Cl | 3-$SCF_3$ | Cl | 4-$SCF_3$ |
| Cl | 2-$SOCF_3$ | Cl | 3-$SOCF_3$ | Cl | 4-$SOCF_3$ |
| Cl | 2-$SO_2CF_3$ | Cl | 3-$SO_2CF_3$ | Cl | 4-$SO_2CF_3$ |
| Cl | 2-$SCF_2H$ | Cl | 3-$SCF_2H$ | Cl | 4-$SCF_2H$ |
| Cl | 2-$SOCF_2H$ | Cl | 3-$SOCF_2H$ | Cl | 4-$SOCF_2H$ |
| Cl | 2-$SO_2CF_2H$ | Cl | 3-$SO_2CF_2H$ | Cl | 4-$SO_2CF_2H$ |
| F | 2-$CF_3$ | F | 3-$CF_3$ | F | 4-$CF_3$ |
| F | 2-$OCF_3$ | F | 3-$OCF_3$ | F | 4-$OCF_3$ |
| F | 2-$OCF_2H$ | F | 3-$OCF_2H$ | F | 4-$OCF_2H$ |
| F | 2-$OCF_2CF_2H$ | F | 3-$OCF_2CF_2H$ | F | 4-$OCF_2CF_2H$ |
| F | 2-$OCH_2CF_3$ | F | 3-$OCH_2CF_3$ | F | 4-$OCH_2CF_3$ |
| F | 2-$SCF_3$ | F | 3-$SCF_3$ | F | 4-$SCF_3$ |
| F | 2-$SOCF_3$ | F | 3-$SOCF_3$ | F | 4-$SOCF_3$ |
| F | 2-$SO_2CF_3$ | F | 3-$SO_2CF_3$ | F | 4-$SO_2CF_3$ |
| F | 2-$SCF_2H$ | F | 3-$SCF_2H$ | F | 4-$SCF_2H$ |
| F | 2-$SOCF_2H$ | F | 3-$SOCF_2H$ | F | 4-$SOCF_2H$ |
| F | 2-$SO_2CF_2H$ | F | 3-$SO_2CF_2H$ | F | 4-$SO_2CF_2H$ |
| Br | 2-$CF_3$ | Br | 3-$CF_3$ | Br | 4-$CF_3$ |
| Br | 2-$OCF_3$ | Br | 3-$OCF_3$ | Br | 4-$OCF_3$ |
| Br | 2-$OCF_2H$ | Br | 3-$OCF_2H$ | Br | 4-$OCF_2H$ |
| Br | 2-$OCF_2CF_2H$ | Br | 3-$OCF_2CF_2H$ | Br | 4-$OCF_2CF_2H$ |
| Br | 2-$OCH_2CF_3$ | Br | 3-$OCH_2CF_3$ | Br | 4-$OCH_2CF_3$ |
| Br | 2-$SCF_3$ | Br | 3-$SCF_3$ | Br | 4-$SCF_3$ |
| Br | 2-$SOCF_3$ | Br | 3-$SOCF_3$ | Br | 4-$SOCF_3$ |
| Br | 2-$SO_2CF_3$ | Br | 3-$SO_2CF_3$ | Br | 4-$SO_2CF_3$ |
| Br | 2-$SCF_2H$ | Br | 3-$SCF_2H$ | Br | 4-$SCF_2H$ |
| Br | 2-$SOCF_2H$ | Br | 3-$SOCF_2H$ | Br | 4-$SOCF_2H$ |
| Br | 2-$SO_2CF_2H$ | Br | 3-$SO_2CF_2H$ | Br | 4-$SO_2CF_2H$ |
| I | 2-$CF_3$ | I | 3-$CF_3$ | I | 4-$CF_3$ |
| I | 2-$OCF_3$ | I | 3-$OCF_3$ | I | 4-$OCF_3$ |
| I | 2-$OCF_2H$ | I | 3-$OCF_2H$ | I | 4-$OCF_2H$ |
| I | 2-$OCF_2CF_2H$ | I | 3-$OCF_2CF_2H$ | I | 4-$OCF_2CF_2H$ |
| I | 2-$OCH_2CF_3$ | I | 3-$OCH_2CF_3$ | I | 4-$OCH_2CF_3$ |
| I | 2-$SCF_3$ | I | 3-$SCF_3$ | I | 4-$SCF_3$ |
| I | 2-$SOCF_3$ | I | 3-$SOCF_3$ | I | 4-$SOCF_3$ |
| I | 2-$SO_2CF_3$ | I | 3-$SO_2CF_3$ | I | 4-$SO_2CF_3$ |
| I | 2-$SCF_2H$ | I | 3-$SCF_2H$ | I | 4-$SCF_2H$ |
| I | 2-$SOCF_2H$ | I | 3-$SOCF_2H$ | I | 4-$SOCF_2H$ |
| I | 2-$SO_2CF_2H$ | I | 3-$SO_2CF_2H$ | I | 4-$SO_2CF_2H$ |
| OMe | 2-$CF_3$ | OMe | 3-$CF_3$ | OMe | 4-$CF_3$ |
| OMe | 2-$OCF_3$ | OMe | 3-$OCF_3$ | OMe | 4-$OCF_3$ |
| OMe | 2-$OCF_2H$ | OMe | 3-$OCF_2H$ | OMe | 4-$OCF_2H$ |
| OMe | 2-$OCF_2CF_2H$ | OMe | 3-$OCF_2CF_2H$ | OMe | 4-$OCF_2CF_2H$ |
| OMe | 2-$OCH_2CF_3$ | OMe | 3-$OCH_2CF_3$ | OMe | 4-$OCH_2CF_3$ |
| OMe | 2-$SCF_3$ | OMe | 3-$SCF_3$ | OMe | 4-$SCF_3$ |
| OMe | 2-$SOCF_3$ | OMe | 3-$SOCF_3$ | OMe | 4-$SOCF_3$ |
| OMe | 2-$SO_2CF_3$ | OMe | 3-$SO_2CF_3$ | OMe | 4-$SO_2CF_3$ |
| OMe | 2-$SCF_2H$ | OMe | 3-$SCF_2H$ | OMe | 4-$SCF_2H$ |
| OMe | 2-$SOCF_2H$ | OMe | 3-$SOCF_2H$ | OMe | 4-$SOCF_2H$ |
| OMe | 2-$SO_2CF_2H$ | OMe | 3-$SO_2CF_2H$ | OMe | 4-$SO_2CF_2H$ |

TABLE 9-continued

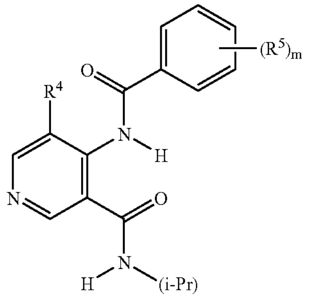

| $R^4$ | $(R^5)_m$ | $R^4$ | $(R^5)_m$ | $R^4$ | $(R^5)_m$ |
|---|---|---|---|---|---|
| $CF_3$ | 2-$CF_3$ | $CF_3$ | 3-$CF_3$ | $CF_3$ | 4-$CF_3$ |
| $CF_3$ | 2-$OCF_3$ | $CF_3$ | 3-$OCF_3$ | $CF_3$ | 4-$OCF_3$ |
| $CF_3$ | 2-$OCF_2H$ | $CF_3$ | 3-$OCF_2H$ | $CF_3$ | 4-$OCF_2H$ |
| $CF_3$ | 2-$OCF_2CF_2H$ | $CF_3$ | 3-$OCF_2CF_2H$ | $CF_3$ | 4-$OCF_2CF_2H$ |
| $CF_3$ | 2-$OCH_2CF_3$ | $CF_3$ | 3-$OCH_2CF_3$ | $CF_3$ | 4-$OCH_2CF_3$ |
| $CF_3$ | 2-$SCF_3$ | $CF_3$ | 3-$SCF_3$ | $CF_3$ | 4-$SCF_3$ |
| $CF_3$ | 2-$SOCF_3$ | $CF_3$ | 3-$SOCF_3$ | $CF_3$ | 4-$SOCF_3$ |
| $CF_3$ | 2-$SO_2CF_3$ | $CF_3$ | 3-$SO_2CF_3$ | $CF_3$ | 4-$SO_2CF_3$ |
| $CF_3$ | 2-$SCF_2H$ | $CF_3$ | 3-$SCF_2H$ | $CF_3$ | 4-$SCF_2H$ |
| $CF_3$ | 2-$SOCF_2H$ | $CF_3$ | 3-$SOCF_2H$ | $CF_3$ | 4-$SOCF_2H$ |
| $CF_3$ | 2-$SO_2CF_2H$ | $CF_3$ | 3-$SO_2CF_2H$ | $CF_3$ | 4-$SO_2CF_2H$ |
| $OCF_2H$ | 2-$CF_3$ | $OCF_2H$ | 3-$CF_3$ | $OCF_2H$ | 4-$CF_3$ |
| $OCF_2H$ | 2-$OCF_3$ | $OCF_2H$ | 3-$OCF_3$ | $OCF_2H$ | 4-$OCF_3$ |
| $OCF_2H$ | 2-$OCF_2H$ | $OCF_2H$ | 3-$OCF_2H$ | $OCF_2H$ | 4-$OCF_2H$ |
| $OCF_2H$ | 2-$OCF_2CF_2H$ | $OCF_2H$ | 3-$OCF_2CF_2H$ | $OCF_2H$ | 4-$OCF_2CF_2H$ |
| $OCF_2H$ | 2-$OCH_2CF_3$ | $OCF_2H$ | 3-$OCH_2CF_3$ | $OCF_2H$ | 4-$OCH_2CF_3$ |
| $OCF_2H$ | 2-$SCF_3$ | $OCF_2H$ | 3-$SCF_3$ | $OCF_2H$ | 4-$SCF_3$ |
| $OCF_2H$ | 2-$SOCF_3$ | $OCF_2H$ | 3-$SOCF_3$ | $OCF_2H$ | 4-$SOCF_3$ |
| $OCF_2H$ | 2-$SO_2CF_3$ | $OCF_2H$ | 3-$SO_2CF_3$ | $OCF_2H$ | 4-$SO_2CF_3$ |
| $OCF_2H$ | 2-$SCF_2H$ | $OCF_2H$ | 3-$SCF_2H$ | $OCF_2H$ | 4-$SCF_2H$ |
| $OCF_2H$ | 2-$SOCF_2H$ | $OCF_2H$ | 3-$SOCF_2H$ | $OCF_2H$ | 4-$SOCF_2H$ |
| $OCF_2H$ | 2-$SO_2CF_2H$ | $OCF_2H$ | 3-$SO_2CF_2H$ | $OCF_2H$ | 4-$SO_2CF_2H$ |
| Me | 2-Me-4-$CF_3$ | F | 2-Me-4-$CF_3$ | Cl | 2-Me-4-$CF_3$ |
| Me | 2-Me-4-$OCF_3$ | F | 2-Me-4-$OCF_3$ | Cl | 2-Me-4-$OCF_3$ |
| Me | 2-Me-4-$OCF_2H$ | F | 2-Me-4-$OCF_2H$ | Cl | 2-Me-4-$OCF_2H$ |
| Me | 2-Me-4-$OCH_2CF_3$ | F | 2-Me-4-$OCH_2CF_3$ | Cl | 2-Me-4-$OCH_2CF_3$ |
| Me | 2-Me-4-$SCF_3$ | F | 2-Me-4-$SCF_3$ | Cl | 2-Me-4-$SCF_3$ |
| Me | 2-Me-4-$SOCF_3$ | F | 2-Me-4-$SOCF_3$ | Cl | 2-Me-4-$SOCF_3$ |
| Me | 2-Me-4-$SO_2CF_3$ | F | 2-Me-4-$SO_2CF_3$ | Cl | 2-Me-4-$SO_2CF_3$ |
| Me | 2-Me-4-$SCF_2H$ | F | 2-Me-4-$SCF_2H$ | Cl | 2-Me-4-$SCF_2H$ |
| Me | 2-Me-4-$SOCF_2H$ | F | 2-Me-4-$SOCF_2H$ | Cl | 2-Me-4-$SOCF_2H$ |
| Me | 2-Me-4-$SO_2CF_2H$ | F | 2-Me-4-$SO_2CF_2H$ | Cl | 2-Me-4-$SO_2CF_2H$ |
| Br | 2-Me-4-$CF_3$ | I | 2-Me-4-$CF_3$ | OMe | 2-Me-4-$CF_3$ |
| Br | 2-Me-4-$OCF_3$ | I | 2-Me-4-$OCF_3$ | OMe | 2-Me-4-$OCF_3$ |
| Br | 2-Me-4-$OCF_2H$ | I | 2-Me-4-$OCF_2H$ | OMe | 2-Me-4-$OCF_2H$ |
| Br | 2-Me-4-$OCH_2CF_3$ | I | 2-Me-4-$OCH_2CF_3$ | OMe | 2-Me-4-$OCH_2CF_3$ |
| Br | 2-Me-4-$SCF_3$ | I | 2-Me-4-$SCF_3$ | OMe | 2-Me-4-$SCF_3$ |
| Br | 2-Me-4-$SOCF_3$ | I | 2-Me-4-$SOCF_3$ | OMe | 2-Me-4-$SOCF_3$ |
| Br | 2-Me-4-$SO_2CF_3$ | I | 2-Me-4-$SO_2CF_3$ | OMe | 2-Me-4-$SO_2CF_3$ |
| Br | 2-Me-4-$SCF_2H$ | I | 2-Me-4-$SCF_2H$ | OMe | 2-Me-4-$SCF_2H$ |
| Br | 2-Me-4-$SOCF_2H$ | I | 2-Me-4-$SOCF_2H$ | OMe | 2-Me-4-$SOCF_2H$ |
| Br | 2-Me-4-$SO_2CF_2H$ | I | 2-Me-4-$SO_2CF_2H$ | OMe | 2-Me-4-$SO_2CF_2H$ |
| $CF_3$ | 2-Me-4-$CF_3$ | $NO_2$ | 2-Me-4-$CF_3$ | SMe | 2-Me-4-$CF_3$ |
| $CF_3$ | 2-Me-4-$OCF_3$ | $NO_2$ | 2-Me-4-$OCF_3$ | SMe | 2-Me-4-$OCF_3$ |
| $CF_3$ | 2-Me-4-$OCF_2H$ | $NO_2$ | 2-Me-4-$OCF_2H$ | SMe | 2-Me-4-$OCF_2H$ |
| $CF_3$ | 2-Me-4-$OCH_2CF_3$ | $NO_2$ | 2-Me-4-$OCH_2CF_3$ | SMe | 2-Me-4-$OCH_2CF_3$ |
| $CF_3$ | 2-Me-4-$SCF_3$ | $NO_2$ | 2-Me-4-$SCF_3$ | SMe | 2-Me-4-$SCF_3$ |
| $CF_3$ | 2-Me-4-$SOCF_3$ | $NO_2$ | 2-Me-4-$SOCF_3$ | SMe | 2-Me-4-$SOCF_3$ |
| $CF_3$ | 2-Me-4-$SO_2CF_3$ | $NO_2$ | 2-Me-4-$SO_2CF_3$ | SMe | 2-Me-4-$SO_2CF_3$ |
| $CF_3$ | 2-Me-4-$SCF_2H$ | $NO_2$ | 2-Me-4-$SCF_2H$ | SMe | 2-Me-4-$SCF_2H$ |
| $CF_3$ | 2-Me-4-$SOCF_2H$ | $NO_2$ | 2-Me-4-$SOCF_2H$ | SMe | 2-Me-4-$SOCF_2H$ |
| $CF_3$ | 2-Me-4-$SO_2CF_2H$ | $NO_2$ | 2-Me-4-$SO_2CF_2H$ | SMe | 2-Me-4-$SO_2CF_2H$ |

TABLE 10

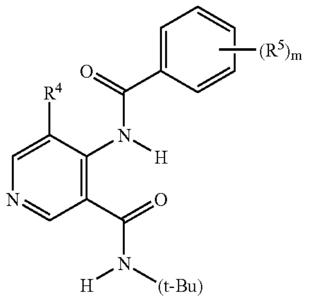

| $R^4$ | $(R^5)_m$ |
|---|---|
| Me | 2-$CF_3$ |
| Me | 2-$OCF_3$ |
| Me | 2-$OCF_2H$ |
| Me | 2-$OCF_2CF_2H$ |
| Me | 2-$OCH_2CF_3$ |
| Me | 2-$SCF_3$ |
| Me | 2-$SOCF_3$ |
| Me | 2-$SO_2CF_3$ |
| Me | 2-$SCF_2H$ |
| Me | 2-$SOCF_2H$ |
| Me | 2-$SO_2CF_2H$ |
| Me | 3-$CF_3$ |
| Me | 3-$OCF_3$ |
| Me | 3-$OCF_2H$ |
| Me | 3-$OCF_2CF_3H$ |
| Me | 3-$OCH_2CF_3$ |
| Me | 3-$SCF_3$ |
| Me | 3-$SOCF_3$ |
| Me | 3-$SO_2CF_3$ |
| Me | 3-$SCF_2H$ |
| Me | 3-$SOCF_2H$ |
| Me | 3-$SO_2CF_2H$ |
| Me | 4-$CF_3$ |
| Me | 4-$OCF_3$ |
| Me | 4-$OCF_2H$ |
| Me | 4-$OCF_2CF_3H$ |
| Me | 4-$OCH_2CF_3$ |
| Me | 4-$SCF_3$ |
| Me | 4-$SOCF_3$ |
| Me | 4-$SO_2CF_3$ |
| Me | 4-$SCF_2H$ |
| Me | 4-$SOCF_2H$ |
| Me | 4-$SO_2CF_2H$ |
| Cl | 2-$CF_3$ |
| Cl | 2-$OCF_3$ |
| Cl | 2-$OCF_2H$ |
| Cl | 2-$OCF_2CF_2H$ |
| Cl | 2-$OCH_2CF_3$ |
| Cl | 2-$SCF_3$ |
| Cl | 2-$SOCF_3$ |
| Cl | 2-$SO_2CF_3$ |
| Cl | 2-$SCF_2H$ |
| Cl | 2-$SOCF_2H$ |
| Cl | 2-$SO_2CF_2H$ |
| Cl | 3-$CF_3$ |
| Cl | 3-$OCF_3$ |
| Cl | 3-$OCF_2H$ |
| Cl | 3-$OCF_2CF_3H$ |
| Cl | 3-$OCH_2CF_3$ |
| Cl | 3-$SCF_3$ |
| Cl | 3-$SOCF_3$ |
| Cl | 3-$SO_2CF_3$ |
| Cl | 3-$SCF_2H$ |
| Cl | 3-$SOCF_2H$ |
| Cl | 3-$SO_2CF_2H$ |
| Cl | 4-$CF_3$ |
| Cl | 4-$OCF_3$ |
| Cl | 4-$OCF_2H$ |
| Cl | 4-$OCF_2CF_3H$ |
| Cl | 4-$OCH_2CF_3$ |
| Cl | 4-$SCF_3$ |
| Cl | 4-$SOCF_3$ |

TABLE 10-continued

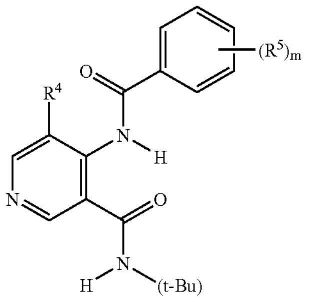

| $R^4$ | $(R^5)_m$ |
|---|---|
| Cl | 4-$SO_2CF_3$ |
| Cl | 4-$SCF_2H$ |
| Cl | 4-$SOCF_2H$ |
| Cl | 4-$SO_2CF_2H$ |
| F | 2-$CF_3$ |
| F | 2-$OCF_3$ |
| F | 2-$OCF_2H$ |
| F | 2-$OCF_2CF_2H$ |
| F | 2-$OCH_2CF_3$ |
| F | 2-$SCF_3$ |
| F | 2-$SOCF_3$ |
| F | 2-$SO_2CF_3$ |
| F | 2-$SCF_2H$ |
| F | 2-$SOCF_2H$ |
| F | 2-$SO_2CF_2H$ |
| F | 3-$CF_3$ |
| F | 3-$OCF_3$ |
| F | 3-$OCF_2H$ |
| F | 3-$OCF_2CF_3H$ |
| F | 3-$OCH_2CF_3$ |
| F | 3-$SCF_3$ |
| F | 3-$SOCF_3$ |
| F | 3-$SO_2CF_3$ |
| F | 3-$SCF_2H$ |
| F | 3-$SOCF_2H$ |
| F | 3-$SO_2CF_2H$ |
| F | 4-$CF_3$ |
| F | 4-$OCF_3$ |
| F | 4-$OCF_2H$ |
| F | 4-$OCF_2CF_3H$ |
| F | 4-$OCH_2CF_3$ |
| F | 4-$SCF_3$ |
| F | 4-$SOCF_3$ |
| F | 4-$SO_2CF_3$ |
| F | 4-$SCF_2H$ |
| F | 4-$SOCF_2H$ |
| F | 4-$SO_2CF_2H$ |
| Br | 2-$CF_3$ |
| Br | 2-$OCF_3$ |
| Br | 2-$OCF_2H$ |
| Br | 2-$OCF_2CF_2H$ |
| Br | 2-$OCH_2CF_3$ |
| Br | 2-$SCF_3$ |
| Br | 2-$SOCF_3$ |
| Br | 2-$SO_2CF_3$ |
| Br | 2-$SCF_2H$ |
| Br | 2-$SOCF_2H$ |
| Br | 2-$SO_2CF_2H$ |
| Br | 3-$CF_3$ |
| Br | 3-$OCF_3$ |
| Br | 3-$OCF_2H$ |
| Br | 3-$OCF_2CF_3H$ |
| Br | 3-$OCH_2CF_3$ |
| Br | 3-$SCF_3$ |
| Br | 3-$SOCF_3$ |
| Br | 3-$SO_2CF_3$ |
| Br | 3-$SCF_2H$ |
| Br | 3-$SOCF_2H$ |
| Br | 3-$SO_2CF_2H$ |
| Br | 4-$CF_3$ |
| Br | 4-$OCF_3$ |
| Br | 4-$OCF_2H$ |

TABLE 10-continued

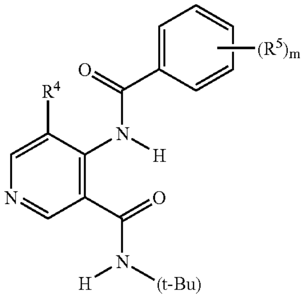

| $R^4$ | $(R^5)_m$ |
|---|---|
| Br | 4-$OCF_2CF_3H$ |
| Br | 4-$OCH_2CF_3$ |
| Br | 4-$SCF_3$ |
| Br | 4-$SOCF_3$ |
| Br | 4-$SO_2CF_3$ |
| Br | 4-$SCF_2H$ |
| Br | 4-$SOCF_2H$ |
| Br | 4-$SO_2CF_2H$ |
| I | 2-$CF_3$ |
| I | 2-$OCF_3$ |
| I | 2-$OCF_2H$ |
| I | 2-$OCF_2CF_2H$ |
| I | 2-$OCH_2CF_3$ |
| I | 2-$SCF_3$ |
| I | 2-$SOCF_3$ |
| I | 2-$SO_2CF_3$ |
| I | 2-$SCF_2H$ |
| I | 2-$SOCF_2H$ |
| I | 2-$SO_2CF_2H$ |
| I | 3-$CF_3$ |
| I | 3-$OCF_3$ |
| I | 3-$OCF_2H$ |
| I | 3-$OCF_2CF_3H$ |
| I | 3-$OCH_2CF_3$ |
| I | 3-$SCF_3$ |
| I | 3-$SOCF_3$ |
| I | 3-$SO_2CF_3$ |
| I | 3-$SCF_2H$ |
| I | 3-$SOCF_2H$ |
| I | 3-$SO_2CF_2H$ |
| I | 4-$CF_3$ |
| I | 4-$OCF_3$ |
| I | 4-$OCF_2H$ |
| I | 4-$OCF_2CF_3H$ |
| I | 4-$OCH_2CF_3$ |
| I | 4-$SCF_3$ |
| I | 4-$SOCF_3$ |
| I | 4-$SO_2CF_3$ |
| I | 4-$SCF_2H$ |
| I | 4-$SOCF_2H$ |
| I | 4-$SO_2CF_2H$ |
| OMe | 2-$CF_3$ |
| OMe | 2-$OCF_3$ |
| OMe | 2-$OCF_2H$ |
| OMe | 2-$OCF_2CF_2H$ |
| OMe | 2-$OCH_2CF_3$ |
| OMe | 2-$SCF_3$ |
| OMe | 2-$SOCF_3$ |
| OMe | 2-$SO_2CF_3$ |
| OMe | 2-$SCF_2H$ |
| OMe | 2-$SOCF_2H$ |
| OMe | 2-$SO_2CF_2H$ |
| OMe | 3-$CF_3$ |
| OMe | 3-$OCF_3$ |
| OMe | 3-$OCF_2H$ |
| OMe | 3-$OCF_2CF_3H$ |
| OMe | 3-$OCH_2CF_3$ |
| OMe | 3-$SCF_3$ |
| OMe | 3-$SOCF_3$ |
| OMe | 3-$SO_2CF_3$ |
| OMe | 3-$SCF_2H$ |
| OMe | 3-$SOCF_2H$ |

TABLE 10-continued

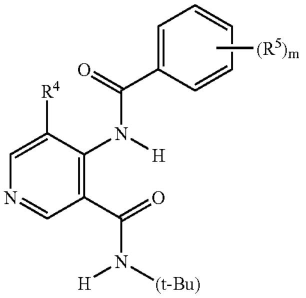

| $R^4$ | $(R^5)_m$ |
|---|---|
| OMe | 3-$SO_2CF_2H$ |
| OMe | 4-$CF_3$ |
| OMe | 4-$OCF_3$ |
| OMe | 4-$OCF_2H$ |
| OMe | 4-$OCF_2CF_3H$ |
| OMe | 4-$OCH_2CF_3$ |
| OMe | 4-$SCF_3$ |
| OMe | 4-$SOCF_3$ |
| OMe | 4-$SO_2CF_3$ |
| OMe | 4-$SCF_2H$ |
| OMe | 4-$SOCF_2H$ |
| OMe | 4-$SO_2CF_2H$ |
| $CF_3$ | 2-$CF_3$ |
| $CF_3$ | 2-$OCF_3$ |
| $CF_3$ | 2-$OCF_2H$ |
| $CF_3$ | 2-$OCF_2CF_2H$ |
| $CF_3$ | 2-$OCH_2CF_3$ |
| $CF_3$ | 2-$SCF_3$ |
| $CF_3$ | 2-$SOCF_3$ |
| $CF_3$ | 2-$SO_2CF_3$ |
| $CF_3$ | 2-$SCF_2H$ |
| $CF_3$ | 2-$SOCF_2H$ |
| $CF_3$ | 2-$SO_2CF_2H$ |
| $CF_3$ | 3-$CF_3$ |
| $CF_3$ | 3-$OCF_3$ |
| $CF_3$ | 3-$OCF_2H$ |
| $CF_3$ | 3-$OCF_2CF_3H$ |
| $CF_3$ | 3-$OCH_2CF_3$ |
| $CF_3$ | 3-$SCF_3$ |
| $CF_3$ | 3-$SOCF_3$ |
| $CF_3$ | 3-$SO_2CF_3$ |
| $CF_3$ | 3-$SCF_2H$ |
| $CF_3$ | 3-$SOCF_2H$ |
| $CF_3$ | 3-$SO_2CF_2H$ |
| $CF_3$ | 4-$CF_3$ |
| $CF_3$ | 4-$OCF_3$ |
| $CF_3$ | 4-$OCF_2H$ |
| $CF_3$ | 4-$OCF_2CF_3H$ |
| $CF_3$ | 4-$OCH_2CF_3$ |
| $CF_3$ | 4-$SCF_3$ |
| $CF_3$ | 4-$SOCF_3$ |
| $CF_3$ | 4-$SO_2CF_3$ |
| $CF_3$ | 4-$SCF_2H$ |
| $CF_3$ | 4-$SOCF_2H$ |
| $CF_3$ | 4-$SO_2CF_2H$ |
| $OCF_2H$ | 2-$CF_3$ |
| $OCF_2H$ | 2-$OCF_3$ |
| $OCF_2H$ | 2-$OCF_2H$ |
| $OCF_2H$ | 2-$OCF_2CF_2H$ |
| $OCF_2H$ | 2-$OCH_2CF_3$ |
| $OCF_2H$ | 2-$SCF_3$ |
| $OCF_2H$ | 2-$SOCF_3$ |
| $OCF_2H$ | 2-$SO_2CF_3$ |
| $OCF_2H$ | 2-$SCF_2H$ |
| $OCF_2H$ | 2-$SOCF_2H$ |
| $OCF_2H$ | 2-$SO_2CF_2H$ |
| $OCF_2H$ | 3-$CF_3$ |
| $OCF_2H$ | 3-$OCF_3$ |
| $OCF_2H$ | 3-$OCF_2H$ |
| $OCF_2H$ | 3-$OCF_2CF_3H$ |
| $OCF_2H$ | 3-$OCH_2CF_3$ |
| $OCF_2H$ | 3-$SCF_3$ |

TABLE 10-continued

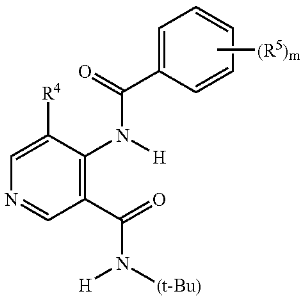

| $R^4$ | $(R^5)_m$ |
|---|---|
| $OCF_2H$ | 3-$SOCF_3$ |
| $OCF_2H$ | 3-$SO_2CF_3$ |
| $OCF_2H$ | 3-$SCF_2H$ |
| $OCF_2H$ | 3-$SOCF_2H$ |
| $OCF_2H$ | 3-$SO_2CF_2H$ |
| $OCF_2H$ | 4-$CF_3$ |
| $OCF_2H$ | 4-$OCF_3$ |
| $OCF_2H$ | 4-$OCF_2H$ |
| $OCF_2H$ | 4-$OCF_2CF_3H$ |
| $OCF_2H$ | 4-$OCH_2CF_3$ |
| $OCF_2H$ | 4-$SCF_3$ |
| $OCF_2H$ | 4-$SOCF_3$ |
| $OCF_2H$ | 4-$SO_2CF_3$ |
| $OCF_2H$ | 4-$SCF_2H$ |
| $OCF_2H$ | 4-$SOCF_2H$ |
| $OCF_2H$ | 4-$SO_2CF_2H$ |
| Me | 2-Me-4-$CF_3$ |
| Me | 2-Me-4-$OCF_3$ |
| Me | 2-Me-4-$OCF_2H$ |
| Me | 2-Me-4-$OCH_2CF_3$ |
| Me | 2-Me-4-$SCF_3$ |
| Me | 2-Me-4-$SOCF_3$ |
| Me | 2-Me-4-$SO_2CF_3$ |
| Me | 2-Me-4-$SCF_2H$ |
| Me | 2-Me-4-$SOCF_2H$ |
| Me | 2-Me-4-$SO_2CF_2H$ |
| Br | 2-Me-4-$CF_3$ |
| Br | 2-Me-4-$OCF_3$ |
| Br | 2-Me-4-$OCF_2H$ |
| Br | 2-Me-4-$OCH_2CF_3$ |
| Br | 2-Me-4-$SCF_3$ |
| Br | 2-Me-4-$SOCF_3$ |
| Br | 2-Me-4-$SO_2CF_3$ |
| Br | 2-Me-4-$SCF_2H$ |
| Br | 2-Me-4-$SOCF_2H$ |
| Br | 2-Me-4-$SO_2CF_2H$ |
| $CF_3$ | 2-Me-4-$CF_3$ |
| $CF_3$ | 2-Me-4-$OCF_3$ |
| $CF_3$ | 2-Me-4-$OCF_2H$ |
| $CF_3$ | 2-Me-4-$OCH_2CF_3$ |
| $CF_3$ | 2-Me-4-$SCF_3$ |
| $CF_3$ | 2-Me-4-$SOCF_3$ |
| $CF_3$ | 2-Me-4-$SO_2CF_3$ |
| $CF_3$ | 2-Me-4-$SCF_2H$ |
| $CF_3$ | 2-Me-4-$SOCF_2H$ |
| $CF_3$ | 2-Me-4-$SO_2CF_2H$ |
| F | 2-Me-4-$CF_3$ |
| F | 2-Me-4-$OCF_3$ |
| F | 2-Me-4-$OCF_2H$ |
| F | 2-Me-4-$OCH_2CF_3$ |
| F | 2-Me-4-$SCF_3$ |
| F | 2-Me-4-$SOCF_3$ |
| F | 2-Me-4-$SO_2CF_3$ |
| F | 2-Me-4-$SCF_2H$ |
| F | 2-Me-4-$SOCF_2H$ |
| F | 2-Me-4-$SO_2CF_2H$ |
| I | 2-Me-4-$CF_3$ |
| I | 2-Me-4-$OCF_3$ |
| I | 2-Me-4-$OCF_2H$ |
| I | 2-Me-4-$OCH_2CF_3$ |
| I | 2-Me-4-$SCF_3$ |
| I | 2-Me-4-$SOCF_3$ |

TABLE 10-continued

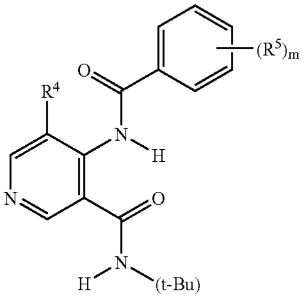

| $R^4$ | $(R^5)_m$ |
|---|---|
| I | 2-Me-4-$SO_2CF_3$ |
| I | 2-Me-4-$SCF_2H$ |
| I | 2-Me-4-$SOCF_2H$ |
| I | 2-Me-4-$SO_2CF_2H$ |
| $NO_2$ | 2-Me-4-$CF_3$ |
| $NO_2$ | 2-Me-4-$OCF_3$ |
| $NO_2$ | 2-Me-4-$OCF_2H$ |
| $NO_2$ | 2-Me-4-$OCH_2CF_3$ |
| $NO_2$ | 2-Me-4-$SCF_3$ |
| $NO_2$ | 2-Me-4-$SOCF_3$ |
| $NO_2$ | 2-Me-4-$SO_2CF_3$ |
| $NO_2$ | 2-Me-4-$SCF_2H$ |
| $NO_2$ | 2-Me-4-$SOCF_2H$ |
| $NO_2$ | 2-Me-4-$SO_2CF_2H$ |
| Cl | 2-Me-4-$CF_3$ |
| Cl | 2-Me-4-$OCF_3$ |
| Cl | 2-Me-4-$OCF_2H$ |
| Cl | 2-Me-4-$OCH_2CF_3$ |
| Cl | 2-Me-4-$SCF_3$ |
| Cl | 2-Me-4-$SOCF_3$ |
| Cl | 2-Me-4-$SO_2CF_3$ |
| Cl | 2-Me-4-$SCF_2H$ |
| Cl | 2-Me-4-$SOCF_2H$ |
| Cl | 2-Me-4-$SO_2CF_2H$ |
| OMe | 2-Me-4-$CF_3$ |
| OMe | 2-Me-4-$OCF_3$ |
| OMe | 2-Me-4-$OCF_2H$ |
| OMe | 2-Me-4-$OCH_2CF_3$ |
| OMe | 2-Me-4-$SCF_3$ |
| OMe | 2-Me-4-$SOCF_3$ |
| OMe | 2-Me-4-$SO_2CF_3$ |
| OMe | 2-Me-4-$SCF_2H$ |
| OMe | 2-Me-4-$SOCF_2H$ |
| OMe | 2-Me-4-$SO_2CF_2H$ |
| SMe | 2-Me-4-$CF_3$ |
| SMe | 2-Me-4-$OCF_3$ |
| SMe | 2-Me-4-$OCF_2H$ |
| SMe | 2-Me-4-$OCH_2CF_3$ |
| SMe | 2-Me-4-$SCF_3$ |
| SMe | 2-Me-4-$SOCF_3$ |
| SMe | 2-Me-4-$SO_2CF_3$ |
| SMe | 2-Me-4-$SCF_2H$ |
| SMe | 2-Me-4-$SOCF_2H$ |
| SMe | 2-Me-4-$SO_2CF_2H$ |

TABLE 11

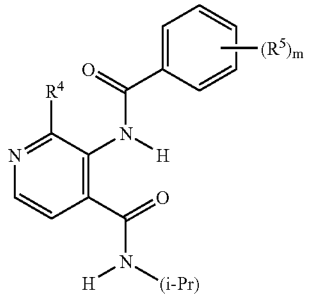

| $R^4$ | $(R^5)_m$ |
|---|---|
| Me | 2-$CF_3$ |
| Me | 2-$OCF_3$ |
| Me | 2-$OCF_2H$ |
| Me | 2-$OCF_2CF_2H$ |
| Me | 2-$OCH_2CF_3$ |
| Me | 2-$SCF_3$ |
| Me | 2-$SOCF_3$ |
| Me | 2-$SO_2CF_3$ |
| Me | 2-$SCF_2H$ |
| Me | 2-$SOCF_2H$ |
| Me | 2-$SO_2CF_2H$ |
| Me | 3-$CF_3$ |
| Me | 3-$OCF_3$ |
| Me | 3-$OCF_2H$ |
| Me | 3-$OCF_2CF_3H$ |
| Me | 3-$OCH_2CF_3$ |
| Me | 3-$SCF_3$ |
| Me | 3-$SOCF_3$ |
| Me | 3-$SO_2CF_3$ |
| Me | 3-$SCF_2H$ |
| Me | 3-$SOCF_2H$ |
| Me | 3-$SO_2CF_2H$ |
| Me | 4-$CF_3$ |
| Me | 4-$OCF_3$ |
| Me | 4-$OCF_2H$ |
| Me | 4-$OCF_2CF_3H$ |
| Me | 4-$OCH_2CF_3$ |
| Me | 4-$SCF_3$ |
| Me | 4-$SOCF_3$ |
| Me | 4-$SO_2CF_3$ |
| Me | 4-$SCF_2H$ |
| Me | 4-$SOCF_2H$ |
| Me | 4-$SO_2CF_2H$ |
| Cl | 2-$CF_3$ |
| Cl | 2-$OCF_3$ |
| Cl | 2-$OCF_2H$ |
| Cl | 2-$OCF_2CF_2H$ |
| Cl | 2-$OCH_2CF_3$ |
| Cl | 2-$SCF_3$ |
| Cl | 2-$SOCF_3$ |
| Cl | 2-$SO_2CF_3$ |
| Cl | 2-$SCF_2H$ |
| Cl | 2-$SOCF_2H$ |
| Cl | 2-$SO_2CF_2H$ |
| Cl | 3-$CF_3$ |
| Cl | 3-$OCF_3$ |
| Cl | 3-$OCF_2H$ |
| Cl | 3-$OCF_2CF_3H$ |
| Cl | 3-$OCH_2CF_3$ |
| Cl | 3-$SCF_3$ |
| Cl | 3-$SOCF_3$ |
| Cl | 3-$SO_2CF_3$ |
| Cl | 3-$SCF_2H$ |
| Cl | 3-$SOCF_2H$ |
| Cl | 3-$SO_2CF_2H$ |
| Cl | 4-$CF_3$ |
| Cl | 4-$OCF_3$ |
| Cl | 4-$OCF_2H$ |
| Cl | 4-$OCF_2CF_3H$ |
| Cl | 4-$OCH_2CF_3$ |
| Cl | 4-$SCF_3$ |
| Cl | 4-$SOCF_3$ |

TABLE 11-continued

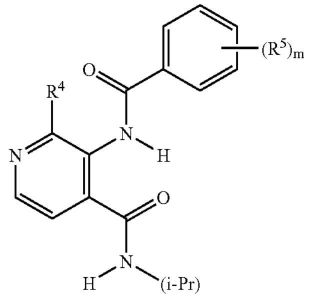

| $R^4$ | $(R^5)_m$ |
|---|---|
| Cl | 4-$SO_2CF_3$ |
| Cl | 4-$SCF_2H$ |
| Cl | 4-$SOCF_2H$ |
| Cl | 4-$SO_2CF_2H$ |
| F | 2-$CF_3$ |
| F | 2-$OCF_3$ |
| F | 2-$OCF_2H$ |
| F | 2-$OCF_2CF_2H$ |
| F | 2-$OCH_2CF_3$ |
| F | 2-$SCF_3$ |
| F | 2-$SOCF_3$ |
| F | 2-$SO_2CF_3$ |
| F | 2-$SCF_2H$ |
| F | 2-$SOCF_2H$ |
| F | 2-$SO_2CF_2H$ |
| F | 3-$CF_3$ |
| F | 3-$OCF_3$ |
| F | 3-$OCF_2H$ |
| F | 3-$OCF_2CF_3H$ |
| F | 3-$OCH_2CF_3$ |
| F | 3-$SCF_3$ |
| F | 3-$SOCF_3$ |
| F | 3-$SO_2CF_3$ |
| F | 3-$SCF_2H$ |
| F | 3-$SOCF_2H$ |
| F | 3-$SO_2CF_2H$ |
| F | 4-$CF_3$ |
| F | 4-$OCF_3$ |
| F | 4-$OCF_2H$ |
| F | 4-$OCF_2CF_3H$ |
| F | 4-$OCH_2CF_3$ |
| F | 4-$SCF_3$ |
| F | 4-$SOCF_3$ |
| F | 4-$SO_2CF_3$ |
| F | 4-$SCF_2H$ |
| F | 4-$SOCF_2H$ |
| F | 4-$SO_2CF_2H$ |
| Br | 2-$CF_3$ |
| Br | 2-$OCF_3$ |
| Br | 2-$OCF_2H$ |
| Br | 2-$OCF_2CF_2H$ |
| Br | 2-$OCH_2CF_3$ |
| Br | 2-$SCF_3$ |
| Br | 2-$SOCF_3$ |
| Br | 2-$SO_2CF_3$ |
| Br | 2-$SCF_2H$ |
| Br | 2-$SOCF_2H$ |
| Br | 2-$SO_2CF_2H$ |
| Br | 3-$CF_3$ |
| Br | 3-$OCF_3$ |
| Br | 3-$OCF_2H$ |
| Br | 3-$OCF_2CF_3H$ |
| Br | 3-$OCH_2CF_3$ |
| Br | 3-$SCF_3$ |
| Br | 3-$SOCF_3$ |
| Br | 3-$SO_2CF_3$ |
| Br | 3-$SCF_2H$ |
| Br | 3-$SOCF_2H$ |
| Br | 3-$SO_2CF_2H$ |
| Br | 4-$CF_3$ |
| Br | 4-$OCF_3$ |
| Br | 4-$OCF_2H$ |

TABLE 11-continued

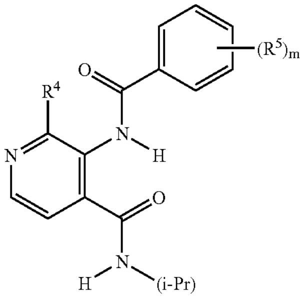

| $R^4$ | $(R^5)_m$ |
|---|---|
| Br | 4-$OCF_2CF_3H$ |
| Br | 4-$OCH_2CF_3$ |
| Br | 4-$SCF_3$ |
| Br | 4-$SOCF_3$ |
| Br | 4-$SO_2CF_3$ |
| Br | 4-$SCF_2H$ |
| Br | 4-$SOCF_2H$ |
| Br | 4-$SO_2CF_2H$ |
| I | 2-$CF_3$ |
| I | 2-$OCF_3$ |
| I | 2-$OCF_2H$ |
| I | 2-$OCF_2CF_2H$ |
| I | 2-$OCH_2CF_3$ |
| I | 2-$SCF_3$ |
| I | 2-$SOCF_3$ |
| I | 2-$SO_2CF_3$ |
| I | 2-$SCF_2H$ |
| I | 2-$SOCF_2H$ |
| I | 2-$SO_2CF_2H$ |
| I | 3-$CF_3$ |
| I | 3-$OCF_3$ |
| I | 3-$OCF_2H$ |
| I | 3-$OCF_2CF_3H$ |
| I | 3-$OCH_2CF_3$ |
| I | 3-$SCF_3$ |
| I | 3-$SOCF_3$ |
| I | 3-$SO_2CF_3$ |
| I | 3-$SCF_2H$ |
| I | 3-$SOCF_2H$ |
| I | 3-$SO_2CF_2H$ |
| I | 4-$CF_3$ |
| I | 4-$OCF_3$ |
| I | 4-$OCF_2H$ |
| I | 4-$OCF_2CF_3H$ |
| I | 4-$OCH_2CF_3$ |
| I | 4-$SCF_3$ |
| I | 4-$SOCF_3$ |
| I | 4-$SO_2CF_3$ |
| I | 4-$SCF_2H$ |
| I | 4-$SOCF_2H$ |
| I | 4-$SO_2CF_2H$ |
| OMe | 2-$CF_3$ |
| OMe | 2-$OCF_3$ |
| OMe | 2-$OCF_2H$ |
| OMe | 2-$OCF_2CF_2H$ |
| OMe | 2-$OCH_2CF_3$ |
| OMe | 2-$SCF_3$ |
| OMe | 2-$SOCF_3$ |
| OMe | 2-$SO_2CF_3$ |
| OMe | 2-$SCF_2H$ |
| OMe | 2-$SOCF_2H$ |
| OMe | 2-$SO_2CF_2H$ |
| OMe | 3-$CF_3$ |
| OMe | 3-$OCF_3$ |
| OMe | 3-$OCF_2H$ |
| OMe | 3-$OCF_2CF_3H$ |
| OMe | 3-$OCH_2CF_3$ |
| OMe | 3-$SCF_3$ |
| OMe | 3-$SOCF_3$ |
| OMe | 3-$SO_2CF_3$ |
| OMe | 3-$SCF_2H$ |
| OMe | 3-$SOCF_2H$ |

TABLE 11-continued

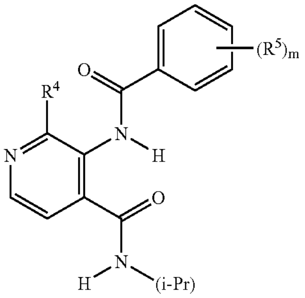

| $R^4$ | $(R^5)_m$ |
|---|---|
| OMe | 3-$SO_2CF_2H$ |
| OMe | 4-$CF_3$ |
| OMe | 4-$OCF_3$ |
| OMe | 4-$OCF_2H$ |
| OMe | 4-$OCF_2CF_3H$ |
| OMe | 4-$OCH_2CF_3$ |
| OMe | 4-$SCF_3$ |
| OMe | 4-$SOCF_3$ |
| OMe | 4-$SO_2CF_3$ |
| OMe | 4-$SCF_2H$ |
| OMe | 4-$SOCF_2H$ |
| OMe | 4-$SO_2CF_2H$ |
| $CF_3$ | 2-$CF_3$ |
| $CF_3$ | 2-$OCF_3$ |
| $CF_3$ | 2-$OCF_2H$ |
| $CF_3$ | 2-$OCF_2CF_2H$ |
| $CF_3$ | 2-$OCH_2CF_3$ |
| $CF_3$ | 2-$SCF_3$ |
| $CF_3$ | 2-$SOCF_3$ |
| $CF_3$ | 2-$SO_2CF_3$ |
| $CF_3$ | 2-$SCF_2H$ |
| $CF_3$ | 2-$SOCF_2H$ |
| $CF_3$ | 2-$SO_2CF_2H$ |
| $CF_3$ | 3-$CF_3$ |
| $CF_3$ | 3-$OCF_3$ |
| $CF_3$ | 3-$OCF_2H$ |
| $CF_3$ | 3-$OCF_2CF_3H$ |
| $CF_3$ | 3-$OCH_2CF_3$ |
| $CF_3$ | 3-$SCF_3$ |
| $CF_3$ | 3-$SOCF_3$ |
| $CF_3$ | 3-$SO_2CF_3$ |
| $CF_3$ | 3-$SCF_2H$ |
| $CF_3$ | 3-$SOCF_2H$ |
| $CF_3$ | 3-$SO_2CF_2H$ |
| $CF_3$ | 4-$CF_3$ |
| $CF_3$ | 4-$OCF_3$ |
| $CF_3$ | 4-$OCF_2H$ |
| $CF_3$ | 4-$OCF_2CF_3H$ |
| $CF_3$ | 4-$OCH_2CF_3$ |
| $CF_3$ | 4-$SCF_3$ |
| $CF_3$ | 4-$SOCF_3$ |
| $CF_3$ | 4-$SO_2CF_3$ |
| $CF_3$ | 4-$SCF_2H$ |
| $CF_3$ | 4-$SOCF_2H$ |
| $CF_3$ | 4-$SO_2CF_2H$ |
| $OCF_2H$ | 2-$CF_3$ |
| $OCF_2H$ | 2-$OCF_3$ |
| $OCF_2H$ | 2-$OCF_2H$ |
| $OCF_2H$ | 2-$OCF_2CF_2H$ |
| $OCF_2H$ | 2-$OCH_2CF_3$ |
| $OCF_2H$ | 2-$SCF_3$ |
| $OCF_2H$ | 2-$SOCF_3$ |
| $OCF_2H$ | 2-$SO_2CF_3$ |
| $OCF_2H$ | 2-$SCF_2H$ |
| $OCF_2H$ | 2-$SOCF_2H$ |
| $OCF_2H$ | 2-$SO_2CF_2H$ |
| $OCF_2H$ | 3-$CF_3$ |
| $OCF_2H$ | 3-$OCF_3$ |
| $OCF_2H$ | 3-$OCF_2H$ |
| $OCF_2H$ | 3-$OCF_2CF_3H$ |
| $OCF_2H$ | 3-$OCH_2CF_3$ |
| $OCF_2H$ | 3-$SCF_3$ |

TABLE 11-continued

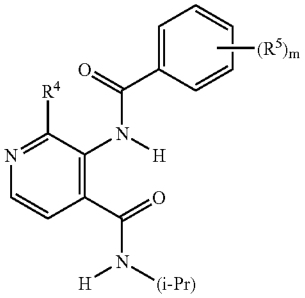

| $R^4$ | $(R^5)_m$ |
|---|---|
| $OCF_2H$ | 3-$SOCF_3$ |
| $OCF_2H$ | 3-$SO_2CF_3$ |
| $OCF_2H$ | 3-$SCF_2H$ |
| $OCF_2H$ | 3-$SOCF_2H$ |
| $OCF_2H$ | 3-$SO_2CF_2H$ |
| $OCF_2H$ | 4-$CF_3$ |
| $OCF_2H$ | 4-$OCF_3$ |
| $OCF_2H$ | 4-$OCF_2H$ |
| $OCF_2H$ | 4-$OCF_2CF_3H$ |
| $OCF_2H$ | 4-$OCH_2CF_3$ |
| $OCF_2H$ | 4-$SCF_3$ |
| $OCF_2H$ | 4-$SOCF_3$ |
| $OCF_2H$ | 4-$SO_2CF_3$ |
| $OCF_2H$ | 4-$SCF_2H$ |
| $OCF_2H$ | 4-$SOCF_2H$ |
| $OCF_2H$ | 4-$SO_2CF_2H$ |
| Me | 2-Me-4-$CF_3$ |
| Me | 2-Me-4-$OCF_3$ |
| Me | 2-Me-4-$OCF_2H$ |
| Me | 2-Me-4-$OCH_2CF_3$ |
| Me | 2-Me-4-$SCF_3$ |
| Me | 2-Me-4-$SOCF_3$ |
| Me | 2-Me-4-$SO_2CF_3$ |
| Me | 2-Me-4-$SCF_2H$ |
| Me | 2-Me-4-$SOCF_2H$ |
| Me | 2-Me-4-$SO_2CF_2H$ |
| Br | 2-Me-4-$CF_3$ |
| Br | 2-Me-4-$OCF_3$ |
| Br | 2-Me-4-$OCF_2H$ |
| Br | 2-Me-4-$OCH_2CF_3$ |
| Br | 2-Me-4-$SCF_3$ |
| Br | 2-Me-4-$SOCF_3$ |
| Br | 2-Me-4-$SO_2CF_3$ |
| Br | 2-Me-4-$SCF_2H$ |
| Br | 2-Me-4-$SOCF_2H$ |
| Br | 2-Me-4-$SO_2CF_2H$ |
| $CF_3$ | 2-Me-4-$CF_3$ |
| $CF_3$ | 2-Me-4-$OCF_3$ |
| $CF_3$ | 2-Me-4-$OCF_2H$ |
| $CF_3$ | 2-Me-4-$OCH_2CF_3$ |
| $CF_3$ | 2-Me-4-$SCF_3$ |
| $CF_3$ | 2-Me-4-$SOCF_3$ |
| $CF_3$ | 2-Me-4-$SO_2CF_3$ |
| $CF_3$ | 2-Me-4-$SCF_2H$ |
| $CF_3$ | 2-Me-4-$SOCF_2H$ |
| $CF_3$ | 2-Me-4-$SO_2CF_2H$ |
| F | 2-Me-4-$CF_3$ |
| F | 2-Me-4-$OCF_3$ |
| F | 2-Me-4-$OCF_2H$ |
| F | 2-Me-4-$OCH_2CF_3$ |
| F | 2-Me-4-$SCF_3$ |
| F | 2-Me-4-$SOCF_3$ |
| F | 2-Me-4-$SO_2CF_3$ |
| F | 2-Me-4-$SCF_2H$ |
| F | 2-Me-4-$SOCF_2H$ |
| F | 2-Me-4-$SO_2CF_2H$ |
| I | 2-Me-4-$CF_3$ |
| I | 2-Me-4-$OCF_3$ |
| I | 2-Me-4-$OCF_2H$ |
| I | 2-Me-4-$OCH_2CF_3$ |
| I | 2-Me-4-$SCF_3$ |
| I | 2-Me-4-$SOCF_3$ |

TABLE 11-continued

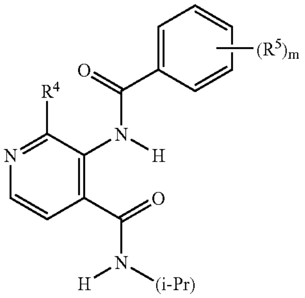

| $R^4$ | $(R^5)_m$ |
|---|---|
| I | 2-Me-4-$SO_2CF_3$ |
| I | 2-Me-4-$SCF_2H$ |
| I | 2-Me-4-$SOCF_2H$ |
| I | 2-Me-4-$SO_2CF_2H$ |
| $NO_2$ | 2-Me-4-$CF_3$ |
| $NO_2$ | 2-Me-4-$OCF_3$ |
| $NO_2$ | 2-Me-4-$OCF_2H$ |
| $NO_2$ | 2-Me-4-$OCH_2CF_3$ |
| $NO_2$ | 2-Me-4-$SCF_3$ |
| $NO_2$ | 2-Me-4-$SOCF_3$ |
| $NO_2$ | 2-Me-4-$SO_2CF_3$ |
| $NO_2$ | 2-Me-4-$SCF_2H$ |
| $NO_2$ | 2-Me-4-$SOCF_2H$ |
| $NO_2$ | 2-Me-4-$SO_2CF_2H$ |
| Cl | 2-Me-4-$CF_3$ |
| Cl | 2-Me-4-$OCF_3$ |
| Cl | 2-Me-4-$OCF_2H$ |
| Cl | 2-Me-4-$OCH_2CF_3$ |
| Cl | 2-Me-4-$SCF_3$ |
| Cl | 2-Me-4-$SOCF_3$ |
| Cl | 2-Me-4-$SO_2CF_3$ |
| Cl | 2-Me-4-$SCF_2H$ |
| Cl | 2-Me-4-$SOCF_2H$ |
| Cl | 2-Me-4-$SO_2CF_2H$ |
| OMe | 2-Me-4-$CF_3$ |
| OMe | 2-Me-4-$OCF_3$ |
| OMe | 2-Me-4-$OCF_2H$ |
| OMe | 2-Me-4-$OCH_2CF_3$ |
| OMe | 2-Me-4-$SCF_3$ |
| OMe | 2-Me-4-$SOCF_3$ |
| OMe | 2-Me-4-$SO_2CF_3$ |
| OMe | 2-Me-4-$SCF_2H$ |
| OMe | 2-Me-4-$SOCF_2H$ |
| OMe | 2-Me-4-$SO_2CF_2H$ |
| SMe | 2-Me-4-$CF_3$ |
| SMe | 2-Me-4-$OCF_3$ |
| SMe | 2-Me-4-$OCF_2H$ |
| SMe | 2-Me-4-$OCH_2CF_3$ |
| SMe | 2-Me-4-$SCF_3$ |
| SMe | 2-Me-4-$SOCF_3$ |
| SMe | 2-Me-4-$SO_2CF_3$ |
| SMe | 2-Me-4-$SCF_2H$ |
| SMe | 2-Me-4-$SOCF_2H$ |
| SMe | 2-Me-4-$SO_2CF_2H$ |

TABLE 12

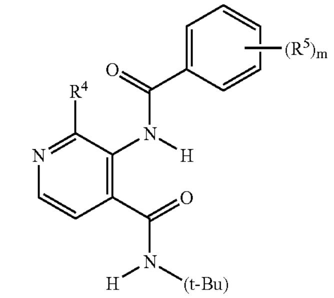

| $R^4$ | $(R^5)_m$ |
|---|---|
| Me | 2-$CF_3$ |
| Me | 2-$OCF_3$ |
| Me | 2-$OCF_2H$ |
| Me | 2-$OCF_2CF_2H$ |
| Me | 2-$OCH_2CF_3$ |
| Me | 2-$SCF_3$ |
| Me | 2-$SOCF_3$ |
| Me | 2-$SO_2CF_3$ |
| Me | 2-$SCF_2H$ |
| Me | 2-$SOCF_2H$ |
| Me | 2-$SO_2CF_2H$ |
| Me | 3-$CF_3$ |
| Me | 3-$OCF_3$ |
| Me | 3-$OCF_2H$ |
| Me | 3-$OCF_2CF_3H$ |
| Me | 3-$OCH_2CF_3$ |
| Me | 3-$SCF_3$ |
| Me | 3-$SOCF_3$ |
| Me | 3-$SO_2CF_3$ |
| Me | 3-$SCF_2H$ |
| Me | 3-$SOCF_2H$ |
| Me | 3-$SO_2CF_2H$ |
| Me | 4-$CF_3$ |
| Me | 4-$OCF_3$ |
| Me | 4-$OCF_2H$ |
| Me | 4-$OCF_2CF_3H$ |
| Me | 4-$OCH_2CF_3$ |
| Me | 4-$SCF_3$ |
| Me | 4-$SOCF_3$ |
| Me | 4-$SO_2CF_3$ |
| Me | 4-$SCF_2H$ |
| Me | 4-$SOCF_2H$ |
| Me | 4-$SO_2CF_2H$ |
| Cl | 2-$CF_3$ |
| Cl | 2-$OCF_3$ |
| Cl | 2-$OCF_2H$ |
| Cl | 2-$OCF_2CF_2H$ |
| Cl | 2-$OCH_2CF_3$ |
| Cl | 2-$SCF_3$ |
| Cl | 2-$SOCF_3$ |
| Cl | 2-$SO_2CF_3$ |
| Cl | 2-$SCF_2H$ |
| Cl | 2-$SOCF_2H$ |
| Cl | 2-$SO_2CF_2H$ |
| Cl | 3-$CF_3$ |
| Cl | 3-$OCF_3$ |
| Cl | 3-$OCF_2H$ |
| Cl | 3-$OCF_2CF_3H$ |
| Cl | 3-$OCH_2CF_3$ |
| Cl | 3-$SCF_3$ |
| Cl | 3-$SOCF_3$ |
| Cl | 3-$SO_2CF_3$ |
| Cl | 3-$SCF_2H$ |
| Cl | 3-$SOCF_2H$ |
| Cl | 3-$SO_2CF_2H$ |
| Cl | 4-$CF_3$ |
| Cl | 4-$OCF_3$ |
| Cl | 4-$OCF_2H$ |
| Cl | 4-$OCF_2CF_3H$ |
| Cl | 4-$OCH_2CF_3$ |
| Cl | 4-$SCF_3$ |
| Cl | 4-$SOCF_3$ |

TABLE 12-continued

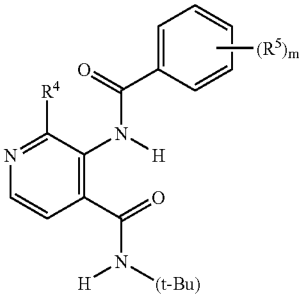

| $R^4$ | $(R^5)_m$ |
|---|---|
| Cl | 4-$SO_2CF_3$ |
| Cl | 4-$SCF_2H$ |
| Cl | 4-$SOCF_2H$ |
| Cl | 4-$SO_2CF_2H$ |
| F | 2-$CF_3$ |
| F | 2-$OCF_3$ |
| F | 2-$OCF_2H$ |
| F | 2-$OCF_2CF_2H$ |
| F | 2-$OCH_2CF_3$ |
| F | 2-$SCF_3$ |
| F | 2-$SOCF_3$ |
| F | 2-$SO_2CF_3$ |
| F | 2-$SCF_2H$ |
| F | 2-$SOCF_2H$ |
| F | 2-$SO_2CF_2H$ |
| F | 3-$CF_3$ |
| F | 3-$OCF_3$ |
| F | 3-$OCF_2H$ |
| F | 3-$OCF_2CF_3H$ |
| F | 3-$OCH_2CF_3$ |
| F | 3-$SCF_3$ |
| F | 3-$SOCF_3$ |
| F | 3-$SO_2CF_3$ |
| F | 3-$SCF_2H$ |
| F | 3-$SOCF_2H$ |
| F | 3-$SO_2CF_2H$ |
| F | 4-$CF_3$ |
| F | 4-$OCF_3$ |
| F | 4-$OCF_2H$ |
| F | 4-$OCF_2CF_3H$ |
| F | 4-$OCH_2CF_3$ |
| F | 4-$SCF_3$ |
| F | 4-$SOCF_3$ |
| F | 4-$SO_2CF_3$ |
| F | 4-$SCF_2H$ |
| F | 4-$SOCF_2H$ |
| F | 4-$SO_2CF_2H$ |
| Br | 2-$CF_3$ |
| Br | 2-$OCF_3$ |
| Br | 2-$OCF_2H$ |
| Br | 2-$OCF_2CF_2H$ |
| Br | 2-$OCH_2CF_3$ |
| Br | 2-$SCF_3$ |
| Br | 2-$SOCF_3$ |
| Br | 2-$SO_2CF_3$ |
| Br | 2-$SCF_2H$ |
| Br | 2-$SOCF_2H$ |
| Br | 2-$SO_2CF_2H$ |
| Br | 3-$CF_3$ |
| Br | 3-$OCF_3$ |
| Br | 3-$OCF_2H$ |
| Br | 3-$OCF_2CF_3H$ |
| Br | 3-$OCH_2CF_3$ |
| Br | 3-$SCF_3$ |
| Br | 3-$SOCF_3$ |
| Br | 3-$SO_2CF_3$ |
| Br | 3-$SCF_2H$ |
| Br | 3-$SOCF_2H$ |
| Br | 3-$SO_2CF_2H$ |
| Br | 4-$CF_3$ |
| Br | 4-$OCF_3$ |
| Br | 4-$OCF_2H$ |

TABLE 12-continued

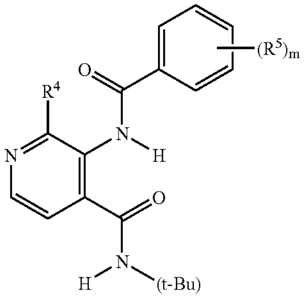

| $R^4$ | $(R^5)_m$ |
|---|---|
| Br | 4-$OCF_2CF_3H$ |
| Br | 4-$OCH_2CF_3$ |
| Br | 4-$SCF_3$ |
| Br | 4-$SOCF_3$ |
| Br | 4-$SO_2CF_3$ |
| Br | 4-$SCF_2H$ |
| Br | 4-$SOCF_2H$ |
| Br | 4-$SO_2CF_2H$ |
| I | 2-$CF_3$ |
| I | 2-$OCF_3$ |
| I | 2-$OCF_2H$ |
| I | 2-$OCF_2CF_2H$ |
| I | 2-$OCH_2CF_3$ |
| I | 2-$SCF_3$ |
| I | 2-$SOCF_3$ |
| I | 2-$SO_2CF_3$ |
| I | 2-$SCF_2H$ |
| I | 2-$SOCF_2H$ |
| I | 2-$SO_2CF_2H$ |
| I | 3-$CF_3$ |
| I | 3-$OCF_3$ |
| I | 3-$OCF_2H$ |
| I | 3-$OCF_2CF_3H$ |
| I | 3-$OCH_2CF_3$ |
| I | 3-$SCF_3$ |
| I | 3-$SOCF_3$ |
| I | 3-$SO_2CF_3$ |
| I | 3-$SCF_2H$ |
| I | 3-$SOCF_2H$ |
| I | 3-$SO_2CF_2H$ |
| I | 4-$CF_3$ |
| I | 4-$OCF_3$ |
| I | 4-$OCF_2H$ |
| I | 4-$OCF_2CF_3H$ |
| I | 4-$OCH_2CF_3$ |
| I | 4-$SCF_3$ |
| I | 4-$SOCF_3$ |
| I | 4-$SO_2CF_3$ |
| I | 4-$SCF_2H$ |
| I | 4-$SOCF_2H$ |
| I | 4-$SO_2CF_2H$ |
| OMe | 2-$CF_3$ |
| OMe | 2-$OCF_3$ |
| OMe | 2-$OCF_2H$ |
| OMe | 2-$OCF_2CF_2H$ |
| OMe | 2-$OCH_2CF_3$ |
| OMe | 2-$SCF_3$ |
| OMe | 2-$SOCF_3$ |
| OMe | 2-$SO_2CF_3$ |
| OMe | 2-$SCF_2H$ |
| OMe | 2-$SOCF_2H$ |
| OMe | 2-$SO_2CF_2H$ |
| OMe | 3-$CF_3$ |
| OMe | 3-$OCF_3$ |
| OMe | 3-$OCF_2H$ |
| OMe | 3-$OCF_2CF_3H$ |
| OMe | 3-$OCH_2CF_3$ |
| OMe | 3-$SCF_3$ |
| OMe | 3-$SOCF_3$ |
| OMe | 3-$SO_2CF_3$ |
| OMe | 3-$SCF_2H$ |
| OMe | 3-$SOCF_2H$ |

TABLE 12-continued

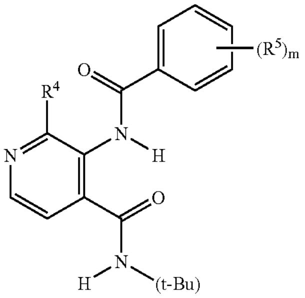

| $R^4$ | $(R^5)_m$ |
|---|---|
| OMe | 3-$SO_2CF_2H$ |
| OMe | 4-$CF_3$ |
| OMe | 4-$OCF_3$ |
| OMe | 4-$OCF_2H$ |
| OMe | 4-$OCF_2CF_3H$ |
| OMe | 4-$OCH_2CF_3$ |
| OMe | 4-$SCF_3$ |
| OMe | 4-$SOCF_3$ |
| OMe | 4-$SO_2CF_3$ |
| OMe | 4-$SCF_2H$ |
| OMe | 4-$SOCF_2H$ |
| OMe | 4-$SO_2CF_2H$ |
| $CF_3$ | 2-$CF_3$ |
| $CF_3$ | 2-$OCF_3$ |
| $CF_3$ | 2-$OCF_2H$ |
| $CF_3$ | 2-$OCF_2CF_2H$ |
| $CF_3$ | 2-$OCH_2CF_3$ |
| $CF_3$ | 2-$SCF_3$ |
| $CF_3$ | 2-$SOCF_3$ |
| $CF_3$ | 2-$SO_2CF_3$ |
| $CF_3$ | 2-$SCF_2H$ |
| $CF_3$ | 2-$SOCF_2H$ |
| $CF_3$ | 2-$SO_2CF_2H$ |
| $CF_3$ | 3-$CF_3$ |
| $CF_3$ | 3-$OCF_3$ |
| $CF_3$ | 3-$OCF_2H$ |
| $CF_3$ | 3-$OCF_2CF_3H$ |
| $CF_3$ | 3-$OCH_2CF_3$ |
| $CF_3$ | 3-$SCF_3$ |
| $CF_3$ | 3-$SOCF_3$ |
| $CF_3$ | 3-$SO_2CF_3$ |
| $CF_3$ | 3-$SCF_2H$ |
| $CF_3$ | 3-$SOCF_2H$ |
| $CF_3$ | 3-$SO_2CF_2H$ |
| $CF_3$ | 4-$CF_3$ |
| $CF_3$ | 4-$OCF_3$ |
| $CF_3$ | 4-$OCF_2H$ |
| $CF_3$ | 4-$OCF_2CF_3H$ |
| $CF_3$ | 4-$OCH_2CF_3$ |
| $CF_3$ | 4-$SCF_3$ |
| $CF_3$ | 4-$SOCF_3$ |
| $CF_3$ | 4-$SO_2CF_3$ |
| $CF_3$ | 4-$SCF_2H$ |
| $CF_3$ | 4-$SOCF_2H$ |
| $CF_3$ | 4-$SO_2CF_2H$ |
| $OCF_2H$ | 2-$CF_3$ |
| $OCF_2H$ | 2-$OCF_3$ |
| $OCF_2H$ | 2-$OCF_2H$ |
| $OCF_2H$ | 2-$OCF_2CF_2H$ |
| $OCF_2H$ | 2-$OCH_2CF_3$ |
| $OCF_2H$ | 2-$SCF_3$ |
| $OCF_2H$ | 2-$SOCF_3$ |
| $OCF_2H$ | 2-$SO_2CF_3$ |
| $OCF_2H$ | 2-$SCF_2H$ |
| $OCF_2H$ | 2-$SOCF_2H$ |
| $OCF_2H$ | 2-$SO_2CF_2H$ |
| $OCF_2H$ | 3-$CF_3$ |
| $OCF_2H$ | 3-$OCF_3$ |
| $OCF_2H$ | 3-$OCF_2H$ |
| $OCF_2H$ | 3-$OCF_2CF_3H$ |
| $OCF_2H$ | 3-$OCH_2CF_3$ |
| $OCF_2H$ | 3-$SCF_3$ |

TABLE 12-continued

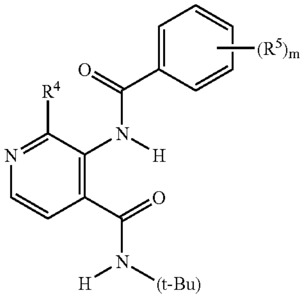

| $R^4$ | $(R^5)_m$ |
|---|---|
| $OCF_2H$ | 3-$SOCF_3$ |
| $OCF_2H$ | 3-$SO_2CF_3$ |
| $OCF_2H$ | 3-$SCF_2H$ |
| $OCF_2H$ | 3-$SOCF_2H$ |
| $OCF_2H$ | 3-$SO_2CF_2H$ |
| $OCF_2H$ | 4-$CF_3$ |
| $OCF_2H$ | 4-$OCF_3$ |
| $OCF_2H$ | 4-$OCF_2H$ |
| $OCF_2H$ | 4-$OCF_2CF_3H$ |
| $OCF_2H$ | 4-$OCH_2CF_3$ |
| $OCF_2H$ | 4-$SCF_3$ |
| $OCF_2H$ | 4-$SOCF_3$ |
| $OCF_2H$ | 4-$SO_2CF_3$ |
| $OCF_2H$ | 4-$SCF_2H$ |
| $OCF_2H$ | 4-$SOCF_2H$ |
| $OCF_2H$ | 4-$SO_2CF_2H$ |
| Me | 2-Me-4-$CF_3$ |
| Me | 2-Me-4-$OCF_3$ |
| Me | 2-Me-4-$OCF_2H$ |
| Me | 2-Me-4-$OCH_2CF_3$ |
| Me | 2-Me-4-$SCF_3$ |
| Me | 2-Me-4-$SOCF_3$ |
| Me | 2-Me-4-$SO_2CF_3$ |
| Me | 2-Me-4-$SCF_2H$ |
| Me | 2-Me-4-$SOCF_2H$ |
| Me | 2-Me-4-$SO_2CF_2H$ |
| Br | 2-Me-4-$CF_3$ |
| Br | 2-Me-4-$OCF_3$ |
| Br | 2-Me-4-$OCF_2H$ |
| Br | 2-Me-4-$OCH_2CF_3$ |
| Br | 2-Me-4-$SCF_3$ |
| Br | 2-Me-4-$SOCF_3$ |
| Br | 2-Me-4-$SO_2CF_3$ |
| Br | 2-Me-4-$SCF_2H$ |
| Br | 2-Me-4-$SOCF_2H$ |
| Br | 2-Me-4-$SO_2CF_2H$ |
| $CF_3$ | 2-Me-4-$CF_3$ |
| $CF_3$ | 2-Me-4-$OCF_3$ |
| $CF_3$ | 2-Me-4-$OCF_2H$ |
| $CF_3$ | 2-Me-4-$OCH_2CF_3$ |
| $CF_3$ | 2-Me-4-$SCF_3$ |
| $CF_3$ | 2-Me-4-$SOCF_3$ |
| $CF_3$ | 2-Me-4-$SO_2CF_3$ |
| $CF_3$ | 2-Me-4-$SCF_2H$ |
| $CF_3$ | 2-Me-4-$SOCF_2H$ |
| $CF_3$ | 2-Me-4-$SO_2CF_2H$ |
| F | 2-Me-4-$CF_3$ |
| F | 2-Me-4-$OCF_3$ |
| F | 2-Me-4-$OCF_2H$ |
| F | 2-Me-4-$OCH_2CF_3$ |
| F | 2-Me-4-$SCF_3$ |
| F | 2-Me-4-$SOCF_3$ |
| F | 2-Me-4-$SO_2CF_3$ |
| F | 2-Me-4-$SCF_2H$ |
| F | 2-Me-4-$SOCF_2H$ |
| F | 2-Me-4-$SO_2CF_2H$ |
| I | 2-Me-4-$CF_3$ |
| I | 2-Me-4-$OCF_3$ |
| I | 2-Me-4-$OCF_2H$ |
| I | 2-Me-4-$OCH_2CF_3$ |
| I | 2-Me-4-$SCF_3$ |
| I | 2-Me-4-$SOCF_3$ |

TABLE 12-continued

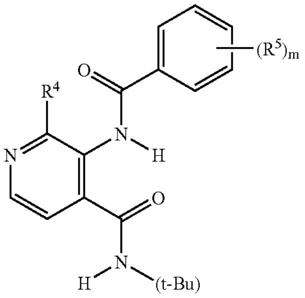

| $R^4$ | $(R^5)_m$ |
|---|---|
| I | 2-Me-4-$SO_2CF_3$ |
| I | 2-Me-4-$SCF_2H$ |
| I | 2-Me-4-$SOCF_2H$ |
| I | 2-Me-4-$SO_2CF_2H$ |
| $NO_2$ | 2-Me-4-$CF_3$ |
| $NO_2$ | 2-Me-4-$OCF_3$ |
| $NO_2$ | 2-Me-4-$OCF_2H$ |
| $NO_2$ | 2-Me-4-$OCH_2CF_3$ |
| $NO_2$ | 2-Me-4-$SCF_3$ |
| $NO_2$ | 2-Me-4-$SOCF_3$ |
| $NO_2$ | 2-Me-4-$SO_2CF_3$ |
| $NO_2$ | 2-Me-4-$SCF_2H$ |
| $NO_2$ | 2-Me-4-$SOCF_2H$ |
| $NO_2$ | 2-Me-4-$SO_2CF_2H$ |
| Cl | 2-Me-4-$CF_3$ |
| Cl | 2-Me-4-$OCF_3$ |
| Cl | 2-Me-4-$OCF_2H$ |
| Cl | 2-Me-4-$OCH_2CF_3$ |
| Cl | 2-Me-4-$SCF_3$ |
| Cl | 2-Me-4-$SOCF_3$ |
| Cl | 2-Me-4-$SO_2CF_3$ |
| Cl | 2-Me-4-$SCF_2H$ |
| Cl | 2-Me-4-$SOCF_2H$ |
| Cl | 2-Me-4-$SO_2CF_2H$ |
| OMe | 2-Me-4-$CF_3$ |
| OMe | 2-Me-4-$OCF_3$ |
| OMe | 2-Me-4-$OCF_2H$ |
| OMe | 2-Me-4-$OCH_2CF_3$ |
| OMe | 2-Me-4-$SCF_3$ |
| OMe | 2-Me-4-$SOCF_3$ |
| OMe | 2-Me-4-$SO_2CF_3$ |
| OMe | 2-Me-4-$SCF_2H$ |
| OMe | 2-Me-4-$SOCF_2H$ |
| OMe | 2-Me-4-$SO_2CF_2H$ |
| SMe | 2-Me-4-$CF_3$ |
| SMe | 2-Me-4-$OCF_3$ |
| SMe | 2-Me-4-$OCF_2H$ |
| SMe | 2-Me-4-$OCH_2CF_3$ |
| SMe | 2-Me-4-$SCF_3$ |
| SMe | 2-Me-4-$SOCF_3$ |
| SMe | 2-Me-4-$SO_2CF_3$ |
| SMe | 2-Me-4-$SCF_2H$ |
| SMe | 2-Me-4-$SOCF_2H$ |
| SMe | 2-Me-4-$SO_2CF_2H$ |

TABLE 13

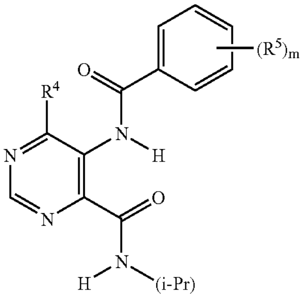

TABLE 13-continued

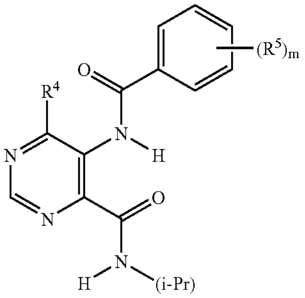

| $R^4$ | $(R^5)_m$ |
|---|---|
| Me | $2\text{-}CF_3$ |
| Me | $2\text{-}OCF_3$ |
| Me | $2\text{-}OCF_2H$ |
| Me | $2\text{-}OCF_2CF_2H$ |
| Me | $2\text{-}OCH_2CF_3$ |
| Me | $2\text{-}SCF_3$ |
| Me | $2\text{-}SOCF_3$ |
| Me | $2\text{-}SO_2CF_3$ |
| Me | $2\text{-}SCF_2H$ |
| Me | $2\text{-}SOCF_2H$ |
| Me | $2\text{-}SO_2CF_2H$ |
| Me | $3\text{-}CF_3$ |
| Me | $3\text{-}OCF_3$ |
| Me | $3\text{-}OCF_2H$ |
| Me | $3\text{-}OCF_2CF_3H$ |
| Me | $3\text{-}OCH_2CF_3$ |
| Me | $3\text{-}SCF_3$ |
| Me | $3\text{-}SOCF_3$ |
| Me | $3\text{-}SO_2CF_3$ |
| Me | $3\text{-}SCF_2H$ |
| Me | $3\text{-}SOCF_2H$ |
| Me | $3\text{-}SO_2CF_2H$ |
| Me | $4\text{-}CF_3$ |
| Me | $4\text{-}OCF_3$ |
| Me | $4\text{-}OCF_2H$ |
| Me | $4\text{-}OCF_2CF_3H$ |
| Me | $4\text{-}OCH_2CF_3$ |
| Me | $4\text{-}SCF_3$ |
| Me | $4\text{-}SOCF_3$ |
| Me | $4\text{-}SO_2CF_3$ |
| Me | $4\text{-}SCF_2H$ |
| Me | $4\text{-}SOCF_2H$ |
| Me | $4\text{-}SO_2CF_2H$ |
| Cl | $2\text{-}CF_3$ |
| Cl | $2\text{-}OCF_3$ |
| Cl | $2\text{-}OCF_2H$ |
| Cl | $2\text{-}OCF_2CF_2H$ |
| Cl | $2\text{-}OCH_2CF_3$ |
| Cl | $2\text{-}SCF_3$ |
| Cl | $2\text{-}SOCF_3$ |
| Cl | $2\text{-}SO_2CF_3$ |
| Cl | $2\text{-}SCF_2H$ |
| Cl | $2\text{-}SOCF_2H$ |
| Cl | $2\text{-}SO_2CF_2H$ |
| Cl | $3\text{-}CF_3$ |
| Cl | $3\text{-}OCF_3$ |
| Cl | $3\text{-}OCF_2H$ |
| Cl | $3\text{-}OCF_2CF_3H$ |
| Cl | $3\text{-}OCH_2CF_3$ |
| Cl | $3\text{-}SCF_3$ |
| Cl | $3\text{-}SOCF_3$ |
| Cl | $3\text{-}SO_2CF_3$ |
| Cl | $3\text{-}SCF_2H$ |
| Cl | $3\text{-}SOCF_2H$ |
| Cl | $3\text{-}SO_2CF_2H$ |
| Cl | $4\text{-}CF_3$ |
| Cl | $4\text{-}OCF_3$ |
| Cl | $4\text{-}OCF_2H$ |
| Cl | $4\text{-}OCF_2CF_3H$ |
| Cl | $4\text{-}OCH_2CF_3$ |
| Cl | $4\text{-}SCF_3$ |
| Cl | $4\text{-}SOCF_3$ |
| Cl | $4\text{-}SO_2CF_3$ |
| Cl | $4\text{-}SCF_2H$ |
| Cl | $4\text{-}SOCF_2H$ |
| Cl | $4\text{-}SO_2CF_2H$ |
| F | $2\text{-}CF_3$ |
| F | $2\text{-}OCF_3$ |
| F | $2\text{-}OCF_2H$ |
| F | $2\text{-}OCF_2CF_2H$ |
| F | $2\text{-}OCH_2CF_3$ |
| F | $2\text{-}SCF_3$ |
| F | $2\text{-}SOCF_3$ |
| F | $2\text{-}SO_2CF_3$ |
| F | $2\text{-}SCF_2H$ |
| F | $2\text{-}SOCF_2H$ |
| F | $2\text{-}SO_2CF_2H$ |
| F | $3\text{-}CF_3$ |
| F | $3\text{-}OCF_3$ |
| F | $3\text{-}OCF_2H$ |
| F | $3\text{-}OCF_2CF_3H$ |
| F | $3\text{-}OCH_2CF_3$ |
| F | $3\text{-}SCF_3$ |
| F | $3\text{-}SOCF_3$ |
| F | $3\text{-}SO_2CF_3$ |
| F | $3\text{-}SCF_2H$ |
| F | $3\text{-}SOCF_2H$ |
| F | $3\text{-}SO_2CF_2H$ |
| F | $4\text{-}CF_3$ |
| F | $4\text{-}OCF_3$ |
| F | $4\text{-}OCF_2H$ |
| F | $4\text{-}OCF_2CF_3H$ |
| F | $4\text{-}OCH_2CF_3$ |
| F | $4\text{-}SCF_3$ |
| F | $4\text{-}SOCF_3$ |
| F | $4\text{-}SO_2CF_3$ |
| F | $4\text{-}SCF_2H$ |
| F | $4\text{-}SOCF_2H$ |
| F | $4\text{-}SO_2CF_2H$ |
| Br | $2\text{-}CF_3$ |
| Br | $2\text{-}OCF_3$ |
| Br | $2\text{-}OCF_2H$ |
| Br | $2\text{-}OCF_2CF_2H$ |
| Br | $2\text{-}OCH_2CF_3$ |
| Br | $2\text{-}SCF_3$ |
| Br | $2\text{-}SOCF_3$ |
| Br | $2\text{-}SO_2CF_3$ |
| Br | $2\text{-}SCF_2H$ |
| Br | $2\text{-}SOCF_2H$ |
| Br | $2\text{-}SO_2CF_2H$ |
| Br | $3\text{-}CF_3$ |
| Br | $3\text{-}OCF_3$ |
| Br | $3\text{-}OCF_2H$ |
| Br | $3\text{-}OCF_2CF_3H$ |
| Br | $3\text{-}OCH_2CF_3$ |
| Br | $3\text{-}SCF_3$ |
| Br | $3\text{-}SOCF_3$ |
| Br | $3\text{-}SO_2CF_3$ |
| Br | $3\text{-}SCF_2H$ |
| Br | $3\text{-}SOCF_2H$ |
| Br | $3\text{-}SO_2CF_2H$ |
| Br | $4\text{-}CF_3$ |
| Br | $4\text{-}OCF_3$ |
| Br | $4\text{-}OCF_2H$ |

TABLE 13-continued

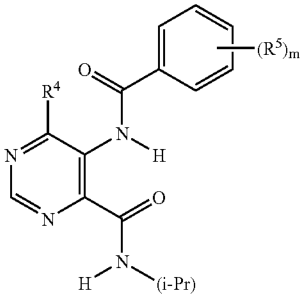

| $R^4$ | $(R^5)_m$ |
|---|---|
| Br | 4-$OCF_2CF_3H$ |
| Br | 4-$OCH_2CF_3$ |
| Br | 4-$SCF_3$ |
| Br | 4-$SOCF_3$ |
| Br | 4-$SO_2CF_3$ |
| Br | 4-$SCF_2H$ |
| Br | 4-$SOCF_2H$ |
| Br | 4-$SO_2CF_2H$ |
| I | 2-$CF_3$ |
| I | 2-$OCF_3$ |
| I | 2-$OCF_2H$ |
| I | 2-$OCF_2CF_2H$ |
| I | 2-$OCH_2CF_3$ |
| I | 2-$SCF_3$ |
| I | 2-$SOCF_3$ |
| I | 2-$SO_2CF_3$ |
| I | 2-$SCF_2H$ |
| I | 2-$SOCF_2H$ |
| I | 2-$SO_2CF_2H$ |
| I | 3-$CF_3$ |
| I | 3-$OCF_3$ |
| I | 3-$OCF_2H$ |
| I | 3-$OCF_2CF_3H$ |
| I | 3-$OCH_2CF_3$ |
| I | 3-$SCF_3$ |
| I | 3-$SOCF_3$ |
| I | 3-$SO_2CF_3$ |
| I | 3-$SCF_2H$ |
| I | 3-$SOCF_2H$ |
| I | 3-$SO_2CF_2H$ |
| I | 4-$CF_3$ |
| I | 4-$OCF_3$ |
| I | 4-$OCF_2H$ |
| I | 4-$OCF_2CF_3H$ |
| I | 4-$OCH_2CF_3$ |
| I | 4-$SCF_3$ |
| I | 4-$SOCF_3$ |
| I | 4-$SO_2CF_3$ |
| I | 4-$SCF_2H$ |
| I | 4-$SOCF_2H$ |
| I | 4-$SO_2CF_2H$ |
| OMe | 2-$CF_3$ |
| OMe | 2-$OCF_3$ |
| OMe | 2-$OCF_2H$ |
| OMe | 2-$OCF_2CF_2H$ |
| OMe | 2-$OCH_2CF_3$ |
| OMe | 2-$SCF_3$ |
| OMe | 2-$SOCF_3$ |
| OMe | 2-$SO_2CF_3$ |
| OMe | 2-$SCF_2H$ |
| OMe | 2-$SOCF_2H$ |
| OMe | 2-$SO_2CF_2H$ |
| OMe | 3-$CF_3$ |
| OMe | 3-$OCF_3$ |
| OMe | 3-$OCF_2H$ |
| OMe | 3-$OCF_2CF_3H$ |
| OMe | 3-$OCH_2CF_3$ |
| OMe | 3-$SCF_3$ |
| OMe | 3-$SOCF_3$ |
| OMe | 3-$SO_2CF_3$ |
| OMe | 3-$SCF_2H$ |
| OMe | 3-$SOCF_2H$ |

TABLE 13-continued

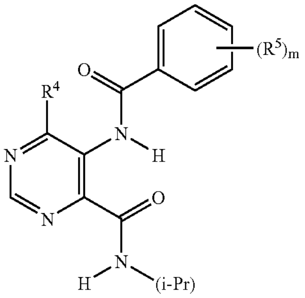

| $R^4$ | $(R^5)_m$ |
|---|---|
| OMe | 3-$SO_2CF_2H$ |
| OMe | 4-$CF_3$ |
| OMe | 4-$OCF_3$ |
| OMe | 4-$OCF_2H$ |
| OMe | 4-$OCF_2CF_3H$ |
| OMe | 4-$OCH_2CF_3$ |
| OMe | 4-$SCF_3$ |
| OMe | 4-$SOCF_3$ |
| OMe | 4-$SO_2CF_3$ |
| OMe | 4-$SCF_2H$ |
| OMe | 4-$SOCF_2H$ |
| OMe | 4-$SO_2CF_2H$ |
| $CF_3$ | 2-$CF_3$ |
| $CF_3$ | 2-$OCF_3$ |
| $CF_3$ | 2-$OCF_2H$ |
| $CF_3$ | 2-$OCF_2CF_2H$ |
| $CF_3$ | 2-$OCH_2CF_3$ |
| $CF_3$ | 2-$SCF_3$ |
| $CF_3$ | 2-$SOCF_3$ |
| $CF_3$ | 2-$SO_2CF_3$ |
| $CF_3$ | 2-$SCF_2H$ |
| $CF_3$ | 2-$SOCF_2H$ |
| $CF_3$ | 2-$SO_2CF_2H$ |
| $CF_3$ | 3-$CF_3$ |
| $CF_3$ | 3-$OCF_3$ |
| $CF_3$ | 3-$OCF_2H$ |
| $CF_3$ | 3-$OCF_2CF_3H$ |
| $CF_3$ | 3-$OCH_2CF_3$ |
| $CF_3$ | 3-$SCF_3$ |
| $CF_3$ | 3-$SOCF_3$ |
| $CF_3$ | 3-$SO_2CF_3$ |
| $CF_3$ | 3-$SCF_2H$ |
| $CF_3$ | 3-$SOCF_2H$ |
| $CF_3$ | 3-$SO_2CF_2H$ |
| $CF_3$ | 4-$CF_3$ |
| $CF_3$ | 4-$OCF_3$ |
| $CF_3$ | 4-$OCF_2H$ |
| $CF_3$ | 4-$OCF_2CF_3H$ |
| $CF_3$ | 4-$OCH_2CF_3$ |
| $CF_3$ | 4-$SCF_3$ |
| $CF_3$ | 4-$SOCF_3$ |
| $CF_3$ | 4-$SO_2CF_3$ |
| $CF_3$ | 4-$SCF_2H$ |
| $CF_3$ | 4-$SOCF_2H$ |
| $CF_3$ | 4-$SO_2CF_2H$ |
| $OCF_2H$ | 2-$CF_3$ |
| $OCF_2H$ | 2-$OCF_3$ |
| $OCF_2H$ | 2-$OCF_2H$ |
| $OCF_2H$ | 2-$OCF_2CF_2H$ |
| $OCF_2H$ | 2-$OCH_2CF_3$ |
| $OCF_2H$ | 2-$SCF_3$ |
| $OCF_2H$ | 2-$SOCF_3$ |
| $OCF_2H$ | 2-$SO_2CF_3$ |
| $OCF_2H$ | 2-$SCF_2H$ |
| $OCF_2H$ | 2-$SOCF_2H$ |
| $OCF_2H$ | 2-$SO_2CF_2H$ |
| $OCF_2H$ | 3-$CF_3$ |
| $OCF_2H$ | 3-$OCF_3$ |
| $OCF_2H$ | 3-$OCF_2H$ |
| $OCF_2H$ | 3-$OCF_2CF_3H$ |
| $OCF_2H$ | 3-$OCH_2CF_3$ |
| $OCF_2H$ | 3-$SCF_3$ |

TABLE 13-continued

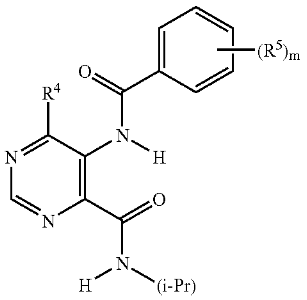

| $R^4$ | $(R^5)_m$ |
|---|---|
| $OCF_2H$ | 3-$SOCF_3$ |
| $OCF_2H$ | 3-$SO_2CF_3$ |
| $OCF_2H$ | 3-$SCF_2H$ |
| $OCF_2H$ | 3-$SOCF_2H$ |
| $OCF_2H$ | 3-$SO_2CF_2H$ |
| $OCF_2H$ | 4-$CF_3$ |
| $OCF_2H$ | 4-$OCF_3$ |
| $OCF_2H$ | 4-$OCF_2H$ |
| $OCF_2H$ | 4-$OCF_2CF_3H$ |
| $OCF_2H$ | 4-$OCH_2CF_3$ |
| $OCF_2H$ | 4-$SCF_3$ |
| $OCF_2H$ | 4-$SOCF_3$ |
| $OCF_2H$ | 4-$SO_2CF_3$ |
| $OCF_2H$ | 4-$SCF_2H$ |
| $OCF_2H$ | 4-$SOCF_2H$ |
| $OCF_2H$ | 4-$SO_2CF_2H$ |
| Me | 2-Me-4-$CF_3$ |
| Me | 2-Me-4-$OCF_3$ |
| Me | 2-Me-4-$OCF_2H$ |
| Me | 2-Me-4-$OCH_2CF_3$ |
| Me | 2-Me-4-$SCF_3$ |
| Me | 2-Me-4-$SOCF_3$ |
| Me | 2-Me-4-$SO_2CF_3$ |
| Me | 2-Me-4-$SCF_2H$ |
| Me | 2-Me-4-$SOCF_2H$ |
| Me | 2-Me-4-$SO_2CF_2H$ |
| Br | 2-Me-4-$CF_3$ |
| Br | 2-Me-4-$OCF_3$ |
| Br | 2-Me-4-$OCF_2H$ |
| Br | 2-Me-4-$OCH_2CF_3$ |
| Br | 2-Me-4-$SCF_3$ |
| Br | 2-Me-4-$SOCF_3$ |
| Br | 2-Me-4-$SO_2CF_3$ |
| Br | 2-Me-4-$SCF_2H$ |
| Br | 2-Me-4-$SOCF_2H$ |
| Br | 2-Me-4-$SO_2CF_2H$ |
| $CF_3$ | 2-Me-4-$CF_3$ |
| $CF_3$ | 2-Me-4-$OCF_3$ |
| $CF_3$ | 2-Me-4-$OCF_2H$ |
| $CF_3$ | 2-Me-4-$OCH_2CF_3$ |
| $CF_3$ | 2-Me-4-$SCF_3$ |
| $CF_3$ | 2-Me-4-$SOCF_3$ |
| $CF_3$ | 2-Me-4-$SO_2CF_3$ |
| $CF_3$ | 2-Me-4-$SCF_2H$ |
| $CF_3$ | 2-Me-4-$SOCF_2H$ |
| $CF_3$ | 2-Me-4-$SO_2CF_2H$ |
| F | 2-Me-4-$CF_3$ |
| F | 2-Me-4-$OCF_3$ |
| F | 2-Me-4-$OCF_2H$ |
| F | 2-Me-4-$OCH_2CF_3$ |
| F | 2-Me-4-$SCF_3$ |
| F | 2-Me-4-$SOCF_3$ |
| F | 2-Me-4-$SO_2CF_3$ |
| F | 2-Me-4-$SCF_2H$ |
| F | 2-Me-4-$SOCF_2H$ |
| F | 2-Me-4-$SO_2CF_2H$ |
| I | 2-Me-4-$CF_3$ |
| I | 2-Me-4-$OCF_3$ |
| I | 2-Me-4-$OCF_2H$ |
| I | 2-Me-4-$OCH_2CF_3$ |
| I | 2-Me-4-$SCF_3$ |
| I | 2-Me-4-$SOCF_3$ |

TABLE 13-continued

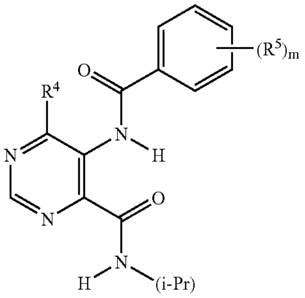

| $R^4$ | $(R^5)_m$ |
|---|---|
| I | 2-Me-4-$SO_2CF_3$ |
| I | 2-Me-4-$SCF_2H$ |
| I | 2-Me-4-$SOCF_2H$ |
| I | 2-Me-4-$SO_2CF_2H$ |
| $NO_2$ | 2-Me-4-$CF_3$ |
| $NO_2$ | 2-Me-4-$OCF_3$ |
| $NO_2$ | 2-Me-4-$OCF_2H$ |
| $NO_2$ | 2-Me-4-$OCH_2CF_3$ |
| $NO_2$ | 2-Me-4-$SCF_3$ |
| $NO_2$ | 2-Me-4-$SOCF_3$ |
| $NO_2$ | 2-Me-4-$SO_2CF_3$ |
| $NO_2$ | 2-Me-4-$SCF_2H$ |
| $NO_2$ | 2-Me-4-$SOCF_2H$ |
| $NO_2$ | 2-Me-4-$SO_2CF_2H$ |
| Cl | 2-Me-4-$CF_3$ |
| Cl | 2-Me-4-$OCF_3$ |
| Cl | 2-Me-4-$OCF_2H$ |
| Cl | 2-Me-4-$OCH_2CF_3$ |
| Cl | 2-Me-4-$SCF_3$ |
| Cl | 2-Me-4-$SOCF_3$ |
| Cl | 2-Me-4-$SO_2CF_3$ |
| Cl | 2-Me-4-$SCF_2H$ |
| Cl | 2-Me-4-$SOCF_2H$ |
| Cl | 2-Me-4-$SO_2CF_2H$ |
| OMe | 2-Me-4-$CF_3$ |
| OMe | 2-Me-4-$OCF_3$ |
| OMe | 2-Me-4-$OCF_2H$ |
| OMe | 2-Me-4-$OCH_2CF_3$ |
| OMe | 2-Me-4-$SCF_3$ |
| OMe | 2-Me-4-$SOCF_3$ |
| OMe | 2-Me-4-$SO_2CF_3$ |
| OMe | 2-Me-4-$SCF_2H$ |
| OMe | 2-Me-4-$SOCF_2H$ |
| OMe | 2-Me-4-$SO_2CF_2H$ |
| SMe | 2-Me-4-$CF_3$ |
| SMe | 2-Me-4-$OCF_3$ |
| SMe | 2-Me-4-$OCF_2H$ |
| SMe | 2-Me-4-$OCH_2CF_3$ |
| SMe | 2-Me-4-$SCF_3$ |
| SMe | 2-Me-4-$SOCF_3$ |
| SMe | 2-Me-4-$SO_2CF_3$ |
| SMe | 2-Me-4-$SCF_2H$ |
| SMe | 2-Me-4-$SOCF_2H$ |
| SMe | 2-Me-4-$SO_2CF_2H$ |

TABLE 14

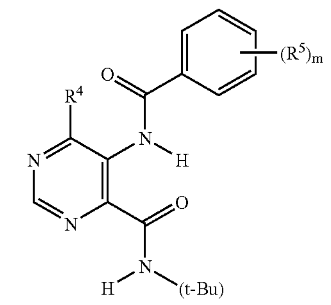

| $R^4$ | $(R^5)_m$ |
|---|---|
| Me | 2-$CF_3$ |
| Me | 2-$OCF_3$ |
| Me | 2-$OCF_2H$ |
| Me | 2-$OCF_2CF_2H$ |
| Me | 2-$OCH_2CF_3$ |
| Me | 2-$SCF_3$ |
| Me | 2-$SOCF_3$ |
| Me | 2-$SO_2CF_3$ |
| Me | 2-$SCF_2H$ |
| Me | 2-$SOCF_2H$ |
| Me | 2-$SO_2CF_2H$ |
| Me | 3-$CF_3$ |
| Me | 3-$OCF_3$ |
| Me | 3-$OCF_2H$ |
| Me | 3-$OCF_2CF_3H$ |
| Me | 3-$OCH_2CF_3$ |
| Me | 3-$SCF_3$ |
| Me | 3-$SOCF_3$ |
| Me | 3-$SO_2CF_3$ |
| Me | 3-$SCF_2H$ |
| Me | 3-$SOCF_2H$ |
| Me | 3-$SO_2CF_2H$ |
| Me | 4-$CF_3$ |
| Me | 4-$OCF_3$ |
| Me | 4-$OCF_2H$ |
| Me | 4-$OCF_2CF_3H$ |
| Me | 4-$OCH_2CF_3$ |
| Me | 4-$SCF_3$ |
| Me | 4-$SOCF_3$ |
| Me | 4-$SO_2CF_3$ |
| Me | 4-$SCF_2H$ |
| Me | 4-$SOCF_2H$ |
| Me | 4-$SO_2CF_2H$ |
| Cl | 2-$CF_3$ |
| Cl | 2-$OCF_3$ |
| Cl | 2-$OCF_2H$ |
| Cl | 2-$OCF_2CF_2H$ |
| Cl | 2-$OCH_2CF_3$ |
| Cl | 2-$SCF_3$ |
| Cl | 2-$SOCF_3$ |
| Cl | 2-$SO_2CF_3$ |
| Cl | 2-$SCF_2H$ |
| Cl | 2-$SOCF_2H$ |
| Cl | 2-$SO_2CF_2H$ |
| Cl | 3-$CF_3$ |
| Cl | 3-$OCF_3$ |
| Cl | 3-$OCF_2H$ |
| Cl | 3-$OCF_2CF_3H$ |
| Cl | 3-$OCH_2CF_3$ |
| Cl | 3-$SCF_3$ |
| Cl | 3-$SOCF_3$ |
| Cl | 3-$SO_2CF_3$ |
| Cl | 3-$SCF_2H$ |
| Cl | 3-$SOCF_2H$ |
| Cl | 3-$SO_2CF_2H$ |
| Cl | 4-$CF_3$ |
| Cl | 4-$OCF_3$ |
| Cl | 4-$OCF_2H$ |
| Cl | 4-$OCF_2CF_3H$ |
| Cl | 4-$OCH_2CF_3$ |
| Cl | 4-$SCF_3$ |
| Cl | 4-$SOCF_3$ |

TABLE 14-continued

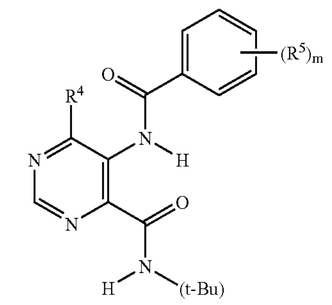

| $R^4$ | $(R^5)_m$ |
|---|---|
| Cl | 4-$SO_2CF_3$ |
| Cl | 4-$SCF_2H$ |
| Cl | 4-$SOCF_2H$ |
| Cl | 4-$SO_2CF_2H$ |
| F | 2-$CF_3$ |
| F | 2-$OCF_3$ |
| F | 2-$OCF_2H$ |
| F | 2-$OCF_2CF_2H$ |
| F | 2-$OCH_2CF_3$ |
| F | 2-$SCF_3$ |
| F | 2-$SOCF_3$ |
| F | 2-$SO_2CF_3$ |
| F | 2-$SCF_2H$ |
| F | 2-$SOCF_2H$ |
| F | 2-$SO_2CF_2H$ |
| F | 3-$CF_3$ |
| F | 3-$OCF_3$ |
| F | 3-$OCF_2H$ |
| F | 3-$OCF_2CF_3H$ |
| F | 3-$OCH_2CF_3$ |
| F | 3-$SCF_3$ |
| F | 3-$SOCF_3$ |
| F | 3-$SO_2CF_3$ |
| F | 3-$SCF_2H$ |
| F | 3-$SOCF_2H$ |
| F | 3-$SO_2CF_2H$ |
| F | 4-$CF_3$ |
| F | 4-$OCF_3$ |
| F | 4-$OCF_2H$ |
| F | 4-$OCF_2CF_3H$ |
| F | 4-$OCH_2CF_3$ |
| F | 4-$SCF_3$ |
| F | 4-$SOCF_3$ |
| F | 4-$SO_2CF_3$ |
| F | 4-$SCF_2H$ |
| F | 4-$SOCF_2H$ |
| F | 4-$SO_2CF_2H$ |
| Br | 2-$CF_3$ |
| Br | 2-$OCF_3$ |
| Br | 2-$OCF_2H$ |
| Br | 2-$OCF_2CF_2H$ |
| Br | 2-$OCH_2CF_3$ |
| Br | 2-$SCF_3$ |
| Br | 2-$SOCF_3$ |
| Br | 2-$SO_2CF_3$ |
| Br | 2-$SCF_2H$ |
| Br | 2-$SOCF_2H$ |
| Br | 2-$SO_2CF_2H$ |
| Br | 3-$CF_3$ |
| Br | 3-$OCF_3$ |
| Br | 3-$OCF_2H$ |
| Br | 3-$OCF_2CF_3H$ |
| Br | 3-$OCH_2CF_3$ |
| Br | 3-$SCF_3$ |
| Br | 3-$SOCF_3$ |
| Br | 3-$SO_2CF_3$ |
| Br | 3-$SCF_2H$ |
| Br | 3-$SOCF_2H$ |
| Br | 3-$SO_2CF_2H$ |
| Br | 4-$CF_3$ |
| Br | 4-$OCF_3$ |
| Br | 4-$OCF_2H$ |

TABLE 14-continued

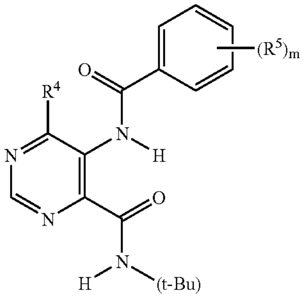

| $R^4$ | $(R^5)_m$ |
|---|---|
| Br | 4-$OCF_2CF_3H$ |
| Br | 4-$OCH_2CF_3$ |
| Br | 4-$SCF_3$ |
| Br | 4-$SOCF_3$ |
| Br | 4-$SO_2CF_3$ |
| Br | 4-$SCF_2H$ |
| Br | 4-$SOCF_2H$ |
| Br | 4-$SO_2CF_2H$ |
| I | 2-$CF_3$ |
| I | 2-$OCF_3$ |
| I | 2-$OCF_2H$ |
| I | 2-$OCF_2CF_2H$ |
| I | 2-$OCH_2CF_3$ |
| I | 2-$SCF_3$ |
| I | 2-$SOCF_3$ |
| I | 2-$SO_2CF_3$ |
| I | 2-$SCF_2H$ |
| I | 2-$SOCF_2H$ |
| I | 2-$SO_2CF_2H$ |
| I | 3-$CF_3$ |
| I | 3-$OCF_3$ |
| I | 3-$OCF_2H$ |
| I | 3-$OCF_2CF_3H$ |
| I | 3-$OCH_2CF_3$ |
| I | 3-$SCF_3$ |
| I | 3-$SOCF_3$ |
| I | 3-$SO_2CF_3$ |
| I | 3-$SCF_2H$ |
| I | 3-$SOCF_2H$ |
| I | 3-$SO_2CF_2H$ |
| I | 4-$CF_3$ |
| I | 4-$OCF_3$ |
| I | 4-$OCF_2H$ |
| I | 4-$OCF_2CF_3H$ |
| I | 4-$OCH_2CF_3$ |
| I | 4-$SCF_3$ |
| I | 4-$SOCF_3$ |
| I | 4-$SO_2CF_3$ |
| I | 4-$SCF_2H$ |
| I | 4-$SOCF_2H$ |
| I | 4-$SO_2CF_2H$ |
| OMe | 2-$CF_3$ |
| OMe | 2-$OCF_3$ |
| OMe | 2-$OCF_2H$ |
| OMe | 2-$OCF_2CF_2H$ |
| OMe | 2-$OCH_2CF_3$ |
| OMe | 2-$SCF_3$ |
| OMe | 2-$SOCF_3$ |
| OMe | 2-$SO_2CF_3$ |
| OMe | 2-$SCF_2H$ |
| OMe | 2-$SOCF_2H$ |
| OMe | 2-$SO_2CF_2H$ |
| OMe | 3-$CF_3$ |
| OMe | 3-$OCF_3$ |
| OMe | 3-$OCF_2H$ |
| OMe | 3-$OCF_2CF_3H$ |
| OMe | 3-$OCH_2CF_3$ |
| OMe | 3-$SCF_3$ |
| OMe | 3-$SOCF_3$ |
| OMe | 3-$SO_2CF_3$ |
| OMe | 3-$SCF_2H$ |
| OMe | 3-$SOCF_2H$ |

TABLE 14-continued

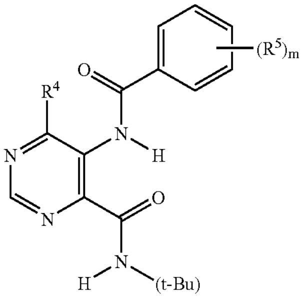

| $R^4$ | $(R^5)_m$ |
|---|---|
| OMe | 3-$SO_2CF_2H$ |
| OMe | 4-$CF_3$ |
| OMe | 4-$OCF_3$ |
| OMe | 4-$OCF_2H$ |
| OMe | 4-$OCF_2CF_3H$ |
| OMe | 4-$OCH_2CF_3$ |
| OMe | 4-$SCF_3$ |
| OMe | 4-$SOCF_3$ |
| OMe | 4-$SO_2CF_3$ |
| OMe | 4-$SCF_2H$ |
| OMe | 4-$SOCF_2H$ |
| OMe | 4-$SO_2CF_2H$ |
| $CF_3$ | 2-$CF_3$ |
| $CF_3$ | 2-$OCF_3$ |
| $CF_3$ | 2-$OCF_2H$ |
| $CF_3$ | 2-$OCF_2CF_2H$ |
| $CF_3$ | 2-$OCH_2CF_3$ |
| $CF_3$ | 2-$SCF_3$ |
| $CF_3$ | 2-$SOCF_3$ |
| $CF_3$ | 2-$SO_2CF_3$ |
| $CF_3$ | 2-$SCF_2H$ |
| $CF_3$ | 2-$SOCF_2H$ |
| $CF_3$ | 2-$SO_2CF_2H$ |
| $CF_3$ | 3-$CF_3$ |
| $CF_3$ | 3-$OCF_3$ |
| $CF_3$ | 3-$OCF_2H$ |
| $CF_3$ | 3-$OCF_2CF_3H$ |
| $CF_3$ | 3-$OCH_2CF_3$ |
| $CF_3$ | 3-$SCF_3$ |
| $CF_3$ | 3-$SOCF_3$ |
| $CF_3$ | 3-$SO_2CF_3$ |
| $CF_3$ | 3-$SCF_2H$ |
| $CF_3$ | 3-$SOCF_2H$ |
| $CF_3$ | 3-$SO_2CF_2H$ |
| $CF_3$ | 4-$CF_3$ |
| $CF_3$ | 4-$OCF_3$ |
| $CF_3$ | 4-$OCF_2H$ |
| $CF_3$ | 4-$OCF_2CF_3H$ |
| $CF_3$ | 4-$OCH_2CF_3$ |
| $CF_3$ | 4-$SCF_3$ |
| $CF_3$ | 4-$SOCF_3$ |
| $CF_3$ | 4-$SO_2CF_3$ |
| $CF_3$ | 4-$SCF_2H$ |
| $CF_3$ | 4-$SOCF_2H$ |
| $CF_3$ | 4-$SO_2CF_2H$ |
| $OCF_2H$ | 2-$CF_3$ |
| $OCF_2H$ | 2-$OCF_3$ |
| $OCF_2H$ | 2-$OCF_2H$ |
| $OCF_2H$ | 2-$OCF_2CF_2H$ |
| $OCF_2H$ | 2-$OCH_2CF_3$ |
| $OCF_2H$ | 2-$SCF_3$ |
| $OCF_2H$ | 2-$SOCF_3$ |
| $OCF_2H$ | 2-$SO_2CF_3$ |
| $OCF_2H$ | 2-$SCF_2H$ |
| $OCF_2H$ | 2-$SOCF_2H$ |
| $OCF_2H$ | 2-$SO_2CF_2H$ |
| $OCF_2H$ | 3-$CF_3$ |
| $OCF_2H$ | 3-$OCF_3$ |
| $OCF_2H$ | 3-$OCF_2H$ |
| $OCF_2H$ | 3-$OCF_2CF_3H$ |
| $OCF_2H$ | 3-$OCH_2CF_3$ |
| $OCF_2H$ | 3-$SCF_3$ |

TABLE 14-continued

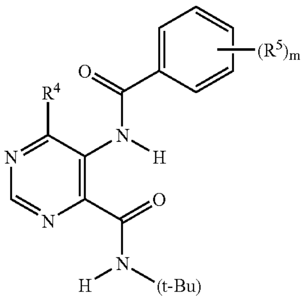

| $R^4$ | $(R^5)_m$ |
|---|---|
| $OCF_2H$ | 3-$SOCF_3$ |
| $OCF_2H$ | 3-$SO_2CF_3$ |
| $OCF_2H$ | 3-$SCF_2H$ |
| $OCF_2H$ | 3-$SOCF_2H$ |
| $OCF_2H$ | 3-$SO_2CF_2H$ |
| $OCF_2H$ | 4-$CF_3$ |
| $OCF_2H$ | 4-$OCF_3$ |
| $OCF_2H$ | 4-$OCF_2H$ |
| $OCF_2H$ | 4-$OCF_2CF_3H$ |
| $OCF_2H$ | 4-$OCH_2CF_3$ |
| $OCF_2H$ | 4-$SCF_3$ |
| $OCF_2H$ | 4-$SOCF_3$ |
| $OCF_2H$ | 4-$SO_2CF_3$ |
| $OCF_2H$ | 4-$SCF_2H$ |
| $OCF_2H$ | 4-$SOCF_2H$ |
| $OCF_2H$ | 4-$SO_2CF_2H$ |
| Me | 2-Me-4-$CF_3$ |
| Me | 2-Me-4-$OCF_3$ |
| Me | 2-Me-4-$OCF_2H$ |
| Me | 2-Me-4-$OCH_2CF_3$ |
| Me | 2-Me-4-$SCF_3$ |
| Me | 2-Me-4-$SOCF_3$ |
| Me | 2-Me-4-$SO_2CF_3$ |
| Me | 2-Me-4-$SCF_2H$ |
| Me | 2-Me-4-$SOCF_2H$ |
| Me | 2-Me-4-$SO_2CF_2H$ |
| Br | 2-Me-4-$CF_3$ |
| Br | 2-Me-4-$OCF_3$ |
| Br | 2-Me-4-$OCF_2H$ |
| Br | 2-Me-4-$OCH_2CF_3$ |
| Br | 2-Me-4-$SCF_3$ |
| Br | 2-Me-4-$SOCF_3$ |
| Br | 2-Me-4-$SO_2CF_3$ |
| Br | 2-Me-4-$SCF_2H$ |
| Br | 2-Me-4-$SOCF_2H$ |
| Br | 2-Me-4-$SO_2CF_2H$ |
| $CF_3$ | 2-Me-4-$CF_3$ |
| $CF_3$ | 2-Me-4-$OCF_3$ |
| $CF_3$ | 2-Me-4-$OCF_2H$ |
| $CF_3$ | 2-Me-4-$OCH_2CF_3$ |
| $CF_3$ | 2-Me-4-$SCF_3$ |
| $CF_3$ | 2-Me-4-$SOCF_3$ |
| $CF_3$ | 2-Me-4-$SO_2CF_3$ |
| $CF_3$ | 2-Me-4-$SCF_2H$ |
| $CF_3$ | 2-Me-4-$SOCF_2H$ |
| $CF_3$ | 2-Me-4-$SO_2CF_2H$ |
| F | 2-Me-4-$CF_3$ |
| F | 2-Me-4-$OCF_3$ |
| F | 2-Me-4-$OCF_2H$ |
| F | 2-Me-4-$OCH_2CF_3$ |
| F | 2-Me-4-$SCF_3$ |
| F | 2-Me-4-$SOCF_3$ |
| F | 2-Me-4-$SO_2CF_3$ |
| F | 2-Me-4-$SCF_2H$ |
| F | 2-Me-4-$SOCF_2H$ |
| F | 2-Me-4-$SO_2CF_2H$ |
| I | 2-Me-4-$CF_3$ |
| I | 2-Me-4-$OCF_3$ |
| I | 2-Me-4-$OCF_2H$ |
| I | 2-Me-4-$OCH_2CF_3$ |
| I | 2-Me-4-$SCF_3$ |
| I | 2-Me-4-$SOCF_3$ |

TABLE 14-continued

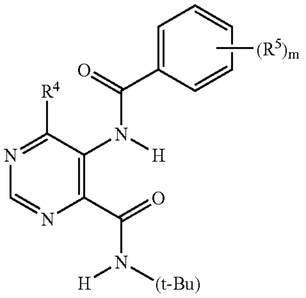

| $R^4$ | $(R^5)_m$ |
|---|---|
| I | 2-Me-4-$SO_2CF_3$ |
| I | 2-Me-4-$SCF_2H$ |
| I | 2-Me-4-$SOCF_2H$ |
| I | 2-Me-4-$SO_2CF_2H$ |
| $NO_2$ | 2-Me-4-$CF_3$ |
| $NO_2$ | 2-Me-4-$OCF_3$ |
| $NO_2$ | 2-Me-4-$OCF_2H$ |
| $NO_2$ | 2-Me-4-$OCH_2CF_3$ |
| $NO_2$ | 2-Me-4-$SCF_3$ |
| $NO_2$ | 2-Me-4-$SOCF_3$ |
| $NO_2$ | 2-Me-4-$SO_2CF_3$ |
| $NO_2$ | 2-Me-4-$SCF_2H$ |
| $NO_2$ | 2-Me-4-$SOCF_2H$ |
| $NO_2$ | 2-Me-4-$SO_2CF_2H$ |
| Cl | 2-Me-4-$CF_3$ |
| Cl | 2-Me-4-$OCF_3$ |
| Cl | 2-Me-4-$OCF_2H$ |
| Cl | 2-Me-4-$OCH_2CF_3$ |
| Cl | 2-Me-4-$SCF_3$ |
| Cl | 2-Me-4-$SOCF_3$ |
| Cl | 2-Me-4-$SO_2CF_3$ |
| Cl | 2-Me-4-$SCF_2H$ |
| Cl | 2-Me-4-$SOCF_2H$ |
| Cl | 2-Me-4-$SO_2CF_2H$ |
| OMe | 2-Me-4-$CF_3$ |
| OMe | 2-Me-4-$OCF_3$ |
| OMe | 2-Me-4-$OCF_2H$ |
| OMe | 2-Me-4-$OCH_2CF_3$ |
| OMe | 2-Me-4-$SCF_3$ |
| OMe | 2-Me-4-$SOCF_3$ |
| OMe | 2-Me-4-$SO_2CF_3$ |
| OMe | 2-Me-4-$SCF_2H$ |
| OMe | 2-Me-4-$SOCF_2H$ |
| OMe | 2-Me-4-$SO_2CF_2H$ |
| SMe | 2-Me-4-$CF_3$ |
| SMe | 2-Me-4-$OCF_3$ |
| SMe | 2-Me-4-$OCF_2H$ |
| SMe | 2-Me-4-$OCH_2CF_3$ |
| SMe | 2-Me-4-$SCF_3$ |
| SMe | 2-Me-4-$SOCF_3$ |
| SMe | 2-Me-4-$SO_2CF_3$ |
| SMe | 2-Me-4-$SCF_2H$ |
| SMe | 2-Me-4-$SOCF_2H$ |
| SMe | 2-Me-4-$SO_2CF_2H$ |

TABLE 15

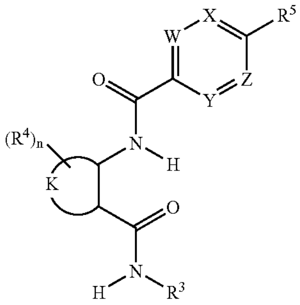

| K | $R^3$ | $(R^4)_n$ | $R^5$ | W | X | Y | Z |
|---|---|---|---|---|---|---|---|
| K-1 | i-Pr | 4-Me | $CF_3$ | CMe | N | CH | CH |
| K-1 | i-Pr | 4-Cl | $CF_3$ | CMe | N | CH | CH |
| K-18 | i-Pr | 4-Me | $CF_3$ | CMe | N | CH | CH |
| K-18 | i-Pr | 4-Cl | $CF_3$ | CMe | N | CH | CH |
| K-14 | i-Pr | 1-Me | $CF_3$ | CMe | N | CH | CH |
| K-28 | i-Pr | 4-Me | $CF_3$ | CMe | N | CH | CH |
| K-28 | i-Pr | 4-Cl | $CF_3$ | CMe | N | CH | CH |
| K-30 | i-Pr | 5-Me | $CF_3$ | CMe | N | CH | CH |
| K-30 | i-Pr | 5-Cl | $CF_3$ | CMe | N | CH | CH |
| K-31 | i-Pr | 2-Me | $CF_3$ | CMe | N | CH | CH |
| K-31 | i-Pr | 2-Cl | $CF_3$ | CMe | N | CH | CH |
| K-33 | i-Pr | 6-Me | $CF_3$ | CMe | N | CH | CH |
| K-33 | i-Pr | 6-Cl | $CF_3$ | CMe | N | CH | CH |
| K-1 | i-Pr | 4-Me | $CF_3$ | CMe | CH | N | CH |
| K-1 | i-Pr | 4-Cl | $CF_3$ | CMe | CH | N | CH |
| K-18 | i-Pr | 4-Me | $CF_3$ | CMe | CH | N | CH |
| K-18 | i-Pr | 4-Cl | $CF_3$ | CMe | CH | N | CH |
| K-14 | i-Pr | 1-Me | $CF_3$ | CMe | CH | N | CH |
| K-28 | i-Pr | 4-Me | $CF_3$ | CMe | CH | N | CH |
| K-28 | i-Pr | 4-Cl | $CF_3$ | CMe | CH | N | CH |
| K-30 | i-Pr | 5-Me | $CF_3$ | CMe | CH | N | CH |
| K-30 | i-Pr | 5-Cl | $CF_3$ | CMe | CH | N | CH |
| K-31 | i-Pr | 2-Me | $CF_3$ | CMe | CH | N | CH |
| K-31 | i-Pr | 2-Cl | $CF_3$ | CMe | CH | N | CH |
| K-33 | i-Pr | 6-Me | $CF_3$ | CMe | CH | N | CH |
| K-33 | i-Pr | 6-Cl | $CF_3$ | CMe | CH | N | CH |
| K-1 | i-Pr | 4-Me | $CF_3$ | CMe | CH | N | CH |
| K-1 | i-Pr | 4-Cl | $CF_3$ | CMe | CH | N | CH |
| K-18 | i-Pr | 4-Me | $CF_3$ | CMe | CH | N | CH |
| K-18 | i-Pr | 4-Cl | $CF_3$ | CMe | CH | N | CH |
| K-14 | i-Pr | 1-Me | $CF_3$ | CMe | CH | N | CH |
| K-28 | i-Pr | 4-Me | $CF_3$ | CMe | CH | CH | N |
| K-28 | i-Pr | 4-Cl | $CF_3$ | CMe | CH | CH | N |
| K-30 | i-Pr | 5-Me | $CF_3$ | CMe | CH | CH | N |
| K-30 | i-Pr | 5-Cl | $CF_3$ | CMe | CH | CH | N |
| K-31 | i-Pr | 2-Me | $CF_3$ | CMe | CH | CH | N |
| K-31 | i-Pr | 2-Cl | $CF_3$ | CMe | CH | CH | N |
| K-33 | i-Pr | 6-Me | $CF_3$ | CMe | CH | CH | N |
| K-33 | i-Pr | 6-Cl | $CF_3$ | CMe | CH | CH | N |
| K-1 | t-Bu | 4-Me | $CF_3$ | CMe | N | CH | CH |
| K-1 | t-Bu | 4-Cl | $CF_3$ | CMe | N | CH | CH |
| K-18 | t-Bu | 4-Me | $CF_3$ | CMe | N | CH | CH |
| K-18 | t-Bu | 4-Cl | $CF_3$ | CMe | N | CH | CH |
| K-14 | t-Bu | 1-Me | $CF_3$ | CMe | N | CH | CH |
| K-28 | t-Bu | 4-Me | $CF_3$ | CMe | N | CH | CH |
| K-28 | t-Bu | 4-Cl | $CF_3$ | CMe | N | CH | CH |
| K-30 | t-Bu | 5-Me | $CF_3$ | CMe | N | CH | CH |
| K-30 | t-Bu | 5-Cl | $CF_3$ | CMe | N | CH | CH |
| K-31 | t-Bu | 2-Me | $CF_3$ | CMe | N | CH | CH |
| K-31 | t-Bu | 2-Cl | $CF_3$ | CMe | N | CH | CH |
| K-33 | t-Bu | 6-Me | $CF_3$ | CMe | N | CH | CH |
| K-33 | t-Bu | 6-Cl | $CF_3$ | CMe | N | CH | CH |
| K-1 | t-Bu | 4-Me | $CF_3$ | CMe | CH | N | CH |
| K-1 | t-Bu | 4-Cl | $CF_3$ | CMe | CH | N | CH |
| K-18 | t-Bu | 4-Me | $CF_3$ | CMe | CH | N | CH |
| K-18 | t-Bu | 4-Cl | $CF_3$ | CMe | CH | N | CH |
| K-14 | t-Bu | 1-Me | $CF_3$ | CMe | CH | N | CH |
| K-28 | t-Bu | 4-Me | $CF_3$ | CMe | CH | N | CH |
| K-28 | t-Bu | 4-Cl | $CF_3$ | CMe | CH | N | CH |
| K-30 | t-Bu | 5-Me | $CF_3$ | CMe | CH | N | CH |
| K-30 | t-Bu | 5-Cl | $CF_3$ | CMe | CH | N | CH |

TABLE 15-continued

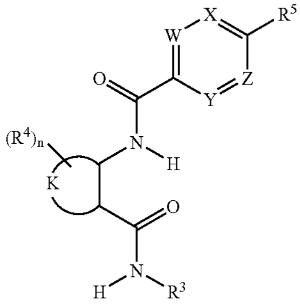

| K | $R^3$ | $(R^4)_n$ | $R^5$ | W | X | Y | Z |
|---|---|---|---|---|---|---|---|
| K-31 | t-Bu | 2-Me | $CF_3$ | CMe | CH | N | CH |
| K-31 | t-Bu | 2-Cl | $CF_3$ | CMe | CH | N | CH |
| K-33 | t-Bu | 6-Me | $CF_3$ | CMe | CH | N | CH |
| K-33 | t-Bu | 6-Cl | $CF_3$ | CMe | CH | N | CH |
| K-1 | t-Bu | 4-Me | $CF_3$ | CMe | CH | N | CH |
| K-1 | t-Bu | 4-Cl | $CF_3$ | CMe | CH | N | CH |
| K-18 | t-Bu | 4-Me | $CF_3$ | CMe | CH | N | CH |
| K-18 | t-Bu | 4-Cl | $CF_3$ | CMe | CH | N | CH |
| K-14 | t-Bu | 1-Me | $CF_3$ | CMe | CH | N | CR |
| K-28 | t-Bu | 4-Me | $CF_3$ | CMe | CH | CH | N |
| K-28 | t-Bu | 4-Cl | $CF_3$ | CMe | CH | CH | N |
| K-30 | t-Bu | 5-Me | $CF_3$ | CMe | CH | CH | N |
| K-30 | t-Bu | 5-Cl | $CF_3$ | CMe | CR | CH | N |
| K-31 | t-Bu | 2-Me | $CF_3$ | CMe | CH | CH | N |
| K-31 | t-Bu | 2-Cl | $CF_3$ | CMe | CH | CR | N |
| K-33 | t-Bu | 6-Me | $CF_3$ | CMe | CR | CH | N |
| K-33 | t-Bu | 6-Cl | $CF_3$ | CMe | CR | CH | N |
| K-1 | i-Pr | 4-Me | $OCF_3$ | CMe | N | CH | CH |
| K-1 | i-Pr | 4-Cl | $OCF_3$ | CMe | N | CH | CH |
| K-18 | i-Pr | 4-Me | $OCF_3$ | CMe | N | CH | CH |
| K-18 | i-Pr | 4-Cl | $OCF_3$ | CMe | N | CH | CH |
| K-14 | i-Pr | 1-Me | $OCF_3$ | CMe | N | CH | CH |
| K-28 | i-Pr | 4-Me | $OCF_3$ | CMe | N | CH | CH |
| K-28 | i-Pr | 4-Cl | $OCF_3$ | CMe | N | CH | CH |
| K-30 | i-Pr | 5-Me | $OCF_3$ | CMe | N | CH | CH |
| K-30 | i-Pr | 5-Cl | $OCF_3$ | CMe | N | CH | CH |
| K-31 | i-Pr | 2-Me | $OCF_3$ | CMe | N | CH | CH |
| K-31 | i-Pr | 2-Cl | $OCF_3$ | CMe | N | CH | CH |
| K-33 | i-Pr | 6-Me | $OCF_3$ | CMe | N | CH | CH |
| K-33 | i-Pr | 6-Cl | $OCF_3$ | CMe | N | CH | CH |
| K-1 | i-Pr | 4-Me | $OCF_3$ | CH | N | CH | CH |
| K-1 | i-Pr | 4-Cl | $OCF_3$ | CH | N | CH | CH |
| K-18 | i-Pr | 4-Me | $OCF_3$ | CH | N | CH | CH |
| K-18 | i-Pr | 4-Cl | $OCF_3$ | CH | N | CH | CH |
| K-14 | i-Pr | 1-Me | $OCF_3$ | CH | N | CH | CH |
| K-28 | i-Pr | 4-Me | $OCF_3$ | CH | N | CH | CH |
| K-28 | i-Pr | 4-Cl | $OCF_3$ | CH | N | CH | CH |
| K-30 | i-Pr | 5-Me | $OCF_3$ | CH | N | CH | CH |
| K-30 | i-Pr | 5-Cl | $OCF_3$ | CH | N | CH | CH |
| K-31 | i-Pr | 2-Me | $OCF_3$ | CH | N | CH | CH |
| K-31 | i-Pr | 2-Cl | $OCF_3$ | CH | N | CH | CH |
| K-33 | i-Pr | 6-Me | $OCF_3$ | CH | N | CH | CH |
| K-33 | i-Pr | 6-Cl | $OCF_3$ | CH | N | CH | CH |
| K-1 | i-Pr | 4-Me | Cl | CMe | CH | CH | N |
| K-1 | i-Pr | 4-Cl | Cl | CMe | CH | CH | N |
| K-18 | i-Pr | 4-Me | Cl | CMe | CH | CH | N |
| K-18 | i-Pr | 4-Cl | Cl | CMe | CH | CH | N |
| K-14 | i-Pr | 1-Me | Cl | CMe | CH | CH | N |
| K-28 | i-Pr | 4-Me | Cl | CMe | CH | CH | N |
| K-28 | i-Pr | 4-Cl | Cl | CMe | CH | CH | N |
| K-30 | i-Pr | S-Me | Cl | CMe | CH | CH | N |
| K-30 | i-Pr | 5-Cl | Cl | CMe | CH | CH | N |
| K-31 | i-Pr | 2-Me | Cl | CMe | CH | CH | N |
| K-31 | i-Pr | 2-Cl | Cl | OMe | CH | CH | N |
| K-33 | i-Pr | 6-Me | Cl | CMe | CH | CH | N |
| K-33 | i-Pr | 6-Cl | Cl | CMe | CH | CH | N |

TABLE 16

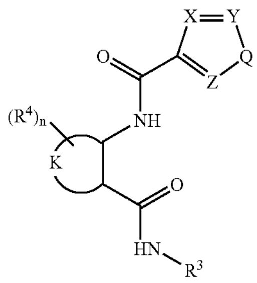

| K | $(R^4)_n$ | Q | X | Y | Z |
|---|---|---|---|---|---|
| | | $R^3$ is i-Pr | | | |
| K-1 | 4-Me | $NCHF_2$ | CMe | N | CH |
| K-1 | 4-Cl | $NCHF_2$ | CMe | N | CH |
| K-18 | 4-Me | $NCHF_2$ | CMe | N | CH |
| K-18 | 4-Cl | $NCHF_2$ | CMe | N | CH |
| K-14 | 1-Me | $NCHF_2$ | CMe | N | CH |
| K-28 | 4-Me | $NCHF_2$ | CMe | N | CH |
| K-28 | 4-Cl | $NCHF_2$ | CMe | N | CH |
| K-30 | S-Me | $NCHF_2$ | CMe | N | CH |
| K-30 | 5-Cl | $NCHF_2$ | CMe | N | CH |
| | | $R^3$ is i-Pr | | | |
| K-31 | 2-Me | $NCHF_2$ | CMe | N | CH |
| K-31 | 2-Cl | $NCHF_2$ | CMe | N | CH |
| K-33 | 6-Me | $NCHF_2$ | CMe | N | CH |
| K-33 | 6-Cl | $NCHF_2$ | CMe | N | CH |
| K-1 | 4-Me | $NCHF_2$ | CH | N | CMe |
| K-1 | 4-Cl | $NCHF_2$ | CH | N | CMe |
| K-18 | 4-Me | $NCHF_2$ | CH | N | CMe |
| K-18 | 4-Cl | $NCHF_2$ | CH | N | CMe |
| K-14 | 1-Me | $NCHF_2$ | CH | N | CMe |
| K-28 | 4-Me | $NCHF_2$ | CH | N | CMe |
| K-28 | 4-Cl | $NCHF_2$ | CH | N | CMe |
| K-30 | 5-Me | $NCHF_2$ | CH | N | CMe |
| K-30 | 5-Cl | $NCHF_2$ | CH | N | CMe |
| K-31 | 2-Me | $NCHF_2$ | CH | N | CMe |
| K-31 | 2-Cl | $NCHF_2$ | CH | N | CMe |
| K-33 | 6-Me | $NCHF_2$ | CH | N | CMe |
| K-33 | 6-Cl | $NCHF_2$ | CH | N | CMe |
| K-1 | 4-Me | $NCF_2CHF_2$ | CMe | N | CH |
| K-1 | 4-Cl | $NCF_2CHF_2$ | CMe | N | CM |
| K-18 | 4-Me | $NCF_2CHF_2$ | CMe | N | CH |
| K-18 | 4-Cl | $NCF_2CHF_2$ | CMe | N | CH |
| K-14 | 1-Me | $NCF_2CHF_2$ | CMe | N | CH |
| K-28 | 4-Me | $NCF_2CHF_2$ | CMe | N | CH |
| K-28 | 4-Cl | $NCF_2CHF_2$ | CMe | N | CM |
| K-30 | 5-Me | $NCF_2CHF_2$ | CMe | N | CH |
| K-30 | 5-Cl | $NCF_2CHF_2$ | CMe | N | CH |
| K-31 | 2-Me | $NCF_2CHF_2$ | CMe | N | CM |
| K-31 | 2-Cl | $NCF_2CHF_2$ | CMe | N | CM |
| K-33 | 6-Me | $NCF_2CHF_2$ | CMe | N | CH |
| K-33 | 6-Cl | $NCF_2CHF_2$ | CMe | N | CH |
| K-1 | 4-Me | $NCH_2CF_3$ | CMe | N | CH |
| K-1 | 4-Cl | $NCH_2CF_3$ | CMe | N | CH |
| K-18 | 4-Me | $NCH_2CF_3$ | CMe | N | CH |
| K-18 | 4-Cl | $NCH_2CF_3$ | CMe | N | CH |
| K-14 | 1-Me | $NCH_2CF_3$ | CMe | N | CH |
| K-28 | 4-Me | $NCH_2CF_3$ | CMe | N | CH |
| | | $R^3$ is i-Pr | | | |
| K-28 | 4-Cl | $NCH_2CF_3$ | CMe | N | CH |
| K-30 | 5-Me | $NCH_2CF_3$ | CMe | N | CH |
| K-30 | S-Cl | $NCH_2CF_3$ | CMe | N | CH |
| K-31 | 2-Me | $NCH_2CF_3$ | CMe | N | CH |
| K-31 | 2-Cl | $NCH_2CF_3$ | CMe | N | CH |
| K-33 | 6-Me | $NCH_2CF_3$ | CMe | N | CH |
| K-33 | 6-Cl | $NCH_2CF_3$ | CMe | N | CH |
| K-1 | 4-Me | $NCF2CF_3$ | CH | N | CMe |
| K-1 | 4-Cl | $NCH_2CF_3$ | CH | N | CMe |
| K-18 | 4-Me | $NCH_2CF_3$ | CH | N | CMe |
| K-18 | 4-Cl | $NCH_2CF_3$ | CH | N | CMe |
| K-14 | 1-Me | $NCH_2CF_3$ | CH | N | CMe |

TABLE 16-continued

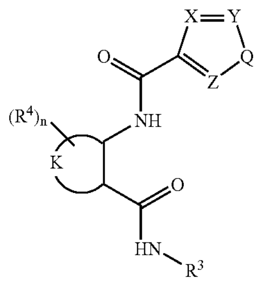

| K | $(R^4)_n$ | Q | X | Y | Z |
|---|---|---|---|---|---|
| K-28 | 4-Me | $NCH_2CF_3$ | CH | N | CMe |
| K-28 | 4-Cl | $NCH_2CF_3$ | CH | N | CMe |
| K-30 | S-Me | $NCH_2CF_3$ | CH | N | CMe |
| K-30 | 5-Cl | $NCH_2CF_3$ | CH | N | CMe |
| K-31 | 2-Me | $NCH_2CF_3$ | CH | N | CMe |
| K-31 | 2-Cl | $NCH_2CF_3$ | CH | N | CMe |
| K-33 | 6-Me | $NCH_2CF_3$ | CH | N | CMe |
| K-33 | 6-Cl | $NCH_2CF_3$ | CH | N | CMe |
| K-1 | 4-Me | $NCF_2CHF_2$ | N | CH | CMe |
| K-1 | 4-Cl | $NCF_2CHF_2$ | N | CH | CMe |
| K-18 | 4-Me | $NCF_2CHF_2$ | N | CH | CMe |
| K-18 | 4-Cl | $NCF_2CHF_2$ | N | CH | CMe |
| K-14 | 1-Me | $NCF_2CHF_2$ | N | CH | CMe |
| K-28 | 4-Me | $NCF_2CHF_2$ | N | CH | CMe |
| K-28 | 4-Cl | $NCF_2CHF_2$ | N | CH | CMe |
| K-30 | 5-Me | $NCF_2CHF_2$ | N | CH | CMe |
| K-30 | 5-Cl | $NCF_2CHF_2$ | N | CH | CMe |
| K-31 | 2-Me | $NCF_2CHF_2$ | N | CH | CMe |
| K-31 | 2-Cl | $NCF_2CHF_2$ | N | CH | CMe |
| K-33 | 6-Me | $NCF_2CHF_2$ | N | CH | CMe |
| K-33 | 6-Cl | $NCF_2CHF_2$ | N | CH | CMe |
| | | $R^3$ is t-Bu | | | |
| K-1 | 4-Me | $NCHF_2$ | CMe | N | CH |
| K-1 | 4-Cl | $NCHF_2$ | CMe | N | CH |
| K-18 | 4-Me | $NCHF_2$ | CMe | N | CH |
| K-18 | 4-Cl | $NCHF_2$ | CMe | N | CH |
| K-14 | 1-Me | $NCHF_2$ | CMe | N | CH |
| K-28 | 4-Me | $NCHF_2$ | CMe | N | CH |
| K-28 | 4-Cl | $NCHF_2$ | CMe | N | CH |
| K-30 | 5-Me | $NCHF_2$ | CMe | N | CH |
| K-30 | 5-Cl | $NCHF_2$ | CMe | N | CH |
| K-31 | 2-Me | $NCHF_2$ | CMe | N | CH |
| K-31 | 2-Cl | $NCHF_2$ | CMe | N | CH |
| K-33 | 6-Me | $NCHF_2$ | CMe | N | CH |
| K-33 | 6-Cl | $NCHF_2$ | CMe | N | CH |
| K-1 | 4-Me | $NCHF_2$ | CH | N | CMe |
| K-1 | 4-Cl | $NCHF_2$ | CH | N | CMe |
| K-18 | 4-Me | $NCHF_2$ | CH | N | CMe |
| K-18 | 4-Cl | $NCHF_2$ | CH | N | CMe |
| K-14 | 1-Me | $NCHF_2$ | CH | N | CMe |
| K-28 | 4-Me | $NCHF_2$ | CH | N | CMe |
| K-28 | 4-Cl | $NCHF_2$ | CH | N | CMe |
| K-30 | 5-Me | $NCHF_2$ | CH | N | CMe |
| K-30 | 5-Cl | $NCHF_2$ | CH | N | CMe |
| K-31 | 2-Me | $NCHF_2$ | CH | N | CMe |
| K-31 | 2-Cl | $NCHF_2$ | CH | N | CMe |
| K-33 | 6-Me | $NCHF_2$ | CH | N | CMe |
| K-33 | 6-Cl | $NCHF_2$ | CH | N | CMe |
| K-1 | 4-Me | $NCF_2CHF_2$ | CMe | N | CH |
| K-1 | 4-Cl | $NCF_2CHF_2$ | CMe | N | CH |
| K-18 | 4-Me | $NCF_2CHF_2$ | CMe | N | CH |
| K-18 | 4-Cl | $NCF_2CHF_2$ | CMe | N | CH |
| K-14 | 1-Me | $NCF_2CHF_2$ | CMe | N | CH |
| K-25 | 4-Me | $NCF_2CHF_2$ | CMe | N | CH |
| K-25 | 4-Cl | $NCF_2CHF_2$ | CMe | N | CH |
| K-30 | 5-Me | $NCF_2CHF_2$ | CMe | N | CH |
| K-30 | 5-Cl | $NCF_2CHF_2$ | CMe | N | CH |
| K-31 | 2-Me | $NCF_2CHF_2$ | CMe | N | CH |
| | | $R^3$ is t-Bu | | | |
| K-31 | 2-Cl | $NCF_2CHF_2$ | CMe | N | CH |
| K-33 | 6-Me | $NCF_2CHF_2$ | CMe | N | CH |

TABLE 16-continued

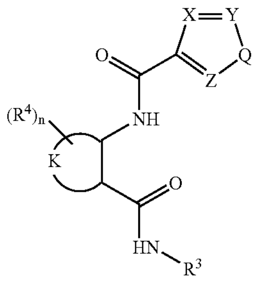

| K | $(R^4)_n$ | Q | X | Y | Z |
|---|---|---|---|---|---|
| K-33 | 6-Cl | $NCF_2CHF_2$ | CMe | N | CH |
| K-1 | 4-Me | $NCH_2CF_3$ | CMe | N | CH |
| K-1 | 4-Cl | $NCH_2CF_3$ | CMe | N | CH |
| K-18 | 4-Me | $NCH_2CF_3$ | CMe | N | CH |
| K-18 | 4-Cl | $NCH_2CF_3$ | CMe | N | CH |
| K-14 | 1-Me | $NCH_2CF_3$ | CMe | N | CH |
| K-28 | 4-Me | $NCH_2CF_3$ | CMe | N | CH |
| K-28 | 4-Cl | $NCH_2CF_3$ | CMe | N | CH |
| K-30 | 5-Me | $NCH_2CF_3$ | CMe | N | CH |
| K-30 | 5-Cl | $NCH_2CF_3$ | CMe | N | CH |
| K-31 | 2-Me | $NCH_2CF_3$ | CMe | N | CH |
| K-31 | 2-Cl | $NCH_2CF_3$ | CMe | N | CH |
| K-33 | 6-Me | $NCH_2CF_3$ | CMe | N | CH |
| K-33 | 6-Cl | $NCH_2CF_3$ | CMe | N | CH |
| K-1 | 4-Me | $NCH_2CF_3$ | CH | N | CMe |
| K-1 | 4-Cl | $NCH_2CF_3$ | CH | N | CMe |
| K-18 | 4-Me | $NCH_2CF_3$ | CH | N | CMe |
| K-18 | 4-Cl | $NCH_2CF_3$ | CH | N | CMe |
| K-14 | 1-Me | $NCH_2CF_3$ | CH | N | CMe |
| K-28 | 4-Me | $NCH_2CF_3$ | CH | N | CMe |
| K-28 | 4-Cl | $NCH_2CF_3$ | CH | N | CMe |
| K-30 | 5-Me | $NCH_2CF_3$ | CH | N | CMe |
| K-30 | 5-Cl | $NCH_2CF_3$ | CH | N | CMe |
| K-31 | 2-Me | $NCH_2CF_3$ | CH | N | CMe |
| K-31 | 2-Cl | $NCH_2CF_3$ | CH | N | CMe |
| K-33 | 6-Me | $NCH_2CF_3$ | CH | N | CMe |
| K-33 | 6-Cl | $NCH_2CF_3$ | CH | N | CMe |
| K-1 | 4-Me | $NCF_2CHF_2$ | N | CH | CMe |
| K-1 | 4-Cl | $NCF_2CHF_2$ | N | CH | CMe |
| K-18 | 4-Me | $NCF_2CHF_2$ | N | CH | CMe |
| K-18 | 4-Cl | $NCF_2CHF_2$ | N | CH | CMe |
| K-14 | 1-Me | $NCF_2CHF_2$ | N | CH | CMe |
| K-28 | 4-Me | $NCF_2CHF_2$ | N | CH | CMe |
| K-28 | 4-Cl | $NCF_2CHF_2$ | N | CH | CMe |
| | | $R^3$ is t-Bu | | | |
| K-30 | 5-Me | $NCF_2CHF_2$ | N | CH | CMe |
| K-30 | 5-Cl | $NCF_2CHF_2$ | N | CH | CMe |
| K-31 | 2-Me | $NCF_2CHF_2$ | N | CH | CMe |
| K-31 | 2-Cl | $NCF_2CHF_2$ | N | CH | CMe |
| K-33 | 6-Me | $NCF_2CHF_2$ | N | CH | CMe |
| K-33 | 6-Cl | $NCF_2CHF_2$ | N | CH | CMe |

TABLE 17

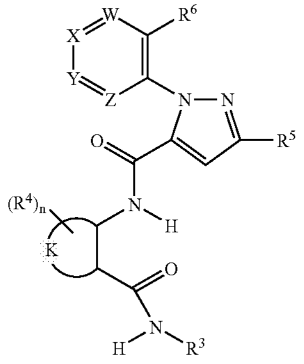

| K | W | X | Y | Z | $R^3$ | $(R^4)_n$ | $R^5$ | $R^6$ |
|---|---|---|---|---|---|---|---|---|
| K-1 | CH | CH | CH | CH | i-Pr | 4-Me | $CF_3$ | Me |
| K-1 | CH | CH | CH | CH | t-Bu | 4-Me | $CF_3$ | Me |
| K-1 | CH | CH | CH | CH | i-Pr | 4-Cl | $CF_3$ | Me |
| K-1 | CH | CH | CH | CH | t-Bu | 4-Cl | $CF_3$ | Me |
| K-1 | CH | CH | CH | CH | i-Pr | 4-Me | $CF_3$ | F |
| K-1 | CH | CH | CH | CH | t-Bu | 4-Me | $CF_3$ | F |
| K-1 | CH | CH | CH | CH | i-Pr | 4-Cl | $CF_3$ | F |
| K-1 | CH | CH | CH | CH | t-Bu | 4-Cl | $CF_3$ | F |
| K-1 | CH | CH | CH | CH | i-Pr | 4-Me | $CF_3$ | Cl |
| K-1 | CH | CH | CH | CH | t-Bu | 4-Me | $CF_3$ | Cl |
| K-1 | CH | CH | CH | CH | i-Pr | 4-Cl | $CF_3$ | Cl |
| K-1 | CH | CH | CH | CH | t-Bu | 4-Cl | $CF_3$ | Cl |
| K-1 | CH | CH | CH | CH | i-Pr | 4-Me | $CF_3$ | Br |
| K-1 | CH | CH | CH | CH | t-Bu | 4-Me | $CF_3$ | Br |
| K-1 | CH | CH | CH | CH | i-Pr | 4-Cl | $CF_3$ | Br |
| K-1 | CH | CH | CH | CH | t-Bu | 4-Cl | $CF_3$ | Br |
| K-1 | CH | CH | CH | CH | i-Pr | 4-Me | $CF_3$ | CN |
| K-1 | CH | CH | CH | CH | t-Bu | 4-Me | $CF_3$ | CN |
| K-1 | CH | CH | CH | CH | i-Pr | 4-Cl | $CF_3$ | CN |
| K-1 | CH | CH | CH | CH | t-Bu | 4-Cl | $CF_3$ | CN |
| K-1 | CH | CH | CH | CH | i-Pr | 4-Me | $CF_3$ | Me |
| K-1 | CH | CH | CH | CH | t-Bu | 4-Me | $CF_3$ | Me |
| K-1 | CH | CH | CH | CH | i-Pr | 4-Cl | $CF_3$ | Me |
| K-1 | CH | CH | CH | CH | t-Bu | 4-Cl | $CF_3$ | Me |
| K-1 | CH | CH | CH | CH | i-Pr | 4-Me | $CF_3$ | F |
| K-1 | CH | CH | CH | CH | t-Bu | 4-Me | $CF_3$ | F |
| K-1 | CH | CH | CH | CH | i-Pr | 4-Cl | $CF_3$ | F |
| K-1 | CH | CH | CH | CH | t-Bu | 4-Cl | $CF_3$ | F |
| K-1 | CH | CH | CH | CH | i-Pr | 4-Me | $CF_3$ | Cl |
| K-1 | CH | CH | CH | CH | t-Bu | 4-Me | $CF_3$ | Cl |
| K-1 | CH | CH | CH | CH | i-Pr | 4-Cl | $CF_3$ | Cl |
| K-1 | CH | CH | CH | CH | t-Bu | 4-Cl | $CF_3$ | Cl |
| K-1 | CH | CH | CH | CH | i-Pr | 4-Me | $CF_3$ | Br |
| K-1 | CH | CH | CH | CH | t-Bu | 4-Me | $CF_3$ | Br |
| K-1 | CH | CH | CH | CH | i-Pr | 4-Cl | $CF_3$ | Br |
| K-1 | CH | CH | CH | N | t-Bu | 4-Cl | $CF_3$ | Br |
| K-1 | CH | CH | CH | N | i-Pr | 4-Me | $CF_3$ | CN |
| K-1 | CH | CH | CH | N | t-Bu | 4-Me | $CF_3$ | CN |
| K-1 | CH | CH | CH | N | i-Pr | 4-Cl | $CF_3$ | CN |
| K-1 | CH | CH | CH | N | i-Pr | 4-Cl | $CF_3$ | CN |
| K-18 | CH | CH | CH | CH | i-Pr | 4-Me | $CF_3$ | Me |
| K-18 | CH | CH | CH | CH | t-Bu | 4-Me | $CF_3$ | Me |
| K-18 | CH | CH | CH | CH | i-Pr | 4-Cl | $CF_3$ | Me |
| K-18 | CH | CH | CH | CH | t-Bu | 4-Cl | $CF_3$ | Me |
| K-18 | CH | CH | CH | CH | i-Pr | 4-Me | $CF_3$ | F |
| K-18 | CH | CH | CH | CH | t-Bu | 4-Me | $CF_3$ | F |
| K-18 | CH | CH | CH | CH | i-Pr | 4-Cl | $CF_3$ | F |
| K-18 | CH | CH | CH | CH | t-Bu | 4-Cl | $CF_3$ | F |
| K-18 | CH | CH | CH | CH | i-Pr | 4-Me | $CF_3$ | Cl |
| K-18 | CH | CH | CH | CH | t-Bu | 4-Me | $CF_3$ | Cl |
| K-18 | CH | CH | CH | CH | i-Pr | 4-Cl | $CF_3$ | Cl |
| K-18 | CH | CH | CH | CH | t-Bu | 4-Cl | $CF_3$ | Cl |
| K-18 | CH | CH | CH | CH | i-Pr | 4-Me | $CF_3$ | Br |
| K-18 | CH | CH | CH | CH | t-Bu | 4-Me | $CF_3$ | Br |
| K-18 | CH | CH | CH | CH | i-Pr | 4-Cl | $CF_3$ | Br |
| K-18 | CH | CH | CH | CH | t-Bu | 4-Cl | $CF_3$ | Br |
| K-18 | CH | CH | CH | CH | i-Pr | 4-Me | $CF_3$ | CN |
| K-18 | CH | CH | CH | CH | t-Bu | 4-Me | $CF_3$ | CN |
| K-18 | CH | CH | CH | CH | i-Pr | 4-Cl | $CF_3$ | CN |

TABLE 17-continued

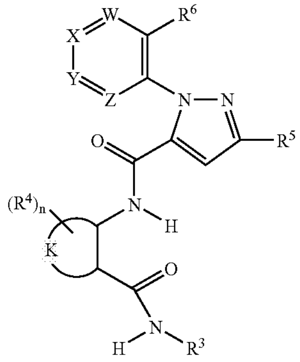

| K | W | X | Y | Z | $R^3$ | $(R^4)_n$ | $R^5$ | $R^6$ |
|---|---|---|---|---|---|---|---|---|
| K-18 | CH | CH | CH | CH | t-Bu | 4-Cl | $CF_3$ | CN |
| K-18 | CH | CH | CH | CH | i-Pr | 4-Me | $CF_3$ | Me |
| K-18 | CH | CH | CH | CH | t-Bu | 4-Me | $CF_3$ | Me |
| K-18 | CH | CH | CH | CH | i-Pr | 4-Cl | $CF_3$ | Me |
| K-18 | CH | CH | CH | CH | t-Bu | 4-Cl | $CF_3$ | Me |
| K-18 | CH | CH | CH | CH | i-Pr | 4-Me | $CF_3$ | F |
| K-18 | CH | CH | CH | CH | t-Bu | 4-Me | $CF_3$ | F |
| K-18 | CH | CH | CH | CH | i-Pr | 4-Cl | $CF_3$ | F |
| K-18 | CH | CH | CH | CH | t-Bu | 4-Cl | $CF_3$ | F |
| K-18 | CH | CH | CH | CH | i-Pr | 4-Me | $CF_3$ | Cl |
| K-18 | CH | CH | CH | CH | t-Bu | 4-Me | $CF_3$ | Cl |
| K-18 | CH | CH | CH | CH | i-Pr | 4-Cl | $CF_3$ | Cl |
| K-18 | CH | CH | CH | CH | t-Bu | 4-Cl | $CF_3$ | Cl |
| K-18 | CH | CH | CH | CH | i-Pr | 4-Me | $CF_3$ | Br |
| K-18 | CH | CH | CH | CH | t-Bu | 4-Me | $CF_3$ | Br |
| K-18 | CH | CH | CH | CH | i-Pr | 4-Cl | $CF_3$ | Br |
| K-18 | CH | CH | CH | N | t-Bu | 4-Cl | $CF_3$ | Br |
| K-18 | CH | CH | CH | N | i-Pr | 4-Me | $CF_3$ | CN |
| K-18 | CH | CH | CH | N | t-Bu | 4-Me | $CF_3$ | CN |
| K-18 | CH | CH | CH | N | i-Pr | 4-Cl | $CF_3$ | CN |
| K-18 | CH | CH | CH | N | i-Pr | 4-Cl | $CF_3$ | CN |
| K-14 | CH | CH | CH | CH | i-Pr | 1-Me | $CF_3$ | Me |
| K-14 | CH | CH | CH | CH | t-Bu | 1-Me | $CF_3$ | Me |
| K-14 | CH | CH | CH | CH | i-Pr | 1-Me | $CF_3$ | F |
| K-14 | CH | CH | CH | CH | t-Bu | 1-Me | $CF_3$ | F |
| K-14 | CH | CH | CH | CH | i-Pr | 1-Me | $CF_3$ | Cl |
| K-14 | CH | CH | CH | CH | t-Bu | 1-Me | $CF_3$ | Cl |
| K-14 | CH | CH | CH | CH | i-Pr | 1-Me | $CF_3$ | Br |
| K-14 | CH | CH | CH | CH | t-Bu | 1-Me | $CF_3$ | Br |
| K-14 | CH | CH | CH | CH | i-Pr | 1-Me | $CF_3$ | CN |
| K-14 | CH | CH | CH | CH | t-Bu | 1-Me | $CF_3$ | CN |
| K-14 | CH | CH | CH | CH | i-Pr | 1-Me | $CF_3$ | Me |
| K-14 | CH | CH | CH | CH | t-Bu | 1-Me | $CF_3$ | Me |
| K-14 | CH | CH | CH | CH | i-Pr | 1-Me | $CF_3$ | F |
| K-14 | CH | CH | CH | CH | t-Bu | 1-Me | $CF_3$ | F |
| K-14 | CH | CH | CH | CH | i-Pr | 1-Me | $CF_3$ | Cl |
| K-14 | CH | CH | CH | CH | t-Bu | 1-Me | $CF_3$ | Cl |
| K-14 | CH | CH | CH | CH | i-Pr | 1-Me | $CF_3$ | Br |
| K-14 | CH | CH | CH | CH | t-Bu | 1-Me | $CF_3$ | Br |
| K-14 | CH | CH | CH | CH | i-Pr | 1-Me | $CF_3$ | CN |
| K-14 | CH | CH | CH | CH | t-Bu | 1-Me | $CF_3$ | CN |
| K-28 | CH | CH | CH | CH | i-Pr | 4-Me | $CF_3$ | Me |
| K-28 | CH | CH | CH | CH | t-Bu | 4-Me | $CF_3$ | Me |
| K-28 | CH | CH | CH | CH | i-Pr | 4-Cl | $CF_3$ | Me |
| K-28 | CH | CH | CH | CH | t-Bu | 4-Cl | $CF_3$ | Me |
| K-28 | CH | CH | CH | CH | i-Pr | 4-Me | $CF_3$ | F |
| K-28 | CH | CH | CH | CH | t-Bu | 4-Me | $CF_3$ | F |
| K-28 | CH | CH | CH | CH | i-Pr | 4-Cl | $CF_3$ | F |
| K-28 | CH | CH | CH | CH | t-Bu | 4-Cl | $CF_3$ | F |
| K-28 | CH | CH | CH | CH | i-Pr | 4-Me | $CF_3$ | Cl |
| K-28 | CH | CH | CH | CH | t-Bu | 4-Me | $CF_3$ | Cl |
| K-28 | CH | CH | CH | CH | i-Pr | 4-Cl | $CF_3$ | Cl |
| K-28 | CH | CH | CH | CH | t-Bu | 4-Cl | $CF_3$ | Cl |
| K-28 | CH | CH | CH | CH | i-Pr | 4-Me | $CF_3$ | Br |
| K-28 | CH | CH | CH | CH | t-Bu | 4-Me | $CF_3$ | Br |
| K-28 | CH | CH | CH | CH | i-Pr | 4-Cl | $CF_3$ | Br |
| K-28 | CH | CH | CH | CH | t-Bu | 4-Cl | $CF_3$ | Br |
| K-28 | CH | CH | CH | CH | i-Pr | 4-Me | $CF_3$ | CN |
| K-28 | CH | CH | CH | CH | t-Bu | 4-Me | $CF_3$ | CN |

TABLE 17-continued

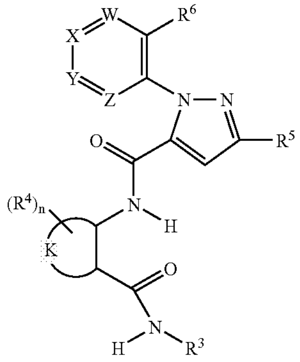

| K | W | X | Y | Z | $R^3$ | $(R^4)_n$ | $R^5$ | $R^6$ |
|---|---|---|---|---|---|---|---|---|
| K-28 | CH | CH | CH | CH | i-Pr | 4-Cl | $CF_3$ | CN |
| K-28 | CH | CH | CH | CH | t-Bu | 4-Cl | $CF_3$ | CN |
| K-28 | CH | CH | CH | N | i-Pr | 4-Me | $CF_3$ | Me |
| K-28 | CH | CH | CH | N | t-Bu | 4-Me | $CF_3$ | Me |
| K-28 | CH | CH | CH | N | i-Pr | 4-Cl | $CF_3$ | Me |
| K-28 | CH | CH | CH | N | t-Bu | 4-Cl | $CF_3$ | Me |
| K-28 | CH | CH | CH | N | i-Pr | 4-Me | $CF_3$ | F |
| K-28 | CH | CH | CH | N | t-Bu | 4-Me | $CF_3$ | F |
| K-28 | CH | CH | CH | N | i-Pr | 4-Cl | $CF_3$ | F |
| K-28 | CH | CH | CH | N | t-Bu | 4-Cl | $CF_3$ | F |
| K-28 | CH | CH | CH | N | i-Pr | 4-Me | $CF_3$ | Cl |
| K-28 | CH | CH | CH | N | t-Bu | 4-Me | $CF_3$ | Cl |
| K-28 | CH | CH | CH | N | i-Pr | 4-Cl | $CF_3$ | Cl |
| K-28 | CH | CH | CH | N | t-Bu | 4-Cl | $CF_3$ | Cl |
| K-28 | CH | CH | CH | N | i-Pr | 4-Me | $CF_3$ | Br |
| K-28 | CH | CH | CH | N | t-Bu | 4-Me | $CF_3$ | Br |
| K-28 | CH | CH | CH | N | i-Pr | 4-Cl | $CF_3$ | Br |
| K-28 | CH | CH | CH | N | t-Bu | 4-Cl | $CF_3$ | Br |
| K-28 | CH | CH | CH | N | i-Pr | 4-Me | $CF_3$ | CN |
| K-28 | CH | CH | CH | N | t-Bu | 4-Me | $CF_3$ | CN |
| K-28 | CH | CH | CH | N | i-Pr | 4-Cl | $CF_3$ | CN |
| K-28 | CH | CH | CH | N | i-Pr | 4-Cl | $CF_3$ | CN |
| K-30 | CH | CH | CH | CH | i-Pr | Me | $CF_3$ | Me |
| K-30 | CH | CH | CH | CH | t-Bu | Me | $CF_3$ | Me |
| K-30 | CH | CH | CH | CH | i-Pr | 5-Cl | $CF_3$ | Me |
| K-30 | CH | CH | CH | CH | t-Bu | 5-Cl | $CF_3$ | Me |
| K-30 | CH | CH | CH | CH | i-Pr | Me | $CF_3$ | F |
| K-30 | CH | CH | CH | CH | t-Bu | Me | $CF_3$ | F |
| K-30 | CH | CH | CH | CH | i-Pr | 5-Cl | $CF_3$ | F |
| K-30 | CH | CH | CH | CH | t-Bu | 5-Cl | $CF_3$ | F |
| K-30 | CH | CH | CH | CH | i-Pr | Me | $CF_3$ | Cl |
| K-30 | CH | CH | CH | CH | t-Bu | Me | $CF_3$ | Cl |
| K-30 | CH | CH | CH | CH | i-Pr | 5-Cl | $CF_3$ | Cl |
| K-30 | CH | CH | CH | CH | t-Bu | 5-Cl | $CF_3$ | Cl |
| K-30 | CH | CH | CH | CH | i-Pr | Me | $CF_3$ | Br |
| K-30 | CH | CH | CH | CH | t-Bu | Me | $CF_3$ | Br |
| K-30 | CH | CH | CH | CH | i-Pr | 5-Cl | $CF_3$ | Br |
| K-30 | CH | CH | CH | CH | t-Bu | 5-Cl | $CF_3$ | Br |
| K-30 | CH | CH | CH | CH | i-Pr | Me | $CF_3$ | CN |
| K-30 | CH | CH | CH | CH | t-Bu | Me | $CF_3$ | CN |
| K-30 | CH | CH | CH | CH | i-Pr | 5-Cl | $CF_3$ | CN |
| K-30 | CH | CH | CH | CH | t-Bu | 5-Cl | $CF_3$ | CN |
| K-30 | CH | CH | CH | N | i-Pr | Me | $CF_3$ | Me |
| K-30 | CH | CH | CH | N | t-Bu | Me | $CF_3$ | Me |
| K-30 | CH | CH | CH | N | i-Pr | 5-Cl | $CF_3$ | Me |
| K-30 | CH | CH | CH | N | t-Bu | 5-Cl | $CF_3$ | Me |
| K-30 | CH | CH | CH | N | i-Pr | Me | $CF_3$ | F |
| K-30 | CH | CH | CH | N | t-Bu | Me | $CF_3$ | F |
| K-30 | CH | CH | CH | N | i-Pr | 5-Cl | $CF_3$ | F |
| K-30 | CH | CH | CH | N | t-Bu | 5-Cl | $CF_3$ | F |
| K-30 | CH | CH | CH | N | i-Pr | Me | $CF_3$ | Cl |
| K-30 | CH | CH | CH | N | t-Bu | Me | $CF_3$ | Cl |
| K-30 | CH | CH | CH | N | i-Pr | 5-Cl | $CF_3$ | Cl |
| K-30 | CH | CH | CH | N | t-Bu | 5-Cl | $CF_3$ | Cl |
| K-30 | CH | CH | CH | N | i-Pr | Me | $CF_3$ | Br |
| K-30 | CH | CH | CH | N | t-Bu | Me | $CF_3$ | Br |
| K-30 | CH | CH | CH | N | i-Pr | 5-Cl | $CF_3$ | Br |
| K-30 | CH | CH | CH | N | t-Bu | 5-Cl | $CF_3$ | Br |
| K-30 | CH | CH | CH | N | i-Pr | Me | $CF_3$ | CN |

TABLE 17-continued

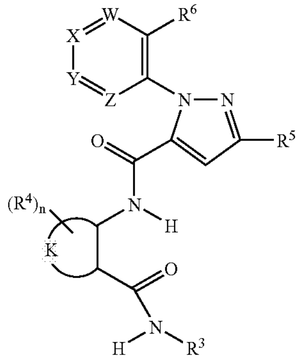

| K | W | X | Y | Z | $R^3$ | $(R^4)_n$ | $R^5$ | $R^6$ |
|---|---|---|---|---|---|---|---|---|
| K-30 | CH | CH | CH | N | t-Bu | Me | $CF_3$ | CN |
| K-30 | CH | CH | CH | N | i-Pr | 5-Cl | $CF_3$ | CN |
| K-30 | CH | CH | CH | N | i-Pr | 5-Cl | $CF_3$ | CN |
| K-30 | CH | CH | CH | CH | i-Pr | Me | $CF_3$ | Me |
| K-30 | CH | CH | CH | CH | t-Bu | Me | $CF_3$ | Me |
| K-30 | CH | CH | CH | CH | i-Pr | 5-Cl | $CF_3$ | Me |
| K-30 | CH | CH | CH | CH | t-Bu | 5-Cl | $CF_3$ | Me |
| K-30 | CH | CH | CH | CH | i-Pr | Me | $CF_3$ | F |
| K-30 | CH | CH | CH | CH | t-Bu | Me | $CF_3$ | F |
| K-30 | CH | CH | CH | CH | i-Pr | 5-Cl | $CF_3$ | F |
| K-30 | CH | CH | CH | CH | t-Bu | 5-Cl | $CF_3$ | F |
| K-30 | CH | CH | CH | CH | i-Pr | Me | $CF_3$ | Cl |
| K-30 | CH | CH | CH | CH | t-Bu | Me | $CF_3$ | Cl |
| K-30 | CH | CH | CH | CH | i-Pr | 5-Cl | $CF_3$ | Cl |
| K-30 | CH | CH | CH | CH | t-Bu | 5-Cl | $CF_3$ | Cl |
| K-30 | CH | CH | CH | CH | i-Pr | Me | $CF_3$ | Br |
| K-30 | CH | CH | CH | CH | t-Bu | Me | $CF_3$ | Br |
| K-30 | CH | CH | CH | CH | i-Pr | 5-Cl | $CF_3$ | Br |
| K-30 | CH | CH | CH | CH | t-Bu | 5-Cl | $CF_3$ | Br |
| K-30 | CH | CH | CH | CH | i-Pr | Me | $CF_3$ | CN |
| K-30 | CH | CH | CH | CH | t-Bu | Me | $CF_3$ | CN |
| K-30 | CH | CH | CH | CH | i-Pr | 5-Cl | $CF_3$ | CN |
| K-30 | CH | CH | CH | CH | t-Bu | 5-Cl | $CF_3$ | CN |
| K-30 | CH | CH | CH | N | i-Pr | Me | $CF_3$ | Me |
| K-30 | CH | CH | CH | N | t-Bu | Me | $CF_3$ | Me |
| K-30 | CH | CH | CH | N | i-Pr | 5-Cl | $CF_3$ | Me |
| K-30 | CH | CH | CH | N | t-Bu | 5-Cl | $CF_3$ | Me |
| K-30 | CH | CH | CH | N | i-Pr | Me | $CF_3$ | F |
| K-30 | CH | CH | CH | N | t-Bu | Me | $CF_3$ | F |
| K-30 | CH | CH | CH | N | i-Pr | 5-Cl | $CF_3$ | F |
| K-30 | CH | CH | CH | N | t-Bu | 5-Cl | $CF_3$ | F |
| K-30 | CH | CH | CH | N | i-Pr | Me | $CF_3$ | Cl |
| K-30 | CH | CH | CH | N | t-Bu | Me | $CF_3$ | Cl |
| K-30 | CH | CH | CH | N | i-Pr | 5-Cl | $CF_3$ | Cl |
| K-30 | CH | CH | CH | N | t-Bu | 5-Cl | $CF_3$ | Cl |
| K-30 | CH | CH | CH | N | i-Pr | Me | $CF_3$ | Br |
| K-30 | CH | CH | CH | N | t-Bu | Me | $CF_3$ | Br |
| K-30 | CH | CH | CH | N | i-Pr | 5-Cl | $CF_3$ | Br |
| K-30 | CH | CH | CH | N | t-Bu | 5-Cl | $CF_3$ | Br |
| K-30 | CH | CH | CH | N | i-Pr | Me | $CF_3$ | CN |
| K-30 | CH | CH | CH | N | t-Bu | Me | $CF_3$ | CN |
| K-30 | CH | CH | CH | N | i-Pr | 5-Cl | $CF_3$ | CN |
| K-30 | CH | CH | CH | N | i-Pr | 5-Cl | $CF_3$ | CN |
| K-31 | CH | CH | CH | CH | i-Pr | 2-Me | $CF_3$ | Me |
| K-31 | CH | CH | CH | CH | t-Bu | 2-Me | $CF_3$ | Me |
| K-31 | CH | CH | CH | CH | i-Pr | 2-Cl | $CF_3$ | Me |
| K-31 | CH | CH | CH | CH | t-Bu | 2-Cl | $CF_3$ | Me |
| K-31 | CH | CH | CH | CH | i-Pr | 2-Me | $CF_3$ | F |
| K-31 | CH | CH | CH | CH | t-Bu | 2-Me | $CF_3$ | F |
| K-31 | CH | CH | CH | CH | i-Pr | 2-Cl | $CF_3$ | F |
| K-31 | CH | CH | CH | CH | t-Bu | 2-Cl | $CF_3$ | F |
| K-31 | CH | CH | CH | CH | i-Pr | 2-Me | $CF_3$ | Cl |
| K-31 | CH | CH | CH | CH | t-Bu | 2-Me | $CF_3$ | Cl |
| K-31 | CH | CH | CH | CH | i-Pr | 2-Cl | $CF_3$ | Cl |
| K-31 | CH | CH | CH | CH | t-Bu | 2-Cl | $CF_3$ | Cl |
| K-31 | CH | CH | CH | CH | i-Pr | 2-Me | $CF_3$ | Br |
| K-31 | CH | CH | CH | CH | t-Bu | 2-Me | $CF_3$ | Br |
| K-31 | CH | CH | CH | CH | i-Pr | 2-Cl | $CF_3$ | Br |
| K-31 | CH | CH | CH | CH | t-Bu | 2-Cl | $CF_3$ | Br |

TABLE 17-continued

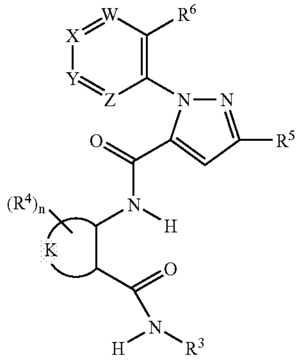

| K | W | X | Y | Z | $R^3$ | $(R^4)_n$ | $R^5$ | $R^6$ |
|---|---|---|---|---|---|---|---|---|
| K-31 | CH | CH | CH | CH | i-Pr | 2-Me | $CF_3$ | CN |
| K-31 | CH | CH | CH | CH | t-Bu | 2-Me | $CF_3$ | CN |
| K-31 | CH | CH | CH | CH | i-Pr | 2-Cl | $CF_3$ | CN |
| K-31 | CH | CH | CH | CH | t-Bu | 2-Cl | $CF_3$ | CN |
| K-31 | CH | CH | CH | N | i-Pr | 2-Me | $CF_3$ | Me |
| K-31 | CH | CH | CH | N | t-Bu | 2-Me | $CF_3$ | Me |
| K-31 | CH | CH | CH | N | i-Pr | 2-Cl | $CF_3$ | Me |
| K-31 | CH | CH | CH | N | t-Bu | 2-Cl | $CF_3$ | Me |
| K-31 | CH | CH | CH | N | i-Pr | 2-Me | $CF_3$ | F |
| K-31 | CH | CH | CH | N | t-Bu | 2-Me | $CF_3$ | F |
| K-31 | CH | CH | CH | N | i-Pr | 2-Cl | $CF_3$ | F |
| K-31 | CH | CH | CH | N | t-Bu | 2-Cl | $CF_3$ | F |
| K-31 | CH | CH | CH | N | i-Pr | 2-Me | $CF_3$ | Cl |
| K-31 | CH | CH | CH | N | t-Bu | 2-Me | $CF_3$ | Cl |
| K-31 | CH | CH | CH | N | i-Pr | 2-Cl | $CF_3$ | Cl |
| K-31 | CH | CH | CH | N | t-Bu | 2-Cl | $CF_3$ | Cl |
| K-31 | CH | CH | CH | N | i-Pr | 2-Me | $CF_3$ | Br |
| K-31 | CH | CH | CH | N | t-Bu | 2-Me | $CF_3$ | Br |
| K-31 | CH | CH | CH | N | i-Pr | 2-Cl | $CF_3$ | Br |
| K-31 | CH | CH | CH | N | t-Bu | 2-Cl | $CF_3$ | Br |
| K-31 | CH | CH | CH | N | i-Pr | 2-Me | $CF_3$ | CN |
| K-31 | CH | CH | CH | N | t-Bu | 2-Me | $CF_3$ | CN |
| K-31 | CH | CH | CH | N | i-Pr | 2-Cl | $CF_3$ | CN |
| K-31 | CH | CH | CH | N | i-Pr | 2-Cl | $CF_3$ | CN |
| K-31 | CH | CH | CH | CH | i-Pr | 2-Me | $CF_3$ | Me |
| K-31 | CH | CH | CH | CH | t-Bu | 2-Me | $CF_3$ | Me |
| K-31 | CH | CH | CH | CH | i-Pr | 2-Cl | $CF_3$ | Me |
| K-31 | CH | CH | CH | CH | t-Bu | 2-Cl | $CF_3$ | Me |
| K-31 | CH | CH | CH | CH | i-Pr | 2-Me | $CF_3$ | F |
| K-31 | CH | CH | CH | CH | t-Bu | 2-Me | $CF_3$ | F |
| K-31 | CH | CH | CH | CH | i-Pr | 2-Cl | $CF_3$ | F |
| K-31 | CH | CH | CH | CH | t-Bu | 2-Cl | $CF_3$ | F |
| K-31 | CH | CH | CH | CH | i-Pr | 2-Me | $CF_3$ | Cl |
| K-31 | CH | CH | CH | CH | t-Bu | 2-Me | $CF_3$ | Cl |
| K-31 | CH | CH | CH | CH | i-Pr | 2-Cl | $CF_3$ | Cl |
| K-31 | CH | CH | CH | CH | t-Bu | 2-Cl | $CF_3$ | Cl |
| K-31 | CH | CH | CH | CH | i-Pr | 2-Me | $CF_3$ | Br |
| K-31 | CH | CH | CH | CH | t-Bu | 2-Me | $CF_3$ | Br |
| K-31 | CH | CH | CH | CH | i-Pr | 2-Cl | $CF_3$ | Br |
| K-31 | CH | CH | CH | CH | t-Bu | 2-Cl | $CF_3$ | Br |
| K-31 | CH | CH | CH | CH | i-Pr | 2-Me | $CF_3$ | CN |
| K-31 | CH | CH | CH | CH | t-Bu | 2-Me | $CF_3$ | CN |
| K-31 | CH | CH | CH | CH | i-Pr | 2-Cl | $CF_3$ | CN |
| K-31 | CH | CH | CH | CH | t-Bu | 2-Cl | $CF_3$ | CN |
| K-31 | CH | CH | CH | N | i-Pr | 2-Me | $CF_3$ | Me |
| K-31 | CH | CH | CH | N | t-Bu | 2-Me | $CF_3$ | Me |
| K-31 | CH | CH | CH | N | i-Pr | 2-Cl | $CF_3$ | Me |
| K-31 | CH | CH | CH | N | t-Bu | 2-Cl | $CF_3$ | Me |
| K-31 | CH | CH | CH | N | i-Pr | 2-Me | $CF_3$ | F |
| K-31 | CH | CH | CH | N | t-Bu | 2-Me | $CF_3$ | F |
| K-31 | CH | CH | CH | N | i-Pr | 2-Cl | $CF_3$ | F |
| K-31 | CH | CH | CH | N | t-Bu | 2-Cl | $CF_3$ | F |
| K-31 | CH | CH | CH | N | i-Pr | 2-Me | $CF_3$ | Cl |
| K-31 | CH | CH | CH | N | t-Bu | 2-Me | $CF_3$ | Cl |
| K-31 | CH | CH | CH | N | i-Pr | 2-Cl | $CF_3$ | Cl |
| K-31 | CH | CH | CH | N | t-Bu | 2-Cl | $CF_3$ | Cl |
| K-31 | CH | CH | CH | N | i-Pr | 2-Me | $CF_3$ | Br |
| K-31 | CH | CH | CH | N | t-Bu | 2-Me | $CF_3$ | Br |
| K-31 | CH | CH | CH | N | i-Pr | 2-Cl | $CF_3$ | Br |

TABLE 17-continued

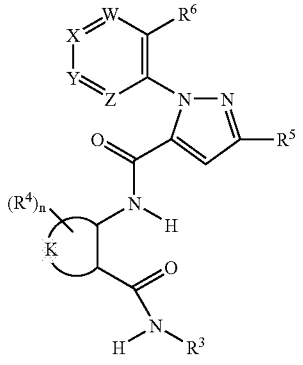

| K | W | X | Y | Z | $R^3$ | $(R^4)_n$ | $R^5$ | $R^6$ |
|---|---|---|---|---|---|---|---|---|
| K-31 | CH | CH | CH | N | t-Bu | 2-Cl | $CF_3$ | Br |
| K-31 | CH | CH | CH | N | i-Pr | 2-Me | $CF_3$ | CN |
| K-31 | CH | CH | CH | N | t-Bu | 2-Me | $CF_3$ | CN |
| K-31 | CH | CH | CH | N | i-Pr | 2-Cl | $CF_3$ | CN |
| K-31 | CH | CH | CH | N | i-Pr | 2-Cl | $CF_3$ | CN |
| K-33 | CH | CH | CH | CH | i-Pr | 6-Me | $CF_3$ | Me |
| K-33 | CH | CH | CH | CH | t-Bu | 6-Me | $CF_3$ | Me |
| K-33 | CH | CH | CH | CH | i-Pr | 6-Cl | $CF_3$ | Me |
| K-33 | CH | CH | CH | CH | t-Bu | 6-Cl | $CF_3$ | Me |
| K-33 | CH | CH | CH | CH | i-Pr | 6-Me | $CF_3$ | F |
| K-33 | CH | CH | CH | CH | t-Bu | 6-Me | $CF_3$ | F |
| K-33 | CH | CH | CH | CH | i-Pr | 6-Cl | $CF_3$ | F |
| K-33 | CH | CH | CH | CH | t-Bu | 6-Cl | $CF_3$ | F |
| K-33 | CH | CH | CH | CH | i-Pr | 6-Me | $CF_3$ | Cl |
| K-33 | CH | CH | CH | CH | t-Bu | 6-Me | $CF_3$ | Cl |
| K-33 | CH | CH | CH | CH | i-Pr | 6-Cl | $CF_3$ | Cl |
| K-33 | CH | CH | CH | CH | t-Bu | 6-Cl | $CF_3$ | Cl |
| K-33 | CH | CH | CH | CH | i-Pr | 6-Me | $CF_3$ | Br |
| K-33 | CH | CH | CH | CH | t-Bu | 6-Me | $CF_3$ | Br |
| K-33 | CH | CH | CH | CH | i-Pr | 6-Cl | $CF_3$ | Br |
| K-33 | CH | CH | CH | CH | t-Bu | 6-Cl | $CF_3$ | Br |
| K-33 | CH | CH | CH | CH | i-Pr | 6-Me | $CF_3$ | CN |
| K-33 | CH | CH | CH | CH | t-Bu | 6-Me | $CF_3$ | CN |
| K-33 | CH | CH | CH | CH | i-Pr | 6-Cl | $CF_3$ | CN |
| K-33 | CH | CH | CH | CH | t-Bu | 6-Cl | $CF_3$ | CN |
| K-33 | CH | CH | CH | N | i-Pr | 6-Me | $CF_3$ | Me |
| K-33 | CH | CH | CH | N | t-Bu | 6-Me | $CF_3$ | Me |
| K-33 | CH | CH | CH | N | i-Pr | 6-Cl | $CF_3$ | Me |
| K-33 | CH | CH | CH | N | t-Bu | 6-Cl | $CF_3$ | Me |
| K-33 | CH | CH | CH | N | i-Pr | 6-Me | $CF_3$ | F |
| K-33 | CH | CH | CH | N | t-Bu | 6-Me | $CF_3$ | F |
| K-33 | CH | CH | CH | N | i-Pr | 6-Cl | $CF_3$ | F |
| K-33 | CH | CH | CH | N | t-Bu | 6-Cl | $CF_3$ | F |
| K-33 | CH | CH | CH | N | i-Pr | 6-Me | $CF_3$ | Cl |
| K-33 | CH | CH | CH | N | t-Bu | 6-Me | $CF_3$ | Cl |
| K-33 | CH | CH | CH | N | i-Pr | 6-Cl | $CF_3$ | Cl |
| K-33 | CH | CH | CH | N | t-Bu | 6-Cl | $CF_3$ | Cl |
| K-33 | CH | CH | CH | N | i-Pr | 6-Me | $CF_3$ | Br |
| K-33 | CH | CH | CH | N | t-Bu | 6-Me | $CF_3$ | Br |
| K-33 | CH | CH | CH | N | i-Pr | 6-Cl | $CF_3$ | Br |
| K-33 | CH | CH | CH | N | t-Bu | 6-Cl | $CF_3$ | Br |
| K-33 | CH | CH | CH | N | i-Pr | 6-Me | $CF_3$ | CN |
| K-33 | CH | CH | CH | N | t-Bu | 6-Me | $CF_3$ | CN |
| K-33 | CH | CH | CH | N | i-Pr | 6-Cl | $CF_3$ | CN |
| K-33 | CH | CH | CH | N | i-Pr | 6-Cl | $CF_3$ | CN |
| K-33 | CH | CH | CH | CH | i-Pr | 6-Me | $CF_3$ | Me |
| K-33 | CH | CH | CH | CH | t-Bu | 6-Me | $CF_3$ | Me |

TABLE 17-continued

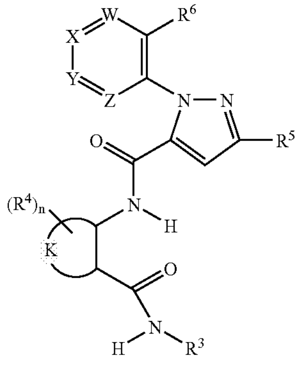

| K | W | X | Y | Z | $R^3$ | $(R^4)_n$ | $R^5$ | $R^6$ |
|---|---|---|---|---|---|---|---|---|
| K-33 | CH | CH | CH | CH | i-Pr | 6-Cl | $CF_3$ | Me |
| K-33 | CH | CH | CH | CH | t-Bu | 6-Cl | $CF_3$ | Me |
| K-33 | CH | CH | CH | CH | i-Pr | 6-Me | $CF_3$ | F |
| K-33 | CH | CH | CH | CH | t-Bu | 6-Me | $CF_3$ | F |
| K-33 | CH | CH | CH | CH | i-Pr | 6-Cl | $CF_3$ | F |
| K-33 | CH | CH | CH | CH | t-Bu | 6-Cl | $CF_3$ | F |
| K-33 | CH | CH | CH | CH | i-Pr | 6-Me | $CF_3$ | Cl |
| K-33 | CH | CH | CH | CH | t-Bu | 6-Me | $CF_3$ | Cl |
| K-33 | CH | CH | CH | CH | i-Pr | 6-Cl | $CF_3$ | Cl |
| K-33 | CH | CH | CH | CH | t-Bu | 6-Cl | $CF_3$ | Cl |
| K-33 | CH | CH | CH | CH | i-Pr | 6-Me | $CF_3$ | Br |
| K-33 | CH | CH | CH | CH | t-Bu | 6-Me | $CF_3$ | Br |
| K-33 | CH | CH | CH | CH | i-Pr | 6-Cl | $CF_3$ | Br |
| K-33 | CH | CH | CH | CH | t-Bu | 6-Cl | $CF_3$ | Br |
| K-33 | CH | CH | CH | CH | i-Pr | 6-Me | $CF_3$ | CN |
| K-33 | CH | CH | CH | CH | t-Bu | 6-Me | $CF_3$ | CN |
| K-33 | CH | CH | CH | CH | i-Pr | 6-Cl | $CF_3$ | CN |
| K-33 | CH | CH | CH | CH | t-Bu | 6-Cl | $CF_3$ | CN |
| K-33 | CH | CH | CH | N | i-Pr | 6-Me | $CF_3$ | Me |
| K-33 | CH | CH | CH | N | t-Bu | 6-Me | $CF_3$ | Me |
| K-33 | CH | CH | CH | N | i-Pr | 6-Cl | $CF_3$ | Me |
| K-33 | CH | CH | CH | N | t-Bu | 6-Cl | $CF_3$ | Me |
| K-33 | CH | CH | CH | N | i-Pr | 6-Me | $CF_3$ | F |
| K-33 | CH | CH | CH | N | t-Bu | 6-Me | $CF_3$ | F |
| K-33 | CH | CH | CH | N | i-Pr | 6-Cl | $CF_3$ | F |
| K-33 | CH | CH | CH | N | t-Bu | 6-Cl | $CF_3$ | F |
| K-33 | CH | CH | CH | N | i-Pr | 6-Me | $CF_3$ | Cl |
| K-33 | CH | CH | CH | N | t-Bu | 6-Me | $CF_3$ | Cl |
| K-33 | CH | CH | CH | N | i-Pr | 6-Cl | $CF_3$ | Cl |
| K-33 | CH | CH | CH | N | t-Bu | 6-Cl | $CF_3$ | Cl |
| K-33 | CH | CH | CH | N | i-Pr | 6-Me | $CF_3$ | Br |
| K-33 | CH | CH | CH | N | t-Bu | 6-Me | $CF_3$ | Br |
| K-33 | CH | CH | CH | N | i-Pr | 6-Cl | $CF_3$ | Br |
| K-33 | CH | CH | CH | N | t-Bu | 6-Cl | $CF_3$ | Br |
| K-33 | CH | CH | CH | N | i-Pr | 6-Me | $CF_3$ | CN |
| K-33 | CH | CH | CH | N | t-Bu | 6-Me | $CF_3$ | CN |
| K-33 | CH | CH | CH | N | i-Pr | 6-Cl | $CF_3$ | CN |
| K-33 | CH | CH | CH | N | i-Pr | 6-Cl | $CF_3$ | CN |

TABLE 18

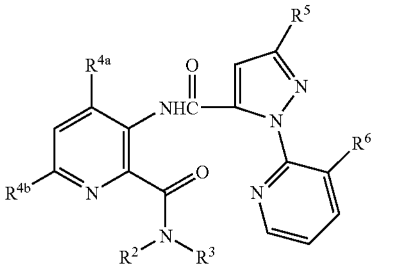

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | $R^5$ is Cl | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Br |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is Br | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |

TABLE 18-continued

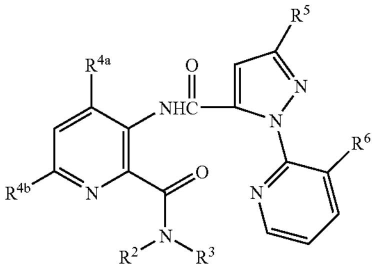

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is $CF_3$ | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is $OCH_2CF_3$ | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |

TABLE 18-continued

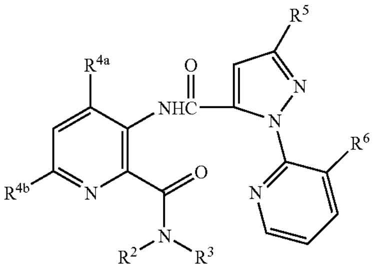

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 19

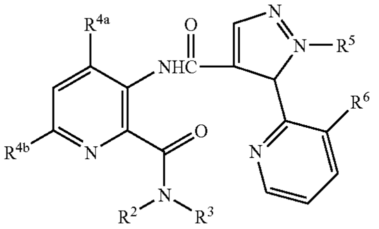

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $R^5$ is $CHF_2$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |

TABLE 19-continued

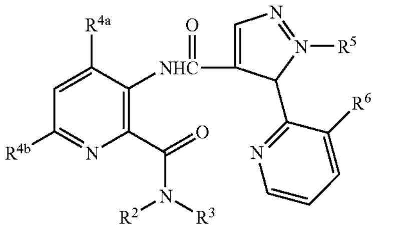

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Br |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

$R^5$ is $CH_2CF_3$

| | | | | | | | | | | | |
|---|---|---|---|---|---|---|---|---|---|---|---|
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |

TABLE 19-continued

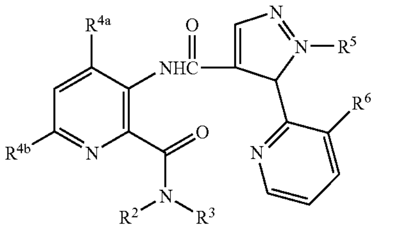

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | | $R^5$ is $CH_2CF_3$ | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | | $R^5$ is $CF_2CHF_2$ | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |

TABLE 19-continued

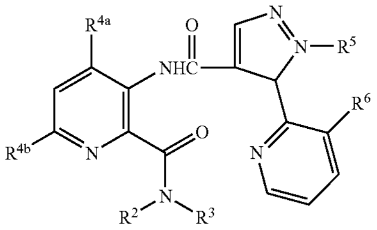

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 20

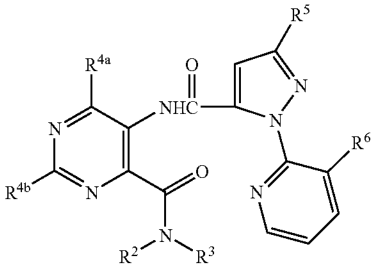

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | | $R^5$ is Cl | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |

TABLE 20-continued

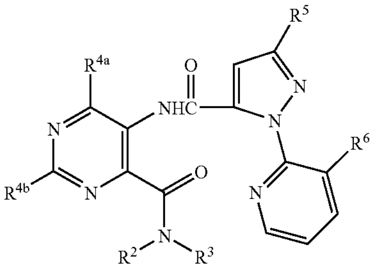

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Br |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is Br | | | | | | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $CF_3$ | | | | | | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |

TABLE 20-continued

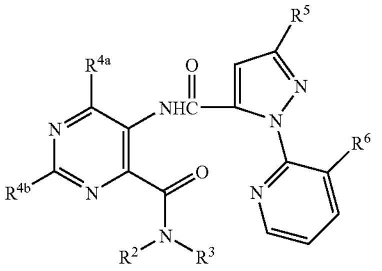

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is $OCH_2CF_3$ | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |

TABLE 20-continued

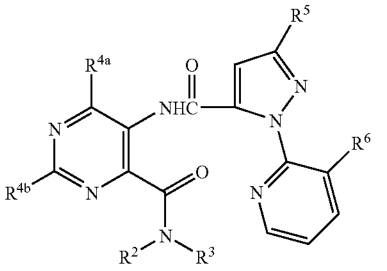

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 21

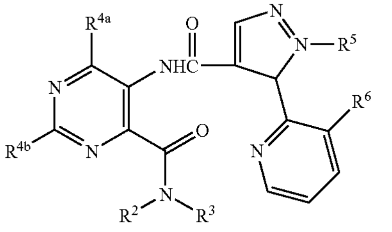

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | $R^5$ is $CHF_2$ | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Br |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |

TABLE 21-continued

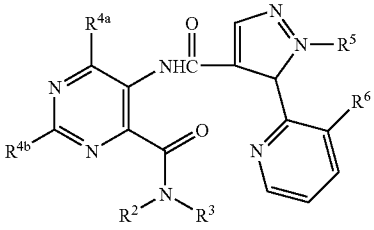

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is $CH_2CF_3$ | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is $CF_2CHF_2$ | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |

TABLE 21-continued

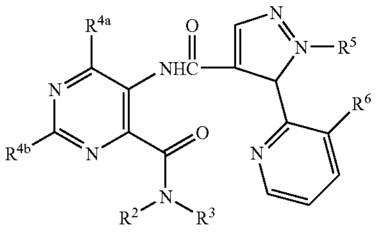

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is $OCH_2CF_3$ | | | | | | |
| $CH_3$ | H | Cl | $CH_3$ | H | Cl | $CH_3$ | H | Cl | $CH_3$ | H | $CH_3$ |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 22

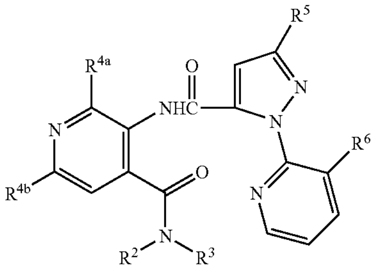

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | | $R^5$ is Cl | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | | $R^5$ is Br | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |

TABLE 22-continued

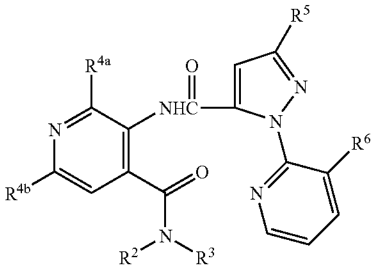

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $OCH_2CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |

TABLE 22-continued

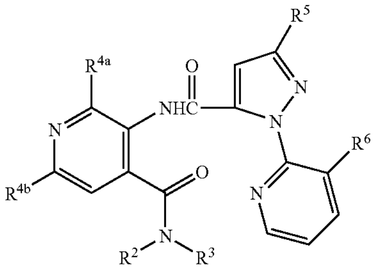

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 23

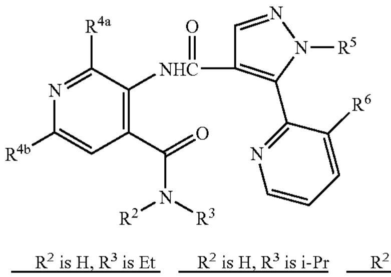

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | | $R^5$ is $CHF_2$ | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |

TABLE 23-continued

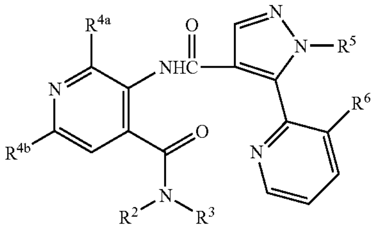

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $CH_2CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |

TABLE 23-continued

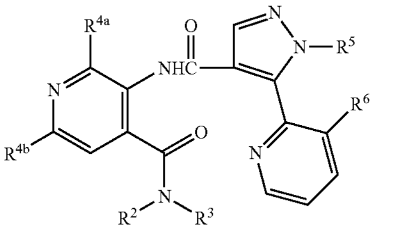

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $CF_2CF_2$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 24

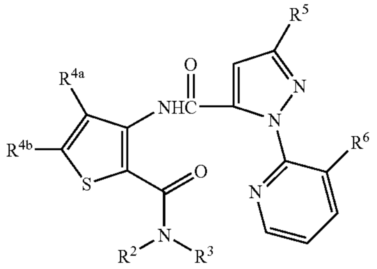

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | | $R^5$ is Cl | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | | $R^5$ is Br | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |

TABLE 24-continued

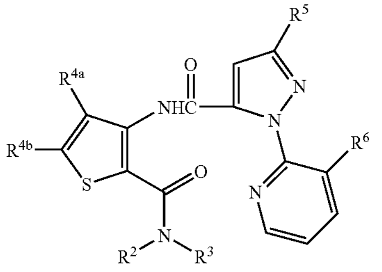

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $OCH_2CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |

TABLE 24-continued

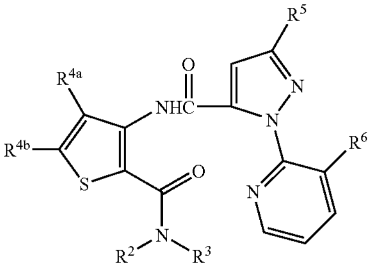

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 25

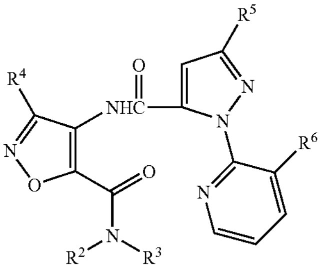

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| | | | | | V is CH | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Cl | Cl | CN | Cl | Cl | CN | Cl | Cl | CN | Cl | Cl | CN |

TABLE 25-continued

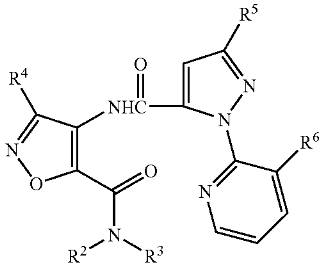

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | Br | Br | Cl |
| Br | Br | Br | Br | Br | Br | Br | Br | Br | Br | Br | Br |
| Br | Br | CN | Br | Br | CN | Br | Br | CN | Br | Br | CN |
| Br | Cl | Cl | Br | Cl | Cl | Br | Cl | Cl | Br | Br | Br |
| Br | Cl | Br | Br | Cl | Br | Br | Cl | Br | Br | Br | Br |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | $CF_3$ | Br | Cl |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |
| | | | | | V is N | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Cl | Cl | CN | Cl | Cl | CN | Cl | Cl | CN | Cl | Cl | CN |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | Br | Br | Cl |
| Br | Br | Br | Br | Br | Br | Br | Br | Br | Cl | Br | Br |
| Br | Br | CN | Br | Br | CN | Br | Br | CN | Cl | Br | CN |
| Br | Cl | Cl | Br | Cl | Cl | Br | Cl | Cl | Br | Br | Br |
| Br | Cl | Br | Br | Cl | Br | Br | Cl | Br | Br | Br | Br |

TABLE 25-continued

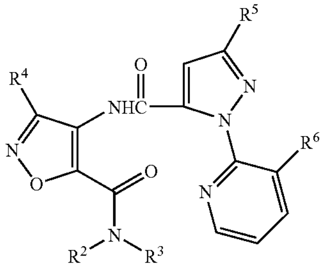

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | $CF_3$ | Br | Cl |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |

TABLE 26

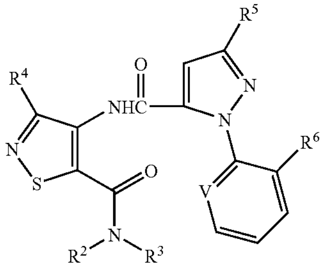

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| V is CH | | | | | | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |

TABLE 26-continued

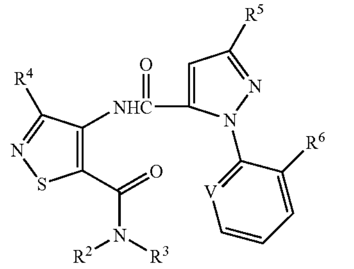

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Cl | Cl | CN | Cl | Cl | CN | Cl | Cl | CN | Cl | Cl | CN |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | Br | Br | Cl |
| Br | Br | Br | Br | Br | Br | Br | Br | Br | Cl | Br | Br |
| Br | Br | CN | Br | Br | CN | Br | Br | CN | Cl | Br | CN |
| Br | Cl | Cl | Br | Cl | Cl | Br | Cl | Cl | Br | Br | Br |
| Br | Cl | Br | Br | Cl | Br | Br | Cl | Br | Br | Br | Br |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | $CF_3$ | Br | Cl |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |
| | | | | | V is N | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Cl | Cl | CN | Cl | Cl | CN | Cl | Cl | CN | Cl | Cl | CN |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | Br | Br | Cl |
| Br | Br | Br | Br | Br | Br | Br | Br | Br | Cl | Br | Br |
| Br | Br | CN | Br | Br | CN | Br | Br | CN | Cl | Br | CN |
| Br | Cl | Cl | Br | Cl | Cl | Br | Cl | Cl | Br | Br | Br |

TABLE 26-continued

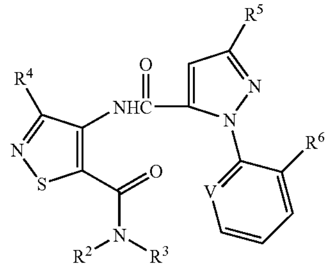

| R² is H, R³ is Me | | | R² is H, R³ is Et | | | R² is H, R³ is i-Pr | | | R² is Me, R³ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Br | Cl | Br | Br | Cl | Br | Br | Cl | Br | Br | Br | Br |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | $CF_3$ | Br | Cl |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |

TABLE 27

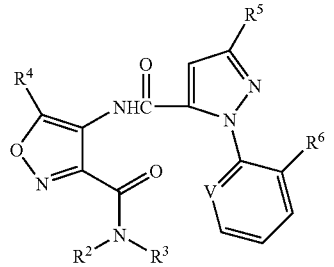

| R² is H, R³ is Me | | | R² is H, R³ is Et | | | R² is H, R³ is i-Pr | | | R² is Me, R³ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| | | | | | V is CH | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |
| Cl | Cl | Cl | Cl | Cl | Cl | Cl | Cl | Cl | Cl | Cl | Cl |

TABLE 27-continued

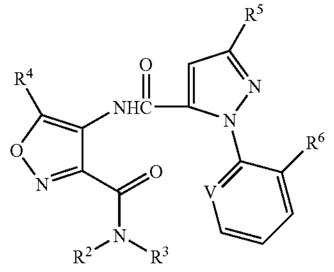

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Cl | Cl | Br | Cl | Cl | Br | Cl | Cl | Br | Cl | Cl | Br |
| Cl | Cl | CN | Cl | Cl | CN | Cl | Cl | CN | Cl | Cl | CN |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | Br | Br | Cl |
| Br | Br | Br | Br | Br | Br | Br | Br | Br | Cl | Br | Br |
| Br | Br | CN | Br | Br | CN | Br | Br | CN | Cl | Br | CN |
| Br | Cl | Cl | Br | Cl | Cl | Br | Cl | Cl | Br | Br | Br |
| Br | Cl | Br | Br | Cl | Br | Br | Cl | Br | Br | Br | Br |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | $CF_3$ | Br | Cl |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |
| V is N | | | | | | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Cl | Cl | CN | Cl | Cl | CN | Cl | Cl | CN | Cl | Cl | CN |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | Br | Br | Cl |
| Br | Br | Br | Br | Br | Br | Br | Br | Br | Cl | Br | Br |
| Br | Br | CN | Br | Br | CN | Br | Br | CN | Cl | Br | CN |

TABLE 27-continued

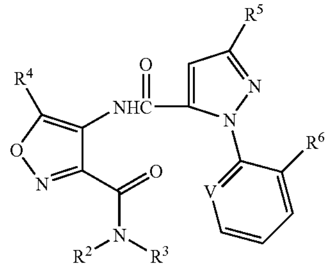

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Br | Cl | Cl | Br | Cl | Cl | Br | Cl | Cl | Br | Br | Br |
| Br | Cl | Br | Br | Cl | Br | Br | Cl | Br | Br | Br | Br |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | $CF_3$ | Br | Cl |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |

TABLE 28

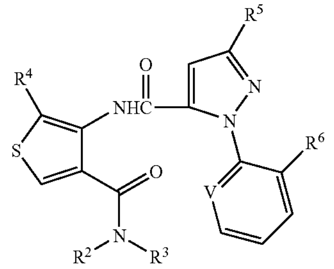

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| | | | | | V is CH | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |

TABLE 28-continued

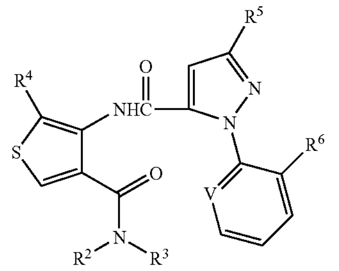

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Cl | Cl | CN | Cl | Cl | CN | Cl | Cl | CN | Cl | Cl | CN |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | | | |
| Br | Br | Br | Br | Br | Br | Br | Br | Br | Cl | Br | Br |
| Br | Br | CN | Br | Br | CN | Br | Br | CN | Cl | Br | CN |
| Br | Cl | Cl | Br | Cl | Cl | Br | Cl | Cl | Br | Br | Br |
| Br | Cl | Br | Br | Cl | Br | Br | Cl | Br | Br | Br | Br |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | | | |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | | | |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |
| V is N | | | | | | | | | | | |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Br | CN | Cl | Br | CN | Cl | Br | CN | Cl | Br | CN |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Cl | Cl | CN | Cl | Cl | CN | Cl | Cl | CN | Cl | Cl | CN |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | $CF_3$ | CN | Cl | $CF_3$ | CN | Cl | $CF_3$ | CN | Cl | $CF_3$ | CN |

TABLE 28-continued

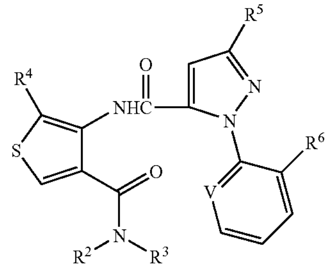

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^4$ | $R^5$ | $R^6$ | $R^4$ | $R^5$ | $R^6$ | $R^4$ | $R^5$ | $R^6$ | $R^4$ | $R^5$ | $R^6$ |
| Cl | $OCH_2CF_3$ | Cl | Cl | $OCH_2CF_3$ | Cl | Cl | $OCH_2CF_3$ | Cl | Cl | $OCH_2CF_3$ | Cl |
| Cl | $OCH_2CF_3$ | Br | Cl | $OCH_2CF_3$ | Br | Cl | $OCH_2CF_3$ | Br | Cl | $OCH_2CF_3$ | Br |
| Cl | $OCH_2CF_3$ | CN | Cl | $OCH_2CF_3$ | CN | Cl | $OCH_2CF_3$ | CN | Cl | $OCH_2CF_3$ | CN |
| Br | Br | Cl | Br | Br | Cl | Br | Br | Cl | | | |
| Br | Br | Br | Br | Br | Br | Br | Br | Br | Cl | Br | Br |
| Br | Br | CN | Br | Br | CN | Br | Br | CN | Cl | Br | CN |
| Br | Cl | Cl | Br | Cl | Cl | Br | Cl | Cl | Br | Br | Br |
| Br | Cl | Br | Br | Cl | Br | Br | Cl | Br | Br | Br | Br |
| Br | Cl | CN | Br | Cl | CN | Br | Cl | CN | Cl | Br | CN |
| Br | $CF_3$ | Cl | Br | $CF_3$ | Cl | Br | $CF_3$ | Cl | Cl | $CF_3$ | Cl |
| Br | $CF_3$ | Br | Br | $CF_3$ | Br | Br | $CF_3$ | Br | Cl | $CF_3$ | Br |
| Br | $CF_3$ | CN | Br | $CF_3$ | CN | Br | $CF_3$ | CN | Cl | $CF_3$ | CN |
| Br | $OCH_2CF_3$ | Cl | Br | $OCH_2CF_3$ | Cl | Br | $OCH_2CF_3$ | Cl | Cl | $OCH_2CF_3$ | Cl |
| Br | $OCH_2CF_3$ | Br | Br | $OCH_2CF_3$ | Br | Br | $OCH_2CF_3$ | Br | Cl | $OCH_2CF_3$ | Br |
| Br | $OCH_2CF_3$ | CN | Br | $OCH_2CF_3$ | CN | Br | $OCH_2CF_3$ | CN | Cl | $OCH_2CF_3$ | CN |
| $CH_3$ | Br | Cl | $CH_3$ | Br | Cl | $CH_3$ | Br | Cl | | | |
| $CH_3$ | Br | Br | $CH_3$ | Br | Br | $CH_3$ | Br | Br | $CH_3$ | Br | Br |
| $CH_3$ | Br | CN | $CH_3$ | Br | CN | $CH_3$ | Br | CN | $CH_3$ | Br | CN |
| $CH_3$ | Cl | Cl | $CH_3$ | Cl | Cl | $CH_3$ | Cl | Cl | $CH_3$ | Br | Br |
| $CH_3$ | Cl | Br | $CH_3$ | Cl | Br | $CH_3$ | Cl | Br | $CH_3$ | Br | Br |
| $CH_3$ | Cl | CN | $CH_3$ | Cl | CN | $CH_3$ | Cl | CN | $CH_3$ | Br | CN |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | $CF_3$ | CN | $CH_3$ | $CF_3$ | CN | $CH_3$ | $CF_3$ | CN | $CH_3$ | $CF_3$ | CN |
| $CH_3$ | $OCH_2CF_3$ | Cl | $CH_3$ | $OCH_2CF_3$ | Cl | $CH_3$ | $OCH_2CF_3$ | Cl | $CH_3$ | $OCH_2CF_3$ | Cl |
| $CH_3$ | $OCH_2CF_3$ | Br | $CH_3$ | $OCH_2CF_3$ | Br | $CH_3$ | $OCH_2CF_3$ | Br | $CH_3$ | $OCH_2CF_3$ | Br |
| $CH_3$ | $OCH_2CF_3$ | CN | $CH_3$ | $OCH_2CF_3$ | CN | $CH_3$ | $OCH_2CF_3$ | CN | $CH_3$ | $OCH_2CF_3$ | CN |
| $CF_3$ | Br | Cl | $CF_3$ | Br | Cl | $CF_3$ | Br | Cl | | | |
| $CF_3$ | Br | Br | $CF_3$ | Br | Br | $CF_3$ | Br | Br | $CF_3$ | Br | Br |
| $CF_3$ | Br | CN | $CF_3$ | Br | CN | $CF_3$ | Br | CN | $CF_3$ | Br | CN |
| $CF_3$ | Cl | Cl | $CF_3$ | Cl | Cl | $CF_3$ | Cl | Cl | $CF_3$ | Br | Br |
| $CF_3$ | Cl | Br | $CF_3$ | Cl | Br | $CF_3$ | Cl | Br | $CF_3$ | Br | Br |
| $CF_3$ | Cl | CN | $CF_3$ | Cl | CN | $CF_3$ | Cl | CN | $CF_3$ | Br | CN |
| $CF_3$ | $CF_3$ | Cl | $CF_3$ | $CF_3$ | Cl | $CF_3$ | $CF_3$ | Cl | $CF_3$ | $CF_3$ | Cl |
| $CF_3$ | $CF_3$ | Br | $CF_3$ | $CF_3$ | Br | $CF_3$ | $CF_3$ | Br | $CF_3$ | $CF_3$ | Br |
| $CF_3$ | $CF_3$ | CN | $CF_3$ | $CF_3$ | CN | $CF_3$ | $CF_3$ | CN | $CF_3$ | $CF_3$ | CN |
| $CF_3$ | $OCH_2CF_3$ | Cl | $CF_3$ | $OCH_2CF_3$ | Cl | $CF_3$ | $OCH_2CF_3$ | Cl | $CF_3$ | $OCH_2CF_3$ | Cl |
| $CF_3$ | $OCH_2CF_3$ | Br | $CF_3$ | $OCH_2CF_3$ | Br | $CF_3$ | $OCH_2CF_3$ | Br | $CF_3$ | $OCH_2CF_3$ | Br |
| $CF_3$ | $OCH_2CF_3$ | CN | $CF_3$ | $OCH_2CF_3$ | CN | $CF_3$ | $OCH_2CF_3$ | CN | $CF_3$ | $OCH_2CF_3$ | CN |

TABLE 29

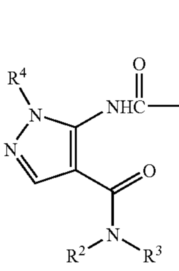

| $R^2$ is H, $R^3$ is Me | | $R^2$ is H, $R^3$ is Et | | $R^2$ is H, $R^3$ is i-Pr | | $R^2$ is Me, $R^3$ is Me | |
|---|---|---|---|---|---|---|---|
| $R^5$ | $R^6$ | $R^5$ | $R^6$ | $R^5$ | $R^6$ | $R^5$ | $R^6$ |
| | | | $CHF_2$ | | | | |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| | | | $R^4$ is $CH_3$ | | | | |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |

TABLE 29-continued

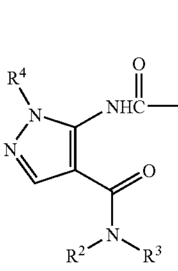

| $R^2$ is H, $R^3$ is Me | | $R^2$ is H, $R^3$ is Et | | $R^2$ is H, $R^3$ is i-Pr | | $R^2$ is Me, $R^3$ is Me | |
|---|---|---|---|---|---|---|---|
| $R^5$ | $R^6$ | $R^5$ | $R^6$ | $R^5$ | $R^6$ | $R^5$ | $R^6$ |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| | | | $R^4$ is $CF_3$ | | | | |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |

TABLE 29-continued

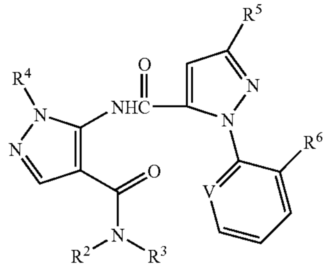

| $R^2$ is H, $R^3$ is Me | | $R^2$ is H, $R^3$ is Et | | $R^2$ is H, $R^3$ is i-Pr | | $R^2$ is Me, $R^3$ is Me | |
|---|---|---|---|---|---|---|---|
| $R^5$ | $R^6$ | $R^5$ | $R^6$ | $R^5$ | $R^6$ | $R^5$ | $R^6$ |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| $R^4$ is $CH_2CF_3$ | | | | | | | |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |

TABLE 29-continued

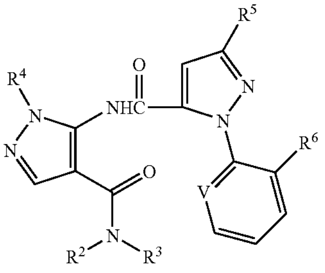

| $R^2$ is H, $R^3$ is Me | | $R^2$ is H, $R^3$ is Et | | $R^2$ is H, $R^3$ is i-Pr | | $R^2$ is Me, $R^3$ is Me | |
|---|---|---|---|---|---|---|---|
| $R^5$ | $R^6$ | $R^5$ | $R^6$ | $R^5$ | $R^6$ | $R^5$ | $R^6$ |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |
| Br | Cl | Br | Cl | Br | Cl | Br | Cl |
| Br | Br | Br | Br | Br | Br | Br | Br |
| Br | CN | Br | CN | Br | CN | Br | CN |
| Cl | Cl | Cl | Cl | Cl | Cl | Cl | Cl |
| Cl | Br | Cl | Br | Cl | Br | Cl | Br |
| Cl | CN | Cl | CN | Cl | CN | Cl | CN |
| $CF_3$ | Cl | $CF_3$ | Cl | $CF_3$ | Cl | $CF_3$ | Cl |
| $CF_3$ | Br | $CF_3$ | Br | $CF_3$ | Br | $CF_3$ | Br |
| $CF_3$ | CN | $CF_3$ | CN | $CF_3$ | CN | $CF_3$ | CN |
| $OCH_2CF_3$ | Cl | $OCH_2CF_3$ | Cl | $OCH_2CF_3$ | Cl | $OCH_2CF_3$ | Cl |
| $OCH_2CF_3$ | Br | $OCH_2CF_3$ | Br | $OCH_2CF_3$ | Br | $OCH_2CF_3$ | Br |
| $OCH_2CF_3$ | CN | $OCH_2CF_3$ | CN | $OCH_2CF_3$ | CN | $OCH_2CF_3$ | CN |

TABLE 30

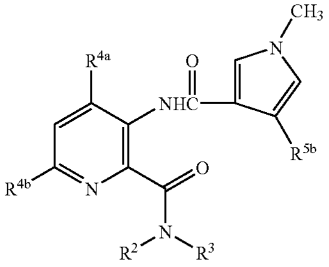

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | $R^{5b}$ is Cl | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^5$ is $OCF_3$ | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |

TABLE 30-continued

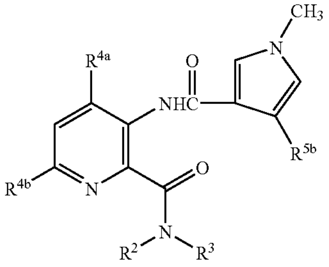

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^5$ is $CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^{5b}$ is $CF(CF_3)_2$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |

TABLE 30-continued

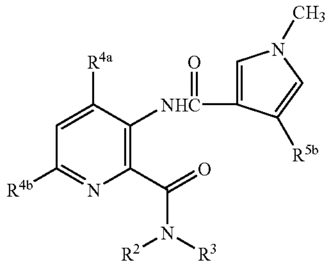

| R² is H, R³ is Me | | | R² is H, R³ is Et | | | R² is H, R³ is i-Pr | | | R² is Me, R³ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 31

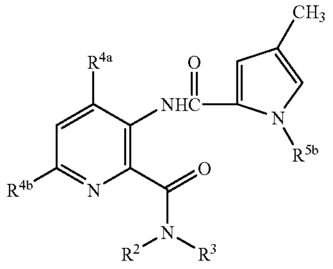

| R² is H, R³ is Me | | | R² is H, R³ is Et | | | R² is H, R³ is i-Pr | | | R² is Me, R³ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | $R^{5b}$ is $CHF_2$ | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |

TABLE 31-continued

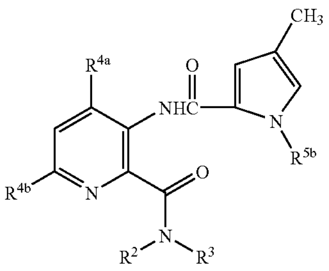

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^{5b}$ is $CH_2CF_3$ | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |

TABLE 31-continued

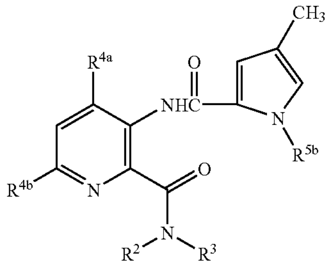

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^{5b}$ is $CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^{5b}$ is $CF_2CHF_2$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |

TABLE 31-continued

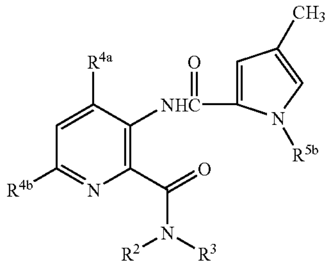

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 32

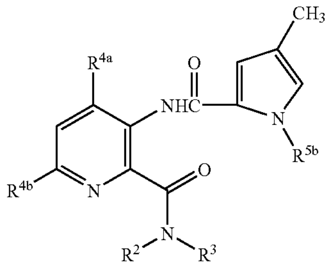

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| $R^{5b}$ is $CHF_2$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |

TABLE 32-continued

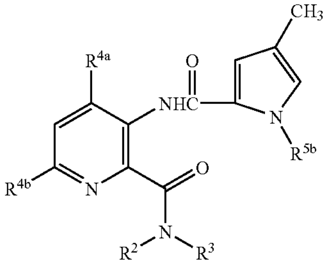

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| $R^{5b}$ is $CH_2CF_3$ | | | | | | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

TABLE 32-continued

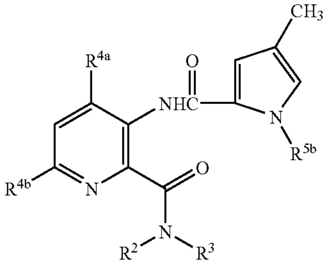

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| | | | | | $R^{5b}$ is $CF_3$ | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |
| | | | | | $R^{5b}$ is $CF_2CHF_2$ | | | | | | |
| $CH_3$ | H | Cl | $CH_3$ | H | Cl | $CH_3$ | H | Cl | $CH_3$ | H | Cl |
| $CH_3$ | H | Br | $CH_3$ | H | Br | $CH_3$ | H | Br | $CH_3$ | H | Br |
| $CH_3$ | I | Cl | $CH_3$ | I | Cl | $CH_3$ | I | Cl | $CH_3$ | I | Cl |
| $CH_3$ | I | Br | $CH_3$ | I | Br | $CH_3$ | I | Br | $CH_3$ | I | Br |
| $CH_3$ | F | Cl | $CH_3$ | F | Cl | $CH_3$ | F | Cl | $CH_3$ | F | Cl |
| $CH_3$ | F | Br | $CH_3$ | F | Br | $CH_3$ | F | Br | $CH_3$ | F | Br |
| $CH_3$ | $CF_3$ | Cl | $CH_3$ | $CF_3$ | Cl | $CH_3$ | $CF_3$ | Cl | $CH_3$ | $CF_3$ | Cl |
| $CH_3$ | $CF_3$ | Br | $CH_3$ | $CF_3$ | Br | $CH_3$ | $CF_3$ | Br | $CH_3$ | $CF_3$ | Br |
| $CH_3$ | Br | Cl | $CH_3$ | Br | Cl | $CH_3$ | Br | Cl | $CH_3$ | Br | Cl |
| $CH_3$ | Br | Br | $CH_3$ | Br | Br | $CH_3$ | Br | Br | $CH_3$ | Br | Br |
| $CH_3$ | Cl | Cl | $CH_3$ | Cl | Cl | $CH_3$ | Cl | Cl | $CH_3$ | Cl | Cl |
| $CH_3$ | Cl | Br | $CH_3$ | Cl | Br | $CH_3$ | Cl | Br | $CH_3$ | Cl | Br |
| Cl | H | Cl | Cl | H | Cl | Cl | H | Cl | Cl | H | Cl |
| Cl | H | Br | Cl | H | Br | Cl | H | Br | Cl | H | Br |
| Cl | I | Cl | Cl | I | Cl | Cl | I | Cl | Cl | I | Cl |
| Cl | I | Br | Cl | I | Br | Cl | I | Br | Cl | I | Br |
| Cl | F | Cl | Cl | F | Cl | Cl | F | Cl | Cl | F | Cl |
| Cl | F | Br | Cl | F | Br | Cl | F | Br | Cl | F | Br |
| Cl | $CF_3$ | Cl | Cl | $CF_3$ | Cl | Cl | $CF_3$ | Cl | Cl | $CF_3$ | Cl |
| Cl | $CF_3$ | Br | Cl | $CF_3$ | Br | Cl | $CF_3$ | Br | Cl | $CF_3$ | Br |
| Cl | Br | Cl | Cl | Br | Cl | Cl | Br | Cl | Cl | Br | Cl |

TABLE 32-continued

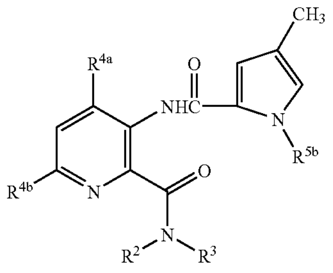

| $R^2$ is H, $R^3$ is Me | | | $R^2$ is H, $R^3$ is Et | | | $R^2$ is H, $R^3$ is i-Pr | | | $R^2$ is Me, $R^3$ is Me | | |
|---|---|---|---|---|---|---|---|---|---|---|---|
| $R^{4a}$ | $R^{4b}$ | $R^6$ | $R^{4a}$ | $R^{4b}$ | $R^6$ | $R^{4a}$ | $R^{4b}$ | $R^6$ | $R^{4a}$ | $R^{4b}$ | $R^6$ |
| Cl | Br | Br | Cl | Br | Br | Cl | Br | Br | Cl | Br | Br |
| Cl | Cl | Cl | Cl | Cl | Cl | Cl | Cl | Cl | Cl | Cl | Cl |
| Cl | Cl | Br | Cl | Cl | Br | Cl | Cl | Br | Cl | Cl | Br |
| Br | H | Cl | Br | H | Cl | Br | H | Cl | Br | H | Cl |
| Br | H | Br | Br | H | Br | Br | H | Br | Br | H | Br |
| Br | I | Cl | Br | I | Cl | Br | I | Cl | Br | I | Cl |
| Br | I | Br | Br | I | Br | Br | I | Br | Br | I | Br |
| Br | F | Cl | Br | F | Cl | Br | F | Cl | Br | F | Cl |
| Br | F | Br | Br | F | Br | Br | F | Br | Br | F | Br |
| Br | $CF_3$ | Cl | Br | $CF_3$ | Cl | Br | $CF_3$ | Cl | Br | $CF_3$ | Cl |
| Br | $CF_3$ | Br | Br | $CF_3$ | Br | Br | $CF_3$ | Br | Br | $CF_3$ | Br |
| Br | Br | Cl | Br | Br | Cl | Br | Br | Cl | Br | Br | Cl |
| Br | Br | Br | Br | Br | Br | Br | Br | Br | Br | Br | Br |
| Br | Cl | Cl | Br | Cl | Cl | Br | Cl | Cl | Br | Cl | Cl |
| Br | Cl | Br | Br | Cl | Br | Br | Cl | Br | Br | Cl | Br |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active*

*Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modem Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

Granule

| | |
|---|---|
| Compound 1 | 10.0% |
| attapulgite granules (low volatile matter, 0.71/0.30 mm; U.S.S. No. 25-50 sieves) | 90.0%. |

EXAMPLE C

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| | |
|---|---|
| Compound 1 | 20.0% |
| blend of oil soluble sulfonates and polyoxyethylene ethers | 10.0% |
| isophorone | 70.0%. |

EXAMPLE E

Granule

| | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armywormn (*Spodoptera fugiperda* J. E. Smith), beet armyworm (*Spodoptera exigua* Hübner), black cutworm (*Agrotis epsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis

*invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimrnon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugna* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius).*

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent. Examples of such biologically active compounds or agents with which compounds of this invention can be formulated are: insecticides such as abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflurnuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazirn, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino) 4H-imidazol-4one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furarnetapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), myclobutanil, neoasozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi. Compounds of this invention and compositions thereof may be applied to plants genetically transformed to express proteins toxic to invertebrate pests (such as *Bacillus thuringiensis* toxin). The effect of the exogenous invertebrate pest control compounds and compositions may be synergistic with the expressed toxin proteins.

A general reference for these agricultural protectants is *The Pesticide Manual,* 12th Edition, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalotlrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of invertebrates in agronomic and/or nonagronomic applications, comprising contacting the invertebrates or their environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

The compounds of this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrates the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A through K and L for compound descriptions. The following abbreviations are used in the Index Tables which follow: t is tertiary, n is normal, i is iso, c is cyclo, s is secondary, Me is methyl, Et is ethyl, Pr is propyl, i-Pr is isopropyl, c-Pr is cyclopropyl, Bu is butyl, s-Bu is secondary butyl, Pent is pentyl, OMe is methoxy, OEt is ethoxy, SMe is methylthio, SEt is ethylthio, CN is cyano, and $NO_2$ is nitro. The abbreviation "Ex." stands for "Example" and is followed by a number indicating in which example the compound is prepared.

INDEX TABLE A

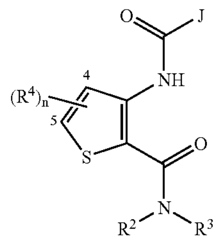

| Compound | $R^2$ | $R^3$ | $(R^4)_n$ | J | m.p. ° C. |
|---|---|---|---|---|---|
| 1 (Ex. 3) | H | i-Pr | 4-Me | 4-$CF_3$—Ph | * |
| 2 | H | t-Bu | 4-Me | 4-$CF_3$—Ph | * |

INDEX TABLE A-continued

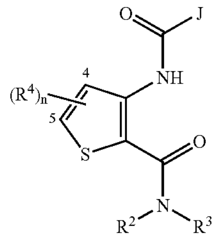

| Compound | $R^2$ | $R^3$ | $(R^4)_n$ | J | m.p. ° C. |
|---|---|---|---|---|---|
| 3 | H | i-Pr | 4-Me | 4-$OCF_3$—Ph | * |
| 4 | H | i-Pr | 4-Me | 2-Me,$SCHF_2$—Ph | |
| 5 | H | t-Bu | 4-Me | 2-Me,$SCHF_2$—Ph | * |
| 6 | H | t-Bu | 4-Me | 4-$OCF_3$—Ph | |
| 7 | H | i-Pr | 4-Me | 2-Me,4-$SO_2CHF_2$—Ph | * |
| 8 | H | i-Pr | 4-Me | 2-Me,4-$SOCF_3$—Ph | * |
| 9 | H | t-Bu | 4-Me | 2-Me,4-$SO_2CHF_2$—Ph | |
| 10 | H | t-Bu | 4-Me | 2-Me,4-$SOCHF_2$—Ph | * |
| 11 | H | i-Pr | 4-Me | $SCHF_2$—Ph | * |
| 12 | H | t-Bu | 4-Me | $SCHF_2$—Ph | |
| 13 | H | i-Pr | 4-Me | 2-Me,4-$CF_{3—Ph}$ | * |
| 14 | H | i-Pr | 4-Me | 2-Me,4-$OCF_3$—Ph | |
| 15 | H | t-Bu | 4-Me | 2-Me,4-$CF_{3—Ph}$ | * |
| 16 | H | t-Bu | 4-Me | 2-Me,4-$OCF_3$—Ph | * |
| 17 | H | i-Pr | 4-Me | 2-Me,4-Cl—Ph | 222.5-225 |
| 18 | H | t-Bu | 4-Me | 2-Me,4-Cl—Ph | 214-215 |
| 19 | H | i-Pr | 4-Me | 2-Me—6-$CF_3$-3-pyridinyl | |
| 20 | H | t-Bu | 4-Me | 2-Me—6-$CF_3$-3-pyridinyl | |
| 21 | H | i-Pr | 4-Me | 1-Ph—3-Me-5-pyrazolyl | |
| 22 | H | t-Bu | 4-Me | 1-Ph—3-Me-5-pyrazolyl | |
| 23 | H | i-Pr | 4-Me | 2-Me—6-Cl-3-pyridinyl | |
| 24 | H | t-Bu | 4-Me | 2-Me—6-Cl-3-pyridinyl | |
| 25 | H | $CH_2CH_2NMe_2$ | 4,5-$Me_2$ | Ph | |
| 26 | —$CH_2CH_2CH_2CH_2$— | H | Ph | | |
| 27 | H | c-hexyl | H | Ph | |
| 28 | H | c-propyl | H | Ph | |
| 29 | H | H | 4-t-Bu—Ph | 3,5-$Cl_2$—Ph | |
| 35 | H | Me | 4-Me | 1-(2-Cl-Ph)-3-$CF_3$-5-pyrazolyl | 201-203 |
| 36 | H | Me | 4,5-$Cl_2$ | 1-(2-Cl-Ph)-3-$CF_3$-5-pyrazolyl | 238-240 |
| 37 | H | i-Pr | 4,5-$Cl_2$ | 1-(2-Cl-Ph)-3-$CF_3$-5-pyrazolyl | 240 |
| 40 | H | i-Pr | 4-Me—5-Cl | 1-(2-Cl-3-pyridinyl)-3-$CF_3$-5-pyrazolyl | 234-236 |

*See Index Table L for $^1$H NMR data.

INDEX TABLE B

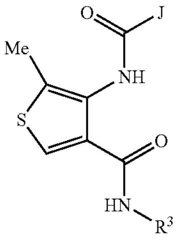

| Compound | $R^3$ | J | m.p. ° C. |
|---|---|---|---|
| B1 | i-Pr | 2-Me,$SCHF_2$—Ph | 178.5-180.5 |
| B2 | i-Pr | 2-Me,4-$SO_2CHF_2$—Ph | 207-210 |
| B4 | i-Pr | 2-Me,4-$CF_3$—Ph | 201-203 |
| B5 | i-Pr | 2-Me-6-$CF_3$-3-pyridinyl | 221-5-222.5 |
| B6 | i-Pr | 1-Ph-3-Me-5-pyrazolyl | |

INDEX TABLE B-continued

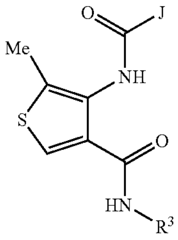

| Compound | $R^3$ | J | m.p. ° C. |
|---|---|---|---|
| B7 | t-Bu | 1-Ph-3-Me-5-pyrazolyl | |
| B8 | t-Bu | 2-Me-6-$CF_3$-3-pyridinyl | |
| B9 | i-Pr | 2-Me-5-Cl-3-thienyl | |
| B10 | Me | 1-(2-Cl-Ph)-3-$CF_3$-5-pyrazolyl | 266-270 |
| B11 | i-Pr | 1-(2-Cl-Ph)—3-$CF_3$-5-pyrazolyl | 232-236 |

*See Index Table L for $^1$H NMR data.

INDEX TABLE C

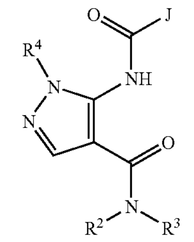

| Compound | $R^2$ | $R^3$ | $R^4$ | J | m.p. ° C. |
|---|---|---|---|---|---|
| C1 | H | i-Pr | Me | 4-F—Ph | * |
| C2 | H | i-Pr | Me | 4-Br—Ph | * |
| C3 | H | i-Pr | Me | 4-Cl—Ph | * |
| C4 | H | i-Pr | Me | 2-$NO_2$—Ph | |
| C5 | H | i-Pr | Me | 3-Cl—Ph | * |
| C6 | H | i-Pr | Me | 4-CN—Ph | |
| C7 | H | i-Pr | Me | 4-$CF_3$—Ph | |
| C8 | H | i-Pr | Me | 2-Me—4-$SOCF_3$—Ph | * |
| C9 Ex. 2) | H | i-Pr | Me | 4-$OCF_3$—Ph | 68-75 |
| C10 | H | i-Pr | Me | 2-Me—4-Br—Ph | * |
| C11 | Pr | Pr | Ph | 3-F—Ph | |
| C12 | —$(CH_2)_5$— | | Ph | 2-thienyl | |
| C13 | —$(CH_2)_2NMe(CH_2)_2$— | | Ph | 4-$NO_2$—Ph | |
| C14 | H | i-Pr | Me | 3-pyridinyl | |
| C15 | H | c-hexyl | Ph | 2-thienyl | |
| C16 | allyl | ally | Ph | 2-Me—Ph | |
| C17 | Et | Et | Ph | Ph | |
| C18 | H | ally | Ph | Ph | |
| C19 | H | $(CH_2)_2Ph$ | Ph | Ph | |
| C20 | Me | Me | Ph | 4-Me—Ph | |
| C21 | —$(CH_2)_2NMe(CH_2)_2$— | | Ph | 4-Br—Ph | |
| C22 | —$(CH_2)_2O(CH_2)_2$— | | Ph | Ph | |
| C27 | H | i-Pr | Me | 1-(2-Cl-Ph)-3-$CF_3$-5-pyrazolyl | 218-220 |
| C28 | H | i-Pr | Me | 1-(2-Cl-Ph)-3-Br-5-pyrazolyl | 170-173 |
| C29 | H | $CH_2$-2-furanyl | Ph | 3-Me—Ph | |
| C42 | | —$(CH_2)_6$— | Ph | 4-Br—Ph | |
| C43 | | —$(CH_2)_4$— | Ph | 4-Me—Ph | |
| C44 | | —$(CH_2)_5$— | Ph | 3-F—Ph | |
| C45 | | —$(CH_2)_4$— | Ph | 3-F—Ph | |
| C46 | H | $CH_2Ph$ | Ph | 2-F—Ph | |
| C47 | H | $CH_2$-2-furanyl | Ph | 3-F—Ph | |
| C48 | | —$(CH_2)_6$— | Ph | 4-Me—Ph | |
| C49 | —$(CH_2)_2O(CH_2)_2$— | | Ph | 2-Me—Ph | |

*See Index Table L for $^1$NMR data.

INDEX TABLE D

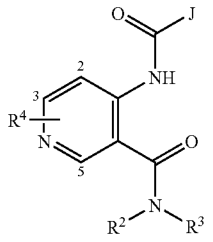

| Compound | $R^2$ | $R^3$ | $R^4$ | J | m.p. ° C. |
|---|---|---|---|---|---|
| D1 | H | i-Pr | 2-Me | 4-$CF_3$-Ph | 223-225 |
| D2 | H | t-Bu | 2-Me | 4-$CF_3$-Ph | 260-261 |
| D3 (Ex. 1) | H | i-Pr | 2-Me | 4-$OCF_3$-Ph | 202-204 |
| D4 | H | i-Pr | 2-Me | 2-Me,4-$CF_3$-Ph | 235-236 |
| D5 | H | i-Pr | 2-Me | 2-Me,4-$OCF_3$-Ph | 198-200 |
| D6 | H | i-Pr | 2-Me | 2-Me-6-$CF_3$-3-pyridinyl | 240-243 |
| D7 | H | i-Pr | 2-Me | 1-Ph-3-$CF_3$-5-pyrazolyl | 215-220 (dec.) |

INDEX TABLE D-continued

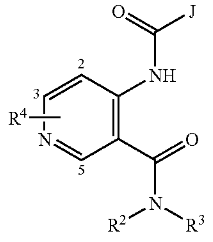

| Compound | $R^2$ | $R^3$ | $R^4$ | J | m.p. ° C. |
|---|---|---|---|---|---|
| D8 | H | i-Pr | 2-Me | 1-(2-Cl-Ph)-3-$CF_3$-5-pyrazolyl | 140-144 |
| D9 | H | i-Pr | 2-Me | 2-Me-3-Cl-Ph | 260-261 |
| D11 | Me | Me | 2-Me | 1-(2-Cl-Ph)-3-$CF_3$-5-pyrazolyl | 172-175 |
| D12 | H | Me | 2-Me | 1-(2-Cl-Ph)-3-$CF_3$-5-pyrazolyl | 193-195 |

INDEX TABLE E

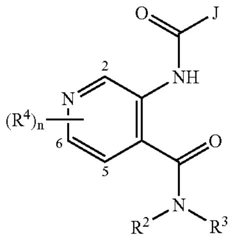

| Compound | $R^2$ | $R^3$ | $(R^4)_n$ | J | m.p. ° C. |
|---|---|---|---|---|---|
| E1 | H | i-Pr | H | 4-$CF_3$-Ph | * |
| E2 | H | i-Pr | H | 4-$OCF_3$-Ph | * |
| E3 | H | i-Pr | 2-Cl | 4-$CF_3$-Ph | * |
| E4 | H | i-Pr | H | 2-Me,3-Cl-Ph | * |
| E5 | H | i-Pr | 2-Me | 1-(2-Cl-3-pyridinyl)-3-$CF_3$-5-pyrazolyl | 138-140 |
| E6 | H | i-Pr | 2-Me | 1-(2-Cl-Ph)-3-$CF_3$-5-pyrazolyl | 170-173 |
| E7 | H | i-Pr | 2-Me | 1-(2-Cl-Ph)-3-Br-5-pyrazolyl | * |
| E15 (Ex. 5) | H | i-Pr | 2,6-$Cl_2$ | 1-(2-Cl-3-pyridinyl)-3-$CF_3$-5-pyrazolyl | 240-242 |
| E18 | Me | Me | 2,6-$Br_2$ | 2,6-$Br_2$-3-$NH_2$-4-pyridinyl | 208-210 |
| E27 | H | Me | 2,6-$Br_2$ | 1-(2-Cl-Ph)-3-$CF_3$-5-pyrazolyl | * |
| E28 | H | Et | 2,6-$Br_2$ | 1-(2-Cl-Ph)-3-$CF_3$-5-pyrazolyl | * |
| E34 | H | i-Pr | 2,6-$Br_2$ | 1-(2-Cl-Ph)-3-$CF_3$-5-pyrazolyl | * |
| E35 | H | $NMe_2$ | 2,6-$Cl_2$ | 2,6-$Cl_2$-3-$NH_2$-4-pyridinyl | * |
| E36 | Et | Et | 2,6-$Cl_2$ | 2,6-$Cl_2$-3-$NH_2$-4-pyridinyl | * |

*See Index Table L for $^1$H NMR data.

INDEX TABLE F

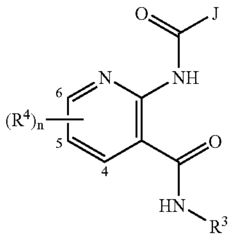

| Compound | $R^3$ | $(R^4)_n$ | J | m.p. ° C. |
|---|---|---|---|---|
| F1 | i-Pr | H | 4-$CF_3$-Ph | * |
| F2 | t-Bu | H | 4-$CF_3$-Ph | 199-200 |
| F3 | i-Pr | 6-Me | 4-$CF_3$-Ph | 218-220 |
| F4 | i-Pr | 4,6-$Me_2$ | 4-$CF_3$-Ph | 235-237 |

INDEX TABLE F-continued

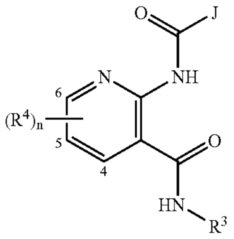

| Compound | $R^3$ | $(R^4)_n$ | J | m.p. ° C. |
|---|---|---|---|---|
| F5 | i-Pr | 6-Me | 2-Me-4-Cl-Ph | 172-174 |
| F6 | t-Bu | H | 2-Me-3-Cl-Ph | 218-220 |
| F7 | i-Pr | H | 2-Me-3-Cl-Ph | |

*See Index Table L for $^1$H NMR data.

INDEX TABLE G

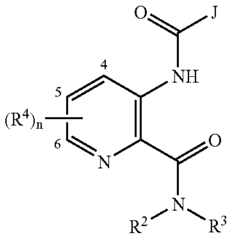

| Compound | $R^2$ | $R^3$ | $(R^4)_n$ | J | m.p. ° C. |
|---|---|---|---|---|---|
| G1 | H | i-Pr | 4-Me | 4-$CF_3$-Ph | 121-123* |
| G3 | H | S—CH(Ph)Me | H | 3-pyridinyl | |
| G5 | H | i-Pr | 4-Me | 1-(2-Cl-3-Ph)-3-Br-5-pyrazolyl | |
| G14 | H | $NMe_2$ | 4,6-$Cl_2$ | 4,6-$Cl_2$-3-$NH_2$-2-pyridinyl | 192-194 |
| G15 | Me | Me | 4,6-$Cl_2$ | 4,6-$Cl_2$-3-$NH_2$-2-pyridinyl | 171-172 |

*See Index Table L for $^1$H NMR data

INDEX TABLE H

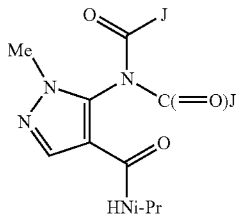

| Compound | J | m.p. ° C. |
|---|---|---|
| H1 | 2-Me-4-Br-Ph | * |

*See Index Table J for $^{1}$H NMR data.

INDEX TABLE I

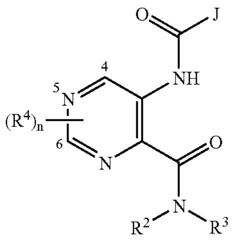

| Compound | $R^2$ | $R^3$ | $(R^4)_n$ | J | m.p. ° C. |
|---|---|---|---|---|---|
| I6 (Ex. 4) | Me | Me | 4-Me | 1-(3-Cl-3-pyridinyl)-3-Cl-5-pyrazolyl | 232-236 |

*See Index Table L for $^{1}$H NMR data.

INDEX TABLE J

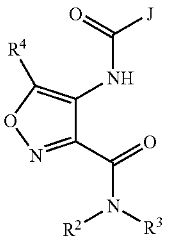

| Compound | $R^2$ | $R^3$ | $R^4$ | J | m.p. ° C. |
|---|---|---|---|---|---|
| J1 | H | i-Pr | Me | 1-(2-Cl-Ph)-3-$CF_3$-5-pyrazolyl | 174-176 |

INDEX TABLE K

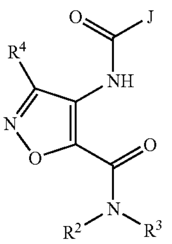

| Compound | $R^2$ | $R^3$ | $R^4$ | J | m.p. ° C. |
|---|---|---|---|---|---|
| K3 | H | Me | Me | 1-(2-Cl-Ph)-3-$CF_3$-5-pyrazolyl | 185-190 |
| K4 | H | i-Pr | Me | 1-(2-Cl-Ph)-3-$CF_3$-5-pyrazolyl | 160-162 |

*See Index Table L for $^{1}$H NMR data.

INDEX TABLE L

| Compd. No. | $^{1}$H NMR Partial Spectrum Data ($CDCl_3$ solution unless indicated otherwise)[a] |
|---|---|
| 1 | 10.63(s, 1H), 5.58(d, 1H) |
| 2 | 10.55(s, 1H), 5.60(s, 1H) |
| 3 | 10.55(s, 1H), 5.58(d, 1H) |
| 4 | 9.80(s, 1H), 5.60(d, 1H) |
| 5 | 9.68(s, 1H), 5.60(s, 1H) |
| 6 | 10.45(s, 1H), 5.60(d, 1H) |
| 7 | 9.93(s, 1H), 5.60(d, 1H) |
| 8 | 9.90(s, 1H), 5.59(d, 1H) |
| 9 | 9.83(s, 1H), 5.60(s, 1H) |
| 10 | 9.78(s, 1H), 5.60(s, 1H) |
| 11 | 10.57(s, 1H), 5.58(d, 1H) |
| 12 | 10.46(s, 1H), 5.60(s, 1H) |
| 13 | 9.85(s, 1H), 5.60(d, 1H) |
| 14 | 9.82(s, 1H), 5.58(d, 1H) |
| 15 | 9.76(s, 1H), 5.62(s, 1H) |
| 16 | 9.68(s, 1H), 5.60(s, 1H) |
| C1 | 10.19(s, 1H), 5.72(d, 1H) |
| C2 | 10.23(s, 1H), 5.71(d, 1H) |
| C3 | 10.23(s, 1H), 5.66(s, 1H) |
| C4 | 9.50(s, 1H), 5.62(d, 1H) |
| C5 | 10.18(s, 1H), 5.67(s, 1H) |
| C6 | 10.41(s, 1H), 5.62(s, 1H) |
| C7 | 10.36(s, 1H), 5.66(s, 1H) |
| C8 | 9.56(s, 1H), 5.54(d, 1H) |
| C10 | 9.56(s, 1H), 5.53(d, 1H) |
| E1 | 10.10(s, 1H), 6.24(s, 1H) |
| E2 | 10.08(s, 1H), 6.30(s, 1H) |
| E3 | 8.36(m, 3H), 7.94(d, 1H), 7.79 (d, 2H), 4.36(m, 1H), 1.32(d, 6H) |
| E4 | 10.05, 1H), 6.16(d, 1H) |
| E7 | 7.75(d, 1H), 7.67(s, 1H) |
| E27 | 9.0(s, 1H), 6.2(m, 1H) |
| E28 | 9.25(s, 1H), 6.18(m, 1H) |

INDEX TABLE L-continued

| Compd. No. | $^1H$ NMR Partial Spectrum Data ($CDCl_3$ solution unless indicated otherwise)[a] |
|---|---|
| E34 | 9.5(brs, 1H), 6.05(d, 1H) |
| E35 | (DMSO-$d_6$)10.9(s, 1H), 6.66(m, 1H) |
| E36 | 10.3(s, 1H) |
| F1 | 11.56(s, 1H), 8.41(d, 1H) |
| G1 | 11.97(s, 1H) |
| H1 | 5.56(d, 1H) |

[a] $^1H$ NMR data are in ppm downfield from tetramethylsilane. Couplings are designated by (s)—singlet, (d)—doublet, (t)—triplet, (q)—quartet, (m)—multiplet, (dd)—doublet of doublets, (dt)—doublet of triplets, (brs)—broad singlet.

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in these tests were sprayed at 250 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed.

Of the compounds tested the following provided very good to excellent levels of plant protection (ratings of 0-1, 10% or less feeding damage): 1, 2, 3, 4, 5, 6, 7, 8, 9, 12, 13, 15, 16, 19, 20, 21, 22, 23, 24, 30, 31, 32, 33, 34, 36, 37, 38, B1, B3, B5, B11, B12, B15, C1, C2, C3, C7, C9, C24, D1, D3, D4, D5, D6, D7, D8, D10, D11, D12, D13, D14, D18, D19, D20, D21, E5, E6, E7, E8, E9, E10, E11, E12, E13, E14, E15, E16, E17, E19, E20, E21, E22, G1, G2, G4, G5, G6, G7, G8, G9, G10, G11, G12, G13, J6, K1 and K2.

Test B

For evaluating control of fall armyworm (*Spodoptera frugiperda*) the test unit consisted of a small open container with a 4-5-day-old corn (maize) plant inside. This was pre-infested (using a core sampler) with 10-15 1-day-old larvae on a piece of insect diet.

Test compounds were formulated and sprayed at 250 ppm as described for Test A. The applications were replicated three times. After spraying, the test units were maintained in a growth chamber and then visually rated as described for Test A.

Of the compounds tested, the following provided excellent levels of plant protection (10% or less feeding damage): 30, 31, 32, 33, 34, 35, 36, B10, B11, B12, B13, B14, D1, D3, D7, D8, D10,D11, D14, D15, E5, E6, E7, E9, E10, E11, E12, E13, E22, G2, G4, G5, G6, G7, G9, G10, G11, G12, G13, J6 and K2.

Test C

For evaluating control of tobacco budworm (*Heliothis virescens*) the test unit consisted of a small open container with a 6-7 day old cotton plant inside. This was pre-infested (using a core sampler) with 8 2-day-old larvae on a piece of insect diet.

Test compounds were formulated and sprayed at 250 ppm as described for Test A. The applications were replicated three times. After spraying, the test units were maintained in a growth chamber and then visually rated as described for Test A.

Of the compounds tested, the following provided very good to excellent levels of plant protection (20% or less feeding damage): 31, 32, 33, 34, 35, 36, 37, B12, B13, B14, B15, D1, D4, D5, D6, D8, D10, D11, D12, D13, D14, D15, D18, D19, D20, D21, E5, E6, E7, E9, E10, E12, E15, E20, E21, E22, G2, G5, G6, G7, G8, G9, G10, G11, G12, and G13.

Test D

For evaluating control of beet armyworm (*Spodoptera exigua*) the test unit consisted of a small open container with a 4-5-day-old corn plant inside. This was pre-infested (using a core sampler) with 10-15 1-day-old larvae on a piece of insect diet.

Test compounds were formulated and sprayed at 250 ppm as described for Test A. The applications were replicated three times. After spraying, the test units were maintained in a growth chamber and then visually rated as described for Test A.

Of the compounds tested, the following provided very good to excellent levels of plant protection (20% or less feeding damage): 31, 32, 34, B13, B15, D1, D3, D4, D7, D8, D10, D11, D14, D19, E5, E6, E7, E9, E10, E15, E22, G1, G2, G4, G5, G6, G7, G9, G10, G11, G12, G13, D20, J6and K2.

Test E

For evaluating control of green peach aphid (*Myzus persicae*) through contact and/or systemic means, the test unit consisted of a small open container with a 12-15-day-old radish plant inside. This was pre-infested (using the cut leaf method) with 30-40 insects on each piece of leaf, and the soil was covered with a layer of sand.

Test compounds were formulated and sprayed at 250 ppm as described for Test A. The applications were replicated three times. After spraying, the test units were maintained in a growth chamber and then visually assessed for insect mortality.

Of the compounds tested, the following resulted in at least 80% mortality: C48, E13, E14, E16, G4, G9,G10,G11 and G13.

Test F

For evaluating control of cotton melon aphid (*Aphis gossypii*) through contact and/or systemic means, the test unit consisted of a small open container with a 6-7-day-old cotton plant inside. This was pre-infested (using the cut leaf method) with 30-40 insects on each piece of leaf, and the soil was covered with a layer of sand.

Test compounds were formulated and sprayed at 250 ppm as described for Test A. The applications were replicated three times. After spraying, the test units were maintained in a growth chamber and then visually rated as described for Test E.

Of the compounds tested, the following resulted in at least 80% mortality: E9.

What is claimed is:

1. A compound of Formula I, an N-oxide thereof or suitable salt thereof

I

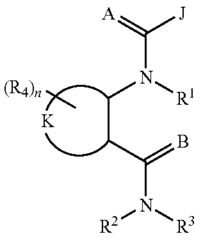

wherein

A and B are both O;

J is selected from the group consisting of J-6, J-7, J-8, J-9, J-10, J-11, J-12 and J-13

J-6

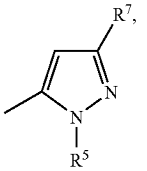

J-7

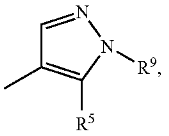

J-8

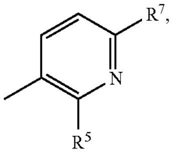

J-9

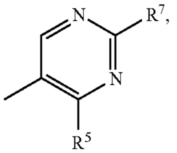

J-10

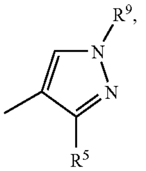

-continued

J-11

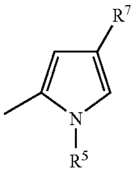

J-12

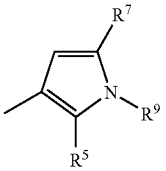

and

J-13

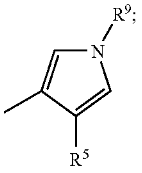

K is, together with the two contiguous linking carbon atoms, a 5- or 6-membered heteroaromatic ring selected from the group consisting of

K-1

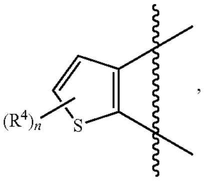

,

K-14

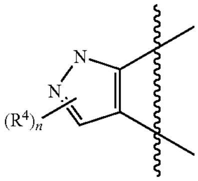

,

K-15

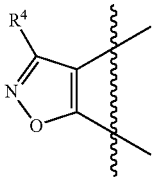

,

K-18

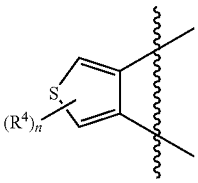

,

-continued

K-23

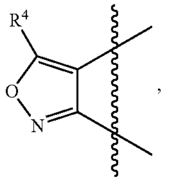

,

K-28

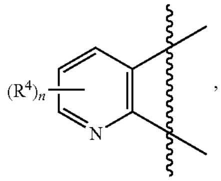

,

K-29

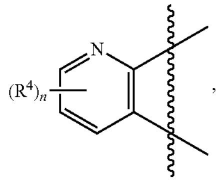

,

K-30

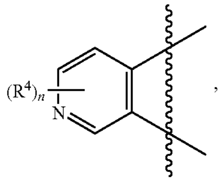

,

K-31

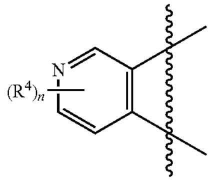

and

K-33

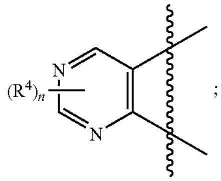

;

n is 1 to 3;

$R^1$ is H; or $C_1$-$C_6$ alkyl;

$R^2$ is H;

$R^3$ is H; or $C_1$-$C_6$ alkyl, $C_2$-$C_6$ alkenyl, $C_2$-$C_6$alkynyl, $C_3$-$C_6$ cycloalkyl, each optionally substituted with one or more substituents selected from the group consisting of halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl;

each $R^4$ is independently $C_1$-$C_4$ alkyl, $C_1$-$C_4$ haloalkyl, halogen, CN, $NO_2$ or $C_1$-$C_4$ alkoxy, and one $R^4$ group is attached to the K ring at the atom adjacent to the $NR^1C(=A)J$ moiety;

$R^5$ is

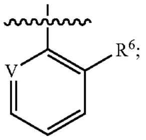

V is N, CH, CF, CCl, CBr or CI;

each $R^6$ and $R^7$ is independently H, $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ haloalkoxy or $C_1$-$C_4$ haloalkylthio; and $R^9$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl; provided $R^7$ and $R^9$ are not both H.

2. The compound of claim 1 wherein V is N.

3. The compound of claim 1 wherein V is CH, CF, CCl or CBr.

4. The compound of claim 2 or claim 3 wherein $R^1$ is H;

$R^2$ is H;

$R^3$ is $C_1$-$C_4$ alkyl optionally substituted with one or more substituents independently selected from halogen, CN, $OCH_3$ or $S(O)_pCH_3$;

each $R^4$ is independently $CH_3$, $CF_3$, CN or halogen, and one $R^4$ group is attached to the K ring at the atom adjacent to the $NR^1C(=A)J$ moiety;

$R^6$ is $C_1$-$C_4$ alkyl, $C_1$-$C_4$ haloalkyl, halogen or CN;

$R^7$ is H, $CH_3$, $CF_3$, $OCH_2CF_3$, $OCHF_2$ or halogen; and p is 0, 1 or 2.

5. The compound of claim 4 wherein $R^3$ is $C_1$-$C_4$ alkyl; one $R^4$ group is independently $CH_3$, Cl, Br or I and is attached to the K ring at the atom adjacent to the $NR^1C(=A)J$ moiety; and a second optional $R^4$ is H, F, Cl, Br, I or $CF_3$.

6. The compound of claim 5 wherein J is J-6; $R^6$ is Cl or Br; and $R^7$ is halogen, $OCH_2CF_3$ or $CF_3$.

7. The compound of claim 6 wherein V is N; $R^3$ is methyl, ethyl, isopropyl or tertiary butyl; and $R^7$ is Br, Cl, $OCH_2CF_3$ or $CF_3$.

8. The compound of claim 5 wherein J is J-7; $R^6$ is Cl or Br; and $R^9$ is $CF_3$, $CHF_2$, $CH_2CF_3$ or $CF_2CHF_2$.

9. The compound of claim 5 wherein J is J-8; $R^6$ is Cl or Br; and $R^7$ is halogen, $OCH_2CF_3$ or $CF_3$.

10. The compound of claim 5 wherein J is J-9; $R^6$ is Cl or Br; and $R^7$ is $OCH_2CF_3$ or $CF_3$.

11. The compound of claim 5 wherein J is J-10; $R^6$ is Cl or Br; and $R^9$ is $CF_3$, $CHF_2$, $CH_2CF_3$ or $CF_2CHF_2$.

12. The compound of claim 5 wherein J is J-11; $R^6$ is Cl or Br; and $R^7$ is halogen, $OCH_2CF_3$ or $CF_3$.

13. The compound of claim 5 wherein J is J-12; $R^6$ is Cl or Br; and $R^7$ is H, halogen or $CF_3$, and $R^9$ is H, $CF_3$, $CHF_2$, $CH_2CF_3$, or $CF_2CHF_2$.

14. The compound of claim 5 wherein J is J-13; $R^6$ is Cl or Br; and $R^9$ is H, $CF_3$, $CHF_2$, $CH_2CF_3$ or $CF_2CHF_2$.

15. The compound of claim 1 selected from the group consisting of:

4-[[[1-(2-Chlorophenyl)-3-(trifluoromethyl)-1H-pyrazol-5-yl]carbonyl]amino]-5-methyl-N-(1-methylethyl)-3-pyridinecarboxamide;

4-[[[3-Bromo-1-(3-chloro-2-pyridinyl)-1H-pyrazol-5-yl]carbonyl]amino]-5-chloro-N-methyl-3-pyridinecarboxamide;

3-[[[3-Bromo-1-(3-chloro-2-pyridinyl)-1H-pyrazol-5-yl]carbonyl]amino]-2,6-dichloro-N-methyl-4-pyridinecarboxamide;

2,6-dichloro-3-[[[1-(3-chloro-2-pyridinyl)-3-trifluoromethyl)-1H-pyrazol-5-yl]carbonyl]amino]-N-(1-methylethyl)-4-pyridinecarboxamide;

3-[[[3-Bromo-1-(3-chloro-2-pyridinyl)-1H-pyrazol-5-yl]carbonyl]amino]-6-chloro-N,4-dimethyl-2-pyridinecarboxamide;

3-[[[3-Bromo-1-(3-chloro-2-pyridinyl)-1H-pyrazol-5-yl]carbonyl]amino]-4,6-dichloro-N-methyl-2-pyridinecarboxamide; and 5-[[[3-Chloro-1-(3-chloro-2-pyridinyl)-1H-pyrazol-5-yl]carbonyl]amino]-N,6-dimethyl-4-pyrimidinecarboxamide.

16. A method for controlling an invertebrate pest comprising contacting the invertebrate pest or its environment with a biologically effective amount of a compound of claim 1.

17. The method of claim 16 further comprising a biologically effective amount of at least one additional compound or agent for controlling invertebrate pests.

* * * * *

UNITED STATES PATENT AND TRADEMARK OFFICE

CERTIFICATE OF CORRECTION

PATENT NO. : 7,560,564 B2
APPLICATION NO. : 11/158200
DATED : July 14, 2009
INVENTOR(S) : Gary David Annis and Bruce Lawrence Finkelstein It is certified that error appears in the above-identified patent and that said Letters Patent is hereby corrected as shown below:

Title page under section “other publications” line 2, “Facelli” should read --Fancelli--

Column 155, under Table 23, below the column heading, heading “$R^5$ is $CF_2CF_2$” should read --$CF_2CHF_2$--

Column 179, under Table 29, heading “$CHF_2$” should read --$R^4$ is $CHF_2$--

Signed and Sealed this
Thirty-first Day of July, 2012

David J. Kappos
*Director of the United States Patent and Trademark Office*